(12) United States Patent
Umeno et al.

(10) Patent No.: US 11,702,763 B2
(45) Date of Patent: Jul. 18, 2023

(54) MULTI-INPUT/MULTI-OUTPUT GENE SWITCH, AND METHOD FOR PRODUCING SAME

(71) Applicant: NATIONAL UNIVERSITY CORPORATION CHIBA UNIVERSITY, Chiba (JP)

(72) Inventors: Daisuke Umeno, Chiba (JP); Yuki Kimura, Chiba (JP); Kyohei Ouchi, Chiba (JP); Shigeko Kawai, Chiba (JP)

(73) Assignee: NATIONAL UNIVERSITY CORPORATION CHIBA UNIVERSITY, Chiba (JP)

(*) Notice: Subject to any disclaimer, the term of this patent is extended or adjusted under 35 U.S.C. 154(b) by 301 days.

(21) Appl. No.: 16/650,899

(22) PCT Filed: Mar. 23, 2019

(86) PCT No.: PCT/JP2019/012285
§ 371 (c)(1),
(2) Date: Mar. 26, 2020

(87) PCT Pub. No.: WO2019/182156
PCT Pub. Date: Sep. 26, 2019

(65) Prior Publication Data
US 2020/0347390 A1   Nov. 5, 2020

(30) Foreign Application Priority Data

Mar. 23, 2018 (JP) .............................. JP2018-057314

(51) Int. Cl.
*C40B 30/04* (2006.01)
*C12N 15/10* (2006.01)
(Continued)

(52) U.S. Cl.
CPC .......... *C40B 30/04* (2013.01); *C12N 15/1072* (2013.01); *C12N 15/1086* (2013.01); *C12N 15/62* (2013.01); *C12N 15/63* (2013.01)

(58) Field of Classification Search
None
See application file for complete search history.

(56) References Cited

U.S. PATENT DOCUMENTS

2013/0267011 A1   10/2013   Umeno et al.
2016/0202256 A1   7/2016   Church et al.

OTHER PUBLICATIONS

International Search Report issued in corresponding International Patent Application No. PCT/JP2019/012285 (with English translation of International Search Report) dated Jun. 25, 2019 (4 pages).
(Continued)

*Primary Examiner* — Christian C Boesen
(74) *Attorney, Agent, or Firm* — Kilyk & Bowersox, P.L.L.C.

(57) ABSTRACT

[Problem] Provided are a production method for a multi-input/multi-output-type genetic switch or a transcription factor, and a multi-input/multi-output-type genetic switch or a transcription factor. [Solving Means] The inventors of the present invention have completed a production method for a multi-input/multi-output-type genetic switch or a transcription factor, essentially including the steps of "fusing two or more transcription factor genes to each other" and "introducing mutations into the fusion-type transcription factor gene," and have further succeeded in obtaining a multi-input/multi-output-type genetic switch or a transcription factor by the method.

10 Claims, 17 Drawing Sheets

Specification includes a Sequence Listing.

(51) Int. Cl.
    *C12N 15/62*           (2006.01)
    *C12N 15/63*           (2006.01)

(56) References Cited

OTHER PUBLICATIONS

Sakei et al., "Rapid di versification of Bet I-based transcriptional switches for the control of biosynthetic pathways and genetic circuits ", ACS Synth. Biol., 2016, vol. 5, No. 11, pp. 1201-1210.

| | L1 | L2 | GATE MODE (OUTPUT MODE) | OUTPUT AMOUNT | PRODUCTION METHOD EXAMPLE |
|---|---|---|---|---|---|
| OR gate | 0 | 0 | 0 | X1 | |
| | 0 | 1 | 1 | X2 | EXAMPLE 2-3 |
| | 1 | 0 | 1 | X2 | |
| | 1 | 1 | 1 | X2 | |

| | L1 | L2 | GATE MODE (OUTPUT MODE) | OUTPUT AMOUNT | PRODUCTION METHOD EXAMPLE |
|---|---|---|---|---|---|
| AND gate | 0 | 0 | 0 | X1 | |
| | 0 | 1 | 0 | X1 | EXAMPLE 2-1, EXAMPLE 2-2 |
| | 1 | 0 | 0 | X1 | |
| | 1 | 1 | 1 | X2 | |

| | L1 | L2 | GATE MODE (OUTPUT MODE) | OUTPUT AMOUNT | PRODUCTION METHOD EXAMPLE |
|---|---|---|---|---|---|
| NOR gate | 0 | 0 | 1 | X2 | A REPORTER GENE (R) IS UNDER THE CONTROL OF A REPRESSOR-TYPE TRANSCRIPTION FACTOR T1, AND MUTATIONS ARE INTRODUCED AFTER FUSION OF T1 WITH ANOTHER TRANSCRIPTION FACTOR (T2; WHICH MAY BE OF A REPRESSOR TYPE OR AN ACTIVATOR TYPE). A FUSION MUTANT THAT EXPRESSES THE REPORTER GENE IN THE PRESENCE OF ANY ONE OF L1 AND L2 IS SELECTED. |
| | 0 | 1 | 0 | X1 | |
| | 1 | 0 | 0 | X1 | |
| | 1 | 1 | 0 | X1 | |

| | L1 | L2 | GATE MODE (OUTPUT MODE) | OUTPUT AMOUNT | PRODUCTION METHOD EXAMPLE |
|---|---|---|---|---|---|
| NAND gate | 0 | 0 | 1 | X2 | A REPORTER GENE (R) IS UNDER THE CONTROL OF A REPRESSOR-TYPE TRANSCRIPTION FACTOR T1, AND MUTATIONS ARE INTRODUCED AFTER FUSION OF T1 WITH ANOTHER TRANSCRIPTION FACTOR (T2; WHICH MAY BE OF A REPRESSOR TYPE OR AN ACTIVATOR TYPE). A FUSION MUTANT THAT EXPRESSES THE REPORTER IN THE PRESENCE OF BOTH OF L1 AND L2 IS SELECTED. |
| | 0 | 1 | 1 | X2 | |
| | 1 | 0 | 1 | X2 | |
| | 1 | 1 | 0 | X1 | |

| | L1 | L2 | GATE MODE (OUTPUT MODE) | OUTPUT AMOUNT | PRODUCTION METHOD EXAMPLE |
|---|---|---|---|---|---|
| GATE THAT SPECIFICALLY RESPONDS TO L1 | 0 | 0 | 0 | X1 | |
| | 0 | 1 | 0 | X1 | EXAMPLE 2-4, EXAMPLE 2-5 |
| | 1 | 0 | 1 | X2 | |
| | 1 | 1 | 1 | X2 | |

| | L1 | L2 | GATE MODE (OUTPUT MODE) | OUTPUT AMOUNT | PRODUCTION METHOD EXAMPLE |
|---|---|---|---|---|---|
| GATE THAT SPECIFICALLY RESPONDS TO L2 | 0 | 0 | 0 | X1 | |
| | 0 | 1 | 1 | X2 | EXAMPLE 2-4, EXAMPLE 2-5 |
| | 1 | 0 | 0 | X1 | |
| | 1 | 1 | 1 | X2 | |

| | L1 | L2 | GATE MODE (OUTPUT MODE) | OUTPUT AMOUNT | PRODUCTION METHOD EXAMPLE |
|---|---|---|---|---|---|
| 2-INPUT/3-STAGE OUTPUT REDUCTION-TYPE GATE | 0 | 0 | | X3 | A REPORTER GENE (R) IS UNDER THE CONTROL OF A REPRESSOR-TYPE TRANSCRIPTION FACTOR T1, AND A FUSION MUTANT IN WHICH BOTH OF THE FOLLOWING EXPRESSION AMOUNTS OF THE REPORTER ARE DECREASED IS SELECTED: THE EXPRESSION AMOUNT OF THE REPORTER OBTAINED BY INTRODUCTION OF THE LIGAND L1 AND THE EXPRESSION AMOUNT OF THE REPORTER OBTAINED BY INTRODUCTION OF THE LIGAND L2. |
| | 0 | 1 | | X2 | |
| | 1 | 0 | | X2 | |
| | 1 | 1 | | X1 | |

| | L1 | L2 | GATE MODE (OUTPUT MODE) | OUTPUT AMOUNT | PRODUCTION METHOD EXAMPLE |
|---|---|---|---|---|---|
| 2-INPUT/3-STAGE OUTPUT INCREASE-TYPE GATE | 0 | 0 | 0 | X1 | A REPORTER GENE (R) IS UNDER THE CONTROL OF AN ACTIVATOR-TYPE TRANSCRIPTION FACTOR T1, AND A FUSION MUTANT IN WHICH BOTH OF THE FOLLOWING EXPRESSION AMOUNTS OF THE REPORTER ARE INCREASED IS SELECTED: THE EXPRESSION AMOUNT OF THE REPORTER OBTAINED BY INTRODUCTION OF THE LIGAND L1 AND THE EXPRESSION AMOUNT OF THE REPORTER OBTAINED BY INTRODUCTION OF THE LIGAND L2. |
| | 0 | 1 | 1 | X2 | |
| | 1 | 0 | 1 | X2 | |
| | 1 | 1 | 1 | X3 | |

SEQUENCE LISTING

<160> NUMBER OF SEQ ID NOS: 32

<210> SEQ ID NO 1
<211> LENGTH: 34
<212> TYPE: DNA
<213> ORGANISM: Artificial Sequence
<220> FEATURE:
<223> OTHER INFORMATION: SpeI-luxR-Fwd primer

<400> SEQUENCE: 1
ttttactagt gaaaacataa atgccgacga caca            34

<210> SEQ ID NO 2
<211> LENGTH: 39
<212> TYPE: DNA
<213> ORGANISM: Artificial Sequence
<220> FEATURE:
<223> OTHER INFORMATION: SpeI-tetR-Rev primer

<400> SEQUENCE: 2
ttttactagt ggacccactt tcacatttaa gttgttttt            39

<210> SEQ ID NO 3
<211> LENGTH: 40
<212> TYPE: DNA
<213> ORGANISM: Artificial Sequence
<220> FEATURE:
<223> OTHER INFORMATION: pET23d-XhoI-Fwd primer

<400> SEQUENCE: 3
ttttctcgag atgtcatttc tgttacccat ccaattgttc            40

<210> SEQ ID NO 4
<211> LENGTH: 35
<212> TYPE: DNA
<213> ORGANISM: Artificial Sequence
<220> FEATURE:
<223> OTHER INFORMATION: SpeI-eArsR-Rev primer

<400> SEQUENCE: 4
ttttactagt actgcaaatg ttcttactgt ccccg            35

<210> SEQ ID NO 5
<211> LENGTH: 35
<212> TYPE: DNA
<213> ORGANISM: Artificial Sequence
<220> FEATURE:
<223> OTHER INFORMATION: BamHI-eArsR-Rev primer

<400> SEQUENCE: 5
ttttggatcc actgcaaatg ttcttactgt ccccg            35

<210> SEQ ID NO 6
<211> LENGTH: 80
<212> TYPE: DNA
<213> ORGANISM: Artificial Sequence
<220> FEATURE:
<223> OTHER INFORMATION: pACmod3 PT5-arsO-sfgfp Rev primer

<400> SEQUENCE: 6
ttttggtctc aaaacatata tgacttaacg aatgtgtatt atacagaaaa attttcctga      60
aagcaaataa attttttcatg            80

<210> SEQ ID NO 7
<211> LENGTH: 77

<212> TYPE: DNA
<213> ORGANIZM: Artificial Sequence
<220> FEATURE:
<223> OTHER INFORMATION: pACmod3 PT5-ars0-sfgfp Fwd primer

<400> SEQUENCE: 7
ttttggtctc agttttttgac tttagcacga gctsaakaat acargragac kmtcaatggg    60
gtctaaaggc gaagaac    77

<210> SEQ ID NO 8
<211> LENGTH: 25
<212> TYPE: DNA
<213> ORGANISM: Artificial Sequence
<220> FEATURE:
<223> OTHER INFORMATION: BamHI-His-Fwd primer

<400> SEQUENCE: 8
ttttggatcc catcatcacc atcac    25

<210> SEQ ID NO 9
<211> LENGTH: 23
<212> TYPE: DNA
<213> ORGANISM: Artificial Sequence
<220> FEATURE:
<223> OTHER INFORMATION: luxR-seq-Rev-1 primer

<400> SEQUENCE: 9
agcattccga agccattgtt agc    23

<210> SEQ ID NO 10
<211> LENGTH: 22
<212> TYPE: DNA
<213> ORGANISM: Artificial Sequence
<220> FEATURE:
<223> OTHER INFORMATION: ROP-seq-Fwd primer

<400> SEQUENCE: 10
gataaagcgg gccatgttaa gg    22

<210> SEQ ID NO 11
<211> LENGTH: 29
<212> TYPE: DNA
<213> ORGANISM: Artificial Sequence
<220> FEATURE:
<223> OTHER INFORMATION: Y-T7tn-gfp-sq-R primer

<400> SEQUENCE: 11
tcagcaaaaa acccctcaag acccgttta    29

<210> SEQ ID NO 12
<211> LENGTH: 30
<212> TYPE: DNA
<213> ORGANISM: Artificial Sequence
<220> FEATURE:
<223> OTHER INFORMATION: pUC vector Rev (KpnI) primer

<400> SEQUENCE: 12
ttttggtacc cctggggtgc ctaatgagtg    30

<210> SEQ ID NO 13
<211> LENGTH: 35
<212> TYPE: DNA
<213> ORGANISM: Artificial Sequence
<220> FEATURE:
<223> OTHER INFORMATION: pUC vector Fwd (HindIII) primer

```
<400> SEQUENCE: 13
ttttaagctt catatggtgc actctcagta caatc                                35

<210> SEQ ID NO 14
<211> LENGTH: 30
<212> TYPE: DNA
<213> ORGANISM: Artificial Sequence
<220> FEATURE:
<223> OTHER INFORMATION: pET23d-Fwd (KpnI) primer

<400> SEQUENCE: 14
ttttggtacc gtgagggtaa acaactggcg                                       30

<210> SEQ ID NO 15
<211> LENGTH: 551
<212> TYPE: PRT
<213> ORGANISM: Artificial Sequence
<220> FEATURE:
<223> OTHER INFORMATION: Full length amino acids sequence of AraC-LuxR
      N86K and C245W

<400> SEQUENCE: 15
```

Met Ala Glu Ala Gln Asn Asp Pro Leu Leu Pro Gly Tyr Ser Phe Asn
1               5                   10                  15

Ala His Leu Val Ala Gly Leu Thr Pro Ile Glu Ala Asn Gly Tyr Leu
            20                  25                  30

Asp Phe Phe Ile Asp Arg Pro Leu Gly Met Lys Gly Tyr Ile Leu Asn
        35                  40                  45

Leu Thr Ile Arg Gly Gln Gly Val Val Lys Asn Gln Gly Arg Glu Phe
    50                  55                  60

Val Cys Arg Pro Gly Asp Ile Leu Leu Phe Pro Pro Gly Glu Ile His
65                  70                  75                  80

His Tyr Gly Arg His Pro Glu Ala Arg Glu Trp Tyr His Gln Trp Val
                85                  90                  95

Tyr Phe Arg Pro Arg Ala Tyr Trp His Glu Trp Leu Asn Trp Pro Ser
            100                 105                 110

Ile Phe Ala Asn Thr Gly Phe Phe Arg Pro Asp Glu Ala His Gln Pro
        115                 120                 125

His Phe Ser Asp Leu Phe Gly Gln Ile Ile Asn Ala Gly Gln Gly Glu
    130                 135                 140

Gly Arg Tyr Ser Glu Leu Leu Ala Ile Asn Leu Leu Glu Gln Leu Leu
145                 150                 155                 160

Leu Arg Arg Met Glu Ala Ile Asn Glu Ser Leu His Pro Pro Met Asp
                165                 170                 175

Asn Arg Val Arg Glu Ala Cys Gln Tyr Ile Ser Asp His Leu Ala Asp
            180                 185                 190

Ser Asn Phe Asp Ile Ala Ser Val Ala Gln His Val Cys Leu Ser Pro
        195                 200                 205

Ser Arg Leu Ser His Leu Phe Arg Gln Gln Leu Gly Ile Ser Val Leu
    210                 215                 220

Ser Trp Arg Glu Asp Gln Arg Ile Ser Gln Ala Lys Leu Leu Leu Ser
225                 230                 235                 240

Thr Thr Arg Met Pro Ile Ala Thr Val Gly Arg Asn Val Gly Phe Asp
                245                 250                 255

Asp Gln Leu Tyr Phe Ser Arg Val Phe Lys Lys Cys Thr Gly Ala Ser
            260                 265                 270

Pro Ser Glu Phe Arg Ala Gly Cys Glu Glu Lys Val Asn Asp Val Ala

```
            275                 280                 285
Val Lys Leu Ser Thr Ser Glu Asn Ile Asn Ala Asp Asp Thr Tyr Arg
        290                 295                 300

Ile Ile Asn Lys Ile Lys Ala Cys Arg Ser Asn Asn Asp Ile Asn Gln
305                 310                 315                 320

Cys Leu Ser Asp Met Thr Lys Met Val His Cys Glu Tyr Tyr Leu Leu
                325                 330                 335

Ala Ile Ile Tyr Pro His Ser Met Val Lys Ser Asp Ile Ser Ile Leu
            340                 345                 350

Asp Asn Tyr Pro Lys Lys Trp Arg Gln Tyr Tyr Asp Asp Ala Asn Leu
        355                 360                 365

Ile Lys Tyr Asp Pro Ile Val Asp Tyr Ser Lys Ser Asn His Ser Pro
370                 375                 380

Ile Asn Trp Asn Ile Phe Glu Asn Asn Ala Val Asn Lys Lys Ser Pro
385                 390                 395                 400

Asn Val Ile Lys Glu Ala Lys Thr Ser Gly Leu Ile Thr Gly Phe Ser
                405                 410                 415

Phe Pro Ile His Thr Ala Asn Asn Gly Phe Gly Met Leu Ser Phe Ala
            420                 425                 430

His Ser Glu Lys Asp Asn Tyr Ile Asp Ser Leu Phe Leu His Ala Cys
        435                 440                 445

Met Asn Ile Pro Leu Ile Val Pro Ser Leu Val Asp Asn Tyr Arg Lys
    450                 455                 460

Ile Asn Ile Ala Asn Asn Lys Ser Asn Asn Asp Leu Thr Lys Arg Glu
465                 470                 475                 480

Lys Glu Cys Leu Ala Trp Ala Cys Glu Gly Lys Ser Ser Trp Asp Ile
                485                 490                 495

Ser Lys Ile Leu Gly Cys Ser Glu Arg Thr Val Thr Phe His Leu Thr
            500                 505                 510

Asn Ala Gln Met Lys Leu Asn Thr Thr Asn Arg Cys Gln Ser Ile Ser
        515                 520                 525

Lys Ala Ile Leu Thr Gly Ala Ile Asp Trp Pro Tyr Phe Lys Asn Gly
    530                 535                 540

Ser His His His His His His
545                 550

<210> SEQ ID NO 16
<211> LENGTH: 770
<212> TYPE: PRT
<213> ORGANISM: Artificial Sequence
<220> FEATURE:
<223> OTHER INFORMATION: Full length amino acids sequence of TetR-AraC-
      LuxR N86K and C245W

<400> SEQUENCE: 16

Met Ala Arg Leu Asn Arg Glu Ser Val Ile Asp Ala Ala Leu Glu Leu
1               5                   10                  15

Leu Asn Glu Thr Gly Ile Asp Gly Leu Thr Thr Arg Lys Leu Ala Gln
            20                  25                  30

Lys Leu Gly Ile Glu Gln Pro Thr Leu Tyr Trp His Val Lys Asn Lys
        35                  40                  45

Arg Ala Leu Leu Asp Ala Leu Ala Val Glu Ile Leu Ala Arg His His
    50                  55                  60

Asp Tyr Ser Leu Pro Ala Ala Gly Glu Ser Trp Gln Ser Phe Leu Arg
65                  70                  75                  80
```

```
Asn Asn Ala Met Ser Phe Arg Arg Ala Leu Leu Arg Tyr Arg Asp Gly
                85                  90                  95
Ala Lys Val His Leu Gly Thr Arg Pro Asp Glu Lys Gln Tyr Asp Thr
            100                 105                 110
Val Glu Thr Gln Leu Arg Phe Met Thr Glu Asn Gly Phe Ser Leu Arg
        115                 120                 125
Asp Gly Leu Tyr Ala Ile Ser Ala Val Ser His Phe Thr Leu Gly Ala
    130                 135                 140
Val Leu Glu Gln Gln Glu His Thr Ala Ala Leu Thr Asp Arg Pro Ala
145                 150                 155                 160
Ala Pro Asp Glu Asn Leu Pro Pro Leu Arg Glu Ala Leu Gln Ile
                165                 170                 175
Met Asp Ser Asp Asp Gly Glu Gln Ala Phe Leu His Gly Leu Glu Ser
            180                 185                 190
Leu Ile Arg Gly Phe Glu Val Gln Leu Thr Ala Leu Leu Gln Ile Val
        195                 200                 205
Gly Gly Asp Lys Leu Ile Ile Pro Phe Cys Ser Arg Ala Glu Ala Gln
    210                 215                 220
Asn Asp Pro Leu Leu Pro Gly Tyr Ser Phe Asn Ala His Leu Val Ala
225                 230                 235                 240
Gly Leu Thr Pro Ile Glu Ala Asn Gly Tyr Leu Asp Phe Phe Ile Asp
                245                 250                 255
Arg Pro Leu Gly Met Lys Gly Tyr Ile Leu Asn Leu Thr Ile Arg Gly
            260                 265                 270
Gln Gly Val Val Lys Asn Gln Gly Arg Glu Phe Val Cys Arg Pro Gly
        275                 280                 285
Asp Ile Leu Leu Phe Pro Pro Gly Glu Ile His His Tyr Gly Arg His
    290                 295                 300
Pro Glu Ala Arg Glu Trp Tyr His Gln Trp Val Tyr Phe Arg Pro Arg
305                 310                 315                 320
Ala Tyr Trp His Glu Trp Leu Asn Trp Pro Ser Ile Phe Ala Asn Thr
                325                 330                 335
Gly Phe Phe Arg Pro Asp Glu Ala His Gln Pro His Phe Ser Asp Leu
            340                 345                 350
Phe Gly Gln Ile Ile Asn Ala Gly Gln Gly Glu Gly Arg Tyr Ser Glu
        355                 360                 365
Leu Leu Ala Ile Asn Leu Leu Glu Gln Leu Leu Arg Arg Met Glu
    370                 375                 380
Ala Ile Asn Glu Ser Leu His Pro Pro Met Asp Asn Arg Val Arg Glu
385                 390                 395                 400
Ala Cys Gln Tyr Ile Ser Asp His Leu Ala Asp Ser Asn Phe Asp Ile
                405                 410                 415
Ala Ser Val Ala Gln His Val Cys Leu Ser Pro Ser Arg Leu Ser His
            420                 425                 430
Leu Phe Arg Gln Gln Leu Gly Ile Ser Val Leu Ser Trp Arg Glu Asp
        435                 440                 445
Gln Arg Ile Ser Gln Ala Lys Leu Leu Leu Ser Thr Thr Arg Met Pro
    450                 455                 460
Ile Ala Thr Val Gly Arg Asn Val Gly Phe Asp Asp Gln Leu Tyr Phe
465                 470                 475                 480
Ser Arg Val Phe Lys Lys Cys Thr Gly Ala Ser Pro Ser Glu Phe Arg
                485                 490                 495
Ala Gly Cys Glu Glu Lys Val Asn Asp Val Ala Val Lys Leu Ser Thr
```

```
            500                 505                 510
Ser Glu Asn Ile Asn Ala Asp Asp Thr Tyr Arg Ile Ile Asn Lys Ile
        515                 520                 525

Lys Ala Cys Arg Ser Asn Asn Asp Ile Asn Gln Cys Leu Ser Asp Met
        530                 535                 540

Thr Lys Met Val His Cys Glu Tyr Tyr Leu Ala Ile Ile Tyr Pro
545                 550                 555                 560

His Ser Met Val Lys Ser Asp Ile Ser Ile Leu Asp Asn Tyr Pro Lys
                565                 570                 575

Lys Trp Arg Gln Tyr Tyr Asp Asp Ala Asn Leu Ile Lys Tyr Asp Pro
            580                 585                 590

Ile Val Asp Tyr Ser Lys Ser Asn His Ser Pro Ile Asn Trp Asn Ile
        595                 600                 605

Phe Glu Asn Asn Ala Val Asn Lys Lys Ser Pro Asn Val Ile Lys Glu
        610                 615                 620

Ala Lys Thr Ser Gly Leu Ile Thr Gly Phe Ser Phe Pro Ile His Thr
625                 630                 635                 640

Ala Asn Asn Gly Phe Gly Met Leu Ser Phe Ala His Ser Glu Lys Asp
                645                 650                 655

Asn Tyr Ile Asp Ser Leu Phe Leu His Ala Cys Met Asn Ile Pro Leu
            660                 665                 670

Ile Val Pro Ser Leu Val Asp Asn Tyr Arg Lys Ile Asn Ile Ala Asn
        675                 680                 685

Asn Lys Ser Asn Asn Asp Leu Thr Lys Arg Glu Lys Glu Cys Leu Ala
        690                 695                 700

Trp Ala Cys Glu Gly Lys Ser Ser Trp Asp Ile Ser Lys Ile Leu Gly
705                 710                 715                 720

Cys Ser Glu Arg Thr Val Thr Phe His Leu Thr Asn Ala Gln Met Lys
                725                 730                 735

Leu Asn Thr Thr Asn Arg Cys Gln Ser Ile Ser Lys Ala Ile Leu Thr
            740                 745                 750

Gly Ala Ile Asp Trp Pro Tyr Phe Lys Asn Gly Ser His His His His
        755                 760                 765

His His
    770

<210> SEQ ID NO 17
<211> LENGTH: 376
<212> TYPE: PRT
<213> ORGANISM: Artificial Sequence
<220> FEATURE:
<223> OTHER INFORMATION: Full length amino acids sequence of ArsR-LuxR
    N86K and C245W

<400> SEQUENCE: 17

Met Ser Phe Leu Leu Pro Ile Gln Leu Phe Lys Ile Leu Ala Asp Glu
1               5                   10                  15

Thr Arg Leu Gly Ile Val Leu Leu Ser Glu Leu Gly Glu Leu Cys
            20                  25                  30

Val Cys Asp Leu Cys Thr Ala Leu Asp Gln Ser Gln Pro Lys Ile Ser
        35                  40                  45

Arg His Leu Ala Leu Leu Arg Glu Ser Gly Leu Leu Leu Asp Arg Lys
        50                  55                  60

Gln Gly Lys Trp Val His Tyr Arg Leu Ser Pro His Ile Pro Ala Trp
65              70                  75                  80
```

```
Ala Ala Lys Ile Ile Asp Glu Ala Trp Arg Cys Glu Gln Glu Lys Val
                85                  90                  95

Gln Ala Ile Val Arg Asn Leu Ala Arg Gln Asn Cys Ser Gly Asp Ser
            100                 105                 110

Lys Asn Ile Cys Ser Thr Ser Glu Asn Ile Asn Ala Asp Asp Thr Tyr
        115                 120                 125

Arg Ile Ile Asn Lys Ile Lys Ala Cys Arg Ser Asn Asn Asp Ile Asn
    130                 135                 140

Gln Cys Leu Ser Asp Met Thr Lys Met Val His Cys Glu Tyr Tyr Leu
145                 150                 155                 160

Leu Ala Ile Ile Tyr Pro His Ser Met Val Lys Ser Asp Ile Ser Ile
                165                 170                 175

Leu Asp Asn Tyr Pro Lys Lys Trp Arg Gln Tyr Tyr Asp Asp Ala Asn
            180                 185                 190

Leu Ile Lys Tyr Asp Pro Ile Val Asp Tyr Ser Lys Ser Asn His Ser
        195                 200                 205

Pro Ile Asn Trp Asn Ile Phe Glu Asn Asn Ala Val Asn Lys Lys Ser
    210                 215                 220

Pro Asn Val Ile Lys Glu Ala Lys Thr Ser Gly Leu Ile Thr Gly Phe
225                 230                 235                 240

Ser Phe Pro Ile His Thr Ala Asn Asn Gly Phe Gly Met Leu Ser Phe
                245                 250                 255

Ala His Ser Glu Lys Asp Asn Tyr Ile Asp Ser Leu Phe Leu His Ala
            260                 265                 270

Cys Met Asn Ile Pro Leu Ile Val Pro Ser Leu Val Asp Asn Tyr Arg
        275                 280                 285

Lys Ile Asn Ile Ala Asn Asn Lys Ser Asn Asn Asp Leu Thr Lys Arg
    290                 295                 300

Glu Lys Glu Cys Leu Ala Trp Ala Cys Glu Gly Lys Ser Ser Trp Asp
305                 310                 315                 320

Ile Ser Lys Ile Leu Gly Cys Ser Glu Arg Thr Val Thr Phe His Leu
                325                 330                 335

Thr Asn Ala Gln Met Lys Leu Asn Thr Thr Asn Arg Cys Gln Ser Ile
            340                 345                 350

Ser Lys Ala Ile Leu Thr Gly Ala Ile Asp Trp Pro Tyr Phe Lys Asn
        355                 360                 365

Gly Ser His His His His His His
        370                 375

<210> SEQ ID NO 18
<211> LENGTH: 40
<212> TYPE: DNA
<213> ORGANISM: Artificial Sequence
<220> FEATURE:
<223> OTHER INFORMATION: prpC-luxR -Fwd primer

<400> SEQUENCE: 18
gttatatctc ggaggtttac atgagcgaca caacgatcct                          40

<210> SEQ ID NO 19
<211> LENGTH: 40
<212> TYPE: DNA
<213> ORGANISM: Artificial Sequence
<220> FEATURE:
<223> OTHER INFORMATION: prpC-luxR -Rev primer

<400> SEQUENCE: 19
```
tcggcattta tgttttcact agtctggcgc ttatccagcg                          40

<210> SEQ ID NO 20
<211> LENGTH: 44
<212> TYPE: DNA
<213> ORGANISM: Artificial Sequence
<220> FEATURE:
<223> OTHER INFORMATION: prpD-luxR -Fwd primer

<400> SEQUENCE: 20
gttatatctc ggaggtttac atgtcagctc aaatcaacaa catc                     44

<210> SEQ ID NO 21
<211> LENGTH: 45
<212> TYPE: DNA
<213> ORGANISM: Artificial Sequence
<220> FEATURE:
<223> OTHER INFORMATION: prpD-luxR-Rev primer

<400> SEQUENCE: 21
tcggcattta tgttttcact agtaatgacg tacaggtcga gatac                    45

<210> SEQ ID NO 22
<211> LENGTH: 25
<212> TYPE: DNA
<213> ORGANISM: Artificial Sequence
<220> FEATURE:
<223> OTHER INFORMATION: mTagBFP Fwd primer

<400> SEQUENCE: 22
ccatttgatc gcaaatatca agacg                                          25

<210> SEQ ID NO 23
<211> LENGTH: 76
<212> TYPE: DNA
<213> ORGANISM: Artificial Sequence
<220> FEATURE:
<223> OTHER INFORMATION: pMCvec-Plux-ApaI PCR1 Rev primer

<400> SEQUENCE: 23
tttattcgac tataacaaac cattttcttg cgtaaacctg tacgatccta caggtggtac    60
ctataaacgc agaaag                                                    76

<210> SEQ ID NO 24
<211> LENGTH: 42
<212> TYPE: DNA
<213> ORGANISM: Artificial Sequence
<220> FEATURE:
<223> OTHER INFORMATION: pMCvec-Plux-ApaI PCR2 Rev primer

<400> SEQUENCE: 24
ttttgggccc tttattcgac tataacaaac cattttcttg cg                       42

<210> SEQ ID NO 25
<211> LENGTH: 53
<212> TYPE: DNA
<213> ORGANISM: Artificial Sequence
<220> FEATURE:
<223> OTHER INFORMATION: sfGFP standard RBS library Fwd (ApaI-XhoI)
      primer

<400> SEQUENCE: 25
ttttgggccc rmscyytawg gaggyctcga gatgggtct aaaggcgaag aac            53

<210> SEQ ID NO 26

```
<211> LENGTH: 34
<212> TYPE: DNA
<213> ORGANISM: Artificial Sequence
<220> FEATURE:
<223> OTHER INFORMATION: aph-HindIII Rev primer

<400> SEQUENCE: 26
ttttaagctt atcagaagaa ctcgtcaaga aggc                              34

<210> SEQ ID NO 27
<211> LENGTH: 25
<212> TYPE: DNA
<213> ORGANISM: Artificial Sequence
<220> FEATURE:
<223> OTHER INFORMATION: Fusion-ml-inv-Fwd primer

<400> SEQUENCE: 27
catcatcacc atcaccacta atgaa                                        25

<210> SEQ ID NO 28
<211> LENGTH: 25
<212> TYPE: DNA
<213> ORGANISM: Artificial Sequence
<220> FEATURE:
<223> OTHER INFORMATION: Fusion-ml-inv-Rev primer

<400> SEQUENCE: 28
gtaaacctcc gagatataac tagag                                        25

<210> SEQ ID NO 29
<211> LENGTH: 25
<212> TYPE: DNA
<213> ORGANISM: Artificial Sequence
<220> FEATURE:
<223> OTHER INFORMATION: Fusion-mutlibrary-Fwd primer

<400> SEQUENCE: 29
ctctagttat atctcggagg tttac                                        25

<210> SEQ ID NO 30
<211> LENGTH: 25
<212> TYPE: DNA
<213> ORGANISM: Artificial Sequence
<220> FEATURE:
<223> OTHER INFORMATION: Fusion-mutlibrary-Rev primer

<400> SEQUENCE: 30
ttcattagtg gtgatggtga tgatg                                        25

<210> SEQ ID NO 31
<211> LENGTH: 648
<212> TYPE: PRT
<213> ORGANISM: Artificial Sequence
<220> FEATURE:
<223> OTHER INFORMATION: Full length amino acids sequence of PrpCK318R-
      LuxRN86K and C245W

<400> SEQUENCE: 31

Met Ser Asp Thr Thr Ile Leu Gln Asn Ser Thr His Val Ile Lys Pro
1               5                   10                  15

Lys Lys Ser Val Ala Leu Ser Gly Val Pro Ala Gly Asn Thr Ala Leu
            20                  25                  30

Cys Thr Val Gly Lys Ser Gly Asn Asp Leu His Tyr Arg Gly Tyr Asp
        35                  40                  45

Ile Leu Asp Leu Ala Lys His Cys Glu Phe Glu Glu Val Ala His Leu
```

```
                50                  55                  60
Leu Ile His Gly Lys Leu Pro Thr Arg Asp Glu Leu Ala Ala Tyr Lys
 65                  70                  75                  80

Thr Lys Leu Lys Ala Leu Arg Gly Leu Pro Ala Asn Val Arg Thr Val
                 85                  90                  95

Leu Glu Ala Leu Pro Ala Ala Ser His Pro Met Asp Val Met Arg Thr
                100                 105                 110

Gly Val Ser Ala Leu Gly Cys Thr Leu Pro Lys Glu Gly His Thr
                115                 120                 125

Val Ser Gly Ala Arg Asp Ile Ala Asp Lys Leu Leu Ala Ser Leu Ser
                130                 135                 140

Ser Ile Leu Leu Tyr Trp Tyr His Tyr Ser His Asn Gly Glu Arg Ile
145                 150                 155                 160

Gln Pro Glu Thr Asp Asp Ser Ile Gly Gly His Phe Leu His Leu
                165                 170                 175

Leu His Gly Glu Lys Pro Ser Gln Ser Trp Glu Lys Ala Met His Ile
                180                 185                 190

Ser Leu Val Leu Tyr Ala Glu His Glu Phe Asn Ala Ser Thr Phe Thr
                195                 200                 205

Ser Arg Val Ile Ala Gly Thr Gly Ser Asp Met Tyr Ser Ala Ile Ile
210                 215                 220

Gly Ala Ile Gly Ala Leu Arg Gly Pro Lys His Gly Gly Ala Asn Glu
225                 230                 235                 240

Val Ser Leu Glu Ile Gln Gln Arg Tyr Glu Thr Pro Asp Glu Ala Glu
                245                 250                 255

Ala Asp Ile Arg Lys Arg Val Glu Asn Lys Glu Val Val Ile Gly Phe
                260                 265                 270

Gly His Pro Val Tyr Thr Ile Ala Asp Pro Arg His Gln Val Ile Lys
                275                 280                 285

Arg Val Ala Lys Gln Leu Ser Gln Glu Gly Gly Ser Leu Lys Met Tyr
290                 295                 300

Asn Ile Ala Asp Arg Leu Glu Thr Val Met Trp Glu Ser Arg Lys Met
305                 310                 315                 320

Phe Pro Asn Leu Asp Trp Phe Ser Ala Val Ser Tyr Asn Met Met Gly
                325                 330                 335

Val Pro Thr Glu Met Phe Thr Pro Leu Phe Val Ile Ala Arg Val Thr
                340                 345                 350

Gly Trp Ala Ala His Ile Ile Glu Gln Arg Gln Asp Asn Lys Ile Ile
                355                 360                 365

Arg Pro Ser Ala Asn Tyr Val Gly Pro Glu Asp Arg Pro Phe Val Ala
370                 375                 380

Leu Asp Lys Arg Gln Thr Ser Glu Asn Ile Ala Asp Asp Thr Tyr
385                 390                 395                 400

Arg Ile Ile Asn Lys Ile Lys Ala Cys Arg Ser Asn Asn Asp Ile Asn
                405                 410                 415

Gln Cys Leu Ser Asp Met Thr Lys Met Val His Cys Glu Tyr Tyr Leu
                420                 425                 430

Leu Ala Ile Ile Tyr Pro His Ser Met Val Lys Ser Asp Ile Ser Ile
                435                 440                 445

Leu Asp Asn Tyr Pro Lys Lys Trp Arg Gln Tyr Tyr Asp Asp Ala Asn
450                 455                 460

Leu Ile Lys Tyr Asp Pro Ile Val Asp Tyr Ser Lys Ser Asn His Ser
465                 470                 475                 480
```

```
Pro Ile Asn Trp Asn Ile Phe Glu Asn Asn Ala Val Asn Lys Lys Ser
                485                 490                 495

Pro Asn Val Ile Lys Glu Ala Lys Thr Ser Gly Leu Ile Thr Gly Phe
            500                 505                 510

Ser Phe Pro Ile His Thr Ala Asn Asn Gly Phe Gly Met Leu Ser Phe
        515                 520                 525

Ala His Ser Glu Lys Asp Asn Tyr Ile Asp Ser Leu Phe Leu His Ala
    530                 535                 540

Cys Met Asn Ile Pro Leu Ile Val Pro Ser Leu Val Asp Asn Tyr Arg
545                 550                 555                 560

Lys Ile Asn Ile Ala Asn Asn Lys Ser Asn Asn Asp Leu Thr Lys Arg
                565                 570                 575

Glu Lys Glu Cys Leu Ala Trp Ala Cys Glu Gly Lys Ser Ser Trp Asp
            580                 585                 590

Ile Ser Lys Ile Leu Gly Cys Ser Glu Arg Thr Val Thr Phe His Leu
        595                 600                 605

Thr Asn Ala Gln Met Lys Leu Asn Thr Thr Asn Arg Cys Gln Ser Ile
    610                 615                 620

Ser Lys Ala Ile Leu Thr Gly Ala Ile Asp Trp Pro Tyr Phe Lys Asn
625                 630                 635                 640

Gly Ser His His His His His His
                645

<210> SEQ ID NO 32
<211> LENGTH: 742
<212> TYPE: PRT
<213> ORGANISM: Artificial Sequence
<220> FEATURE:
<223> OTHER INFORMATION: Full length amino acids sequence of
      PrpDS163T-A225G-I285V-LuxRN86K and C245W

<400> SEQUENCE: 32

Met Ser Ala Gln Ile Asn Asn Ile Arg Pro Glu Phe Asp Arg Glu Ile
1               5                   10                  15

Val Asp Ile Val Asp Tyr Val Met Asn Tyr Glu Ile Ser Ser Lys Val
            20                  25                  30

Ala Tyr Asp Thr Ala His Tyr Cys Leu Leu Asp Thr Leu Gly Cys Gly
        35                  40                  45

Leu Glu Ala Leu Glu Tyr Pro Ala Cys Lys Lys Leu Leu Gly Pro Ile
    50                  55                  60

Val Pro Gly Thr Val Val Pro Asn Gly Val Arg Val Pro Gly Thr Gln
65                  70                  75                  80

Phe Gln Leu Asp Pro Val Gln Ala Ala Phe Asn Ile Gly Ala Met Ile
                85                  90                  95

Arg Trp Leu Asp Phe Asn Asp Thr Trp Leu Ala Ala Glu Trp Gly His
            100                 105                 110

Pro Ser Asp Asn Leu Gly Gly Ile Leu Ala Thr Ala Asp Trp Leu Ser
        115                 120                 125

Arg Asn Ala Val Ala Ser Gly Lys Ala Pro Leu Thr Met Lys Gln Val
    130                 135                 140

Leu Thr Ala Met Ile Lys Ala His Glu Ile Gln Gly Cys Ile Ala Leu
145                 150                 155                 160

Glu Asn Thr Phe Asn Arg Val Gly Leu Asp His Val Leu Leu Val Lys
                165                 170                 175

Val Ala Ser Thr Ala Val Val Ala Glu Met Leu Gly Leu Thr Arg Glu
```

-continued

```
               180                 185                 190
Glu Ile Leu Asn Ala Val Ser Leu Ala Trp Val Asp Gly Gln Ser Leu
            195                 200                 205
Arg Thr Tyr Arg His Ala Pro Asn Thr Gly Thr Arg Lys Ser Trp Ala
210                 215                 220
Gly Gly Asp Ala Thr Ser Arg Ala Val Arg Leu Ala Leu Met Ala Lys
225                 230                 235                 240
Thr Gly Glu Met Gly Tyr Pro Ser Ala Leu Thr Ala Pro Val Trp Gly
            245                 250                 255
Phe Tyr Asp Val Ser Phe Lys Gly Glu Ser Phe Arg Phe Gln Arg Pro
            260                 265                 270
Tyr Gly Ser Tyr Val Met Glu Asn Val Leu Phe Lys Val Ser Phe Pro
            275                 280                 285
Ala Glu Phe His Ser Gln Thr Ala Val Glu Ala Ala Met Thr Leu Tyr
            290                 295                 300
Glu Gln Met Gln Ala Ala Gly Lys Thr Ala Ala Asp Ile Glu Lys Val
305                 310                 315                 320
Thr Ile Arg Thr His Glu Ala Cys Ile Arg Ile Asp Lys Lys Gly
            325                 330                 335
Pro Leu Asn Asn Pro Ala Asp Arg Asp His Cys Ile Gln Tyr Met Val
            340                 345                 350
Ala Ile Pro Leu Leu Phe Gly Arg Leu Thr Ala Ala Asp Tyr Glu Asp
            355                 360                 365
Asn Val Ala Gln Asp Lys Arg Ile Asp Ala Leu Arg Glu Lys Ile Asn
            370                 375                 380
Cys Phe Glu Asp Pro Ala Phe Thr Ala Asp Tyr His Asp Pro Glu Lys
385                 390                 395                 400
Arg Ala Ile Ala Asn Ala Ile Thr Leu Glu Phe Thr Asp Gly Thr Arg
            405                 410                 415
Phe Glu Glu Val Val Val Glu Tyr Pro Ile Gly His Ala Arg Arg Arg
            420                 425                 430
Gln Asp Gly Ile Pro Lys Leu Val Asp Lys Phe Lys Ile Asn Leu Ala
            435                 440                 445
Arg Gln Phe Pro Thr Arg Gln Gln Arg Ile Leu Glu Val Ser Leu
450                 455                 460
Asp Arg Ala Arg Leu Glu Gln Met Pro Val Asn Glu Tyr Leu Asp Leu
465                 470                 475                 480
Tyr Val Ile Thr Ser Glu Asn Ile Asn Ala Asp Asp Thr Tyr Arg Ile
            485                 490                 495
Ile Asn Lys Ile Lys Ala Cys Arg Ser Asn Asn Asp Ile Asn Gln Cys
            500                 505                 510
Leu Ser Asp Met Thr Lys Met Val His Cys Glu Tyr Tyr Leu Leu Ala
            515                 520                 525
Ile Ile Tyr Pro His Ser Met Val Lys Ser Asp Ile Ser Ile Leu Asp
            530                 535                 540
Asn Tyr Pro Lys Lys Trp Arg Gln Tyr Tyr Asp Asp Ala Asn Leu Ile
545                 550                 555                 560
Lys Tyr Asp Pro Ile Val Asp Tyr Ser Lys Ser Asn His Ser Pro Ile
            565                 570                 575
Asn Trp Asn Ile Phe Glu Asn Asn Ala Val Asn Lys Lys Ser Pro Asn
            580                 585                 590
Val Ile Lys Glu Ala Lys Thr Ser Gly Leu Ile Thr Gly Phe Ser Phe
            595                 600                 605
```

-continued

```
Pro Ile His Thr Ala Asn Asn Gly Phe Gly Met Leu Ser Phe Ala His
    610                 615                 620

Ser Glu Lys Asp Asn Tyr Ile Asp Ser Leu Phe Leu His Ala Cys Met
625                 630                 635                 640

Asn Ile Pro Leu Ile Val Pro Ser Leu Val Asp Asn Tyr Arg Lys Ile
                645                 650                 655

Asn Ile Ala Asn Asn Lys Ser Asn Asn Asp Leu Thr Lys Arg Glu Lys
            660                 665                 670

Glu Cys Leu Ala Trp Ala Cys Glu Gly Lys Ser Ser Trp Asp Ile Ser
        675                 680                 685

Lys Ile Leu Gly Cys Ser Glu Arg Thr Val Thr Phe His Leu Thr Asn
    690                 695                 700

Ala Gln Met Lys Leu Asn Thr Thr Asn Arg Cys Gln Ser Ile Ser Lys
705                 710                 715                 720

Ala Ile Leu Thr Gly Ala Ile Asp Trp Pro Tyr Phe Lys Asn Gly Ser
                725                 730                 735

His His His His His His
            740
```

MULTI-INPUT/MULTI-OUTPUT GENE SWITCH, AND METHOD FOR PRODUCING SAME

The present application is a National Stage Application of PCT/JP2019/012285, filed Mar. 23, 2019, which claims priority from Japanese Patent Application No. 2018-057314, which is incorporated herein by reference.

TECHNICAL FIELD

The present invention relates to a production method for a multi-input/multi-output-type genetic switch or a transcription factor for forming the switch, and a multi-input/multi-output-type genetic switch or a transcription factor for forming the switch obtained by the production method, and to a fusion mutant.

The present application claims priority from Japanese Patent Application No. 2018-057314, which is incorporated herein by reference.

BACKGROUND ART (Current Situation of Biosensors)

If an intracellular concentration of an arbitrary substance, such as a metabolite or an environmental monitoring substance, can be assayed in a real-time manner, a great contribution can be made to progress of life science. However, it is difficult to adjust performance (sensitivity) of the substance as a sensor.

(Conventional Biosensor Configuration)

At present, a configuration of a biosensor is mainly based on the following operation principle.

A "gene induction-type" sensor has a reporter, such as a fluorescent protein, arranged downstream of a transcriptional control mechanism configured to be turned on/off using its target compound as an inducer. Transcription factors that respond to various molecules exist in nature, but sensor motifs for a vast majority of metabolites are not known. Further, even when an applicable sensor motif is found, in most cases, the sensor motif does not have practical performance in consideration of its response concentration, S/N ratio, and output intensity.

With regard to a FRET sensor, when a sensor motif that undergoes a great structural change as a result of binding to a target molecule is found, a sensor utilizing fluorescence resonance energy transfer (FRET) can be constructed. However, there is a problem in that rational design for the structural change is extremely difficult.

RELATED ART

The inventors of the present invention have disclosed "a selection method for a genetic switch and a genetic circuit, including using, as a selector, an expression vector containing at least a gene sequence encoding a thymidine kinase, preferably a human herpes virus derived thymidine kinase, and a promoter sequence operably linked to the gene sequence upstream thereof (see Patent Literature 1)."

However, the above-mentioned selection method for a genetic circuit has a different principle from that of a production method for a multi-input/multi-output-type genetic switch or a transcription factor for forming the switch of the present invention.

The inventors of the present invention have made the following disclosure: "The inventors of the present invention have found that ON selection can be conducted within a short time period by: using, as a selector, an expression vector designed so that alkyladenine DNA glycosidase (AAG) as an alkylated DNA repair enzyme can be operated on the output side, i.e., downstream of a genetic circuit; operating the genetic switch in cells transfected with the expression vector and an expression vector expressing the genetic circuit under such conditions that cell death due to DNA alkylation is induced; and collecting viable cells. In addition, by employing the ON selection method in combination with the OFF selection method previously developed by the inventors of the present invention, i.e., the OFF selection method involving using, as a selector, an expression vector designed so that hsvTK can be operated on the output side of a genetic circuit, the inventors of the present invention have found a selection method for a genetic switch and a genetic circuit by which ON selection and OFF selection can both be conducted within short time periods of about 5 to 30 minutes. (see Patent Literature 2)."

However, the above-mentioned selection method for a genetic circuit has a different principle from that of the production method for a multi-input/multi-output-type genetic switch or a transcription factor for forming the switch of the present invention.

The inventors of the present invention have disclosed "a nucleic acid construct to be used for modifying a genome in a cell, the nucleic acid construct containing a gene sequence encoding a nucleoside kinase, preferably a thymidine kinase, as a gene sequence for selecting a cell whose genome has been modified with the nucleic acid construct, and a modification method for a genome in a cell including using the nucleic acid construct (see Patent Literature 3)."

However, the above-mentioned selection method for a genetic circuit has a different principle from that of the production method for a multi-input/multi-output-type genetic switch or a transcription factor for forming the switch of the present invention.

CITATION LIST

Patent Literature

[PTL 1] JP 2011-125333 A
[PTL 2] WO 2012/060407 A1
[PTL 3] JP 2013-17473 A

SUMMARY OF INVENTION

Technical Problem

If a function of judging (computing) by integrating a larger amount of input information in one sensor protein can be imparted, it is even possible to develop a "sensitivity variable type" "conditional" sensor that is externally controllable in terms of sensitivity and the presence or absence of a response through use of another element. However, there has been no method of producing such sensor protein.

The present invention is directed to the provision of a production method for a multi-input/multi-output-type genetic switch or transcription factor that is a genetic switch required for the above-mentioned sensor or a transcription factor for forming the switch, and such multi-input/multi-output-type genetic switch or transcription factor for forming the switch.

Solution to Problem

The inventors of the present invention have made extensive investigations, and as a result, have completed a production method for a multi-input/multi-output-type genetic switch or a transcription factor, essentially including the steps of "fusing two or more transcription factor genes to each other or one or more transcription factors and one or more binders to each other" and "introducing mutations into the fusion-type transcription factor gene," and have further succeeded in obtaining a multi-input/multi-output-type genetic switch or a transcription factor by the method. Thus, the inventors have completed the present invention.

That is, the present invention is as described below.

1. A production method for a multi-input/multi-output-type genetic switch or a transcription factor for forming the switch, the method including one of (A) or (B), the method (A) including the following steps of (1) to (3):

(A)

(1) a step of introducing, into cells, or adding, to a cell-free protein synthesis system, a library of nucleic acids of fusion mutants of a binder $B_1$ or a transcription factor $T_1$, which responds to a ligand $L_1$, and a binder $B_2$ or a transcription factor $T_2$, which responds to a ligand $L_2$, the library being obtained by introducing mutations into a genetic construct carrying a gene sequence encoding the binder $B_1$ or the transcription factor $T_1$ and a gene sequence encoding the binder $B_2$ or the transcription factor $T_2$, and a reporter expression vector carrying a gene sequence encoding a promoter P1 to be controlled by the transcription factor $T_1$ and/or a gene sequence encoding a promoter $P_2$ to be controlled by the transcription factor $T_2$, and a gene sequence encoding a reporter Rx functionally linked to the promoter sequence $P_1$ and/or the promoter sequence $P_2$, where X represents an integer of 1 or more;

(2) a step of adding the ligand $L_1$ and/or the ligand $L_2$ to the cells or the cell-free protein synthesis system of (1); and (3) a step of selecting one of the fusion mutants of the binder $B_1$ or the transcription factor $T_1$ and the binder $B_1$ or the transcription factor $T_2$ as a genetic switch or a transcription factor for forming the switch through use of an expression amount of the reporter as an indicator, or the method (B) including the following steps of (1) to (3):

(B)

(1) a step of introducing, into cells, or adding, to a cell-free protein synthesis system, a library of nucleic acids of fusion mutants of a binder $B_1$ or a transcription factor $T_1$, which responds to a ligand $L_1$, a binder $B_2$ or a transcription factor $T_2$, which responds to a ligand $L_2$, and a binder $B_N$ or a transcription factor TN, which responds to a ligand $L_N$, the library being obtained by introducing mutations into a genetic construct carrying a gene sequence encoding the binder $B_1$ or the transcription factor $T_1$, a gene sequence encoding the binder $B_2$ or the transcription factor $T_2$, and a gene sequence encoding the binder $B_N$ or the transcription factor TN, and a reporter expression vector carrying a gene sequence encoding a promoter $P_1$ to be controlled by the transcription factor $T_1$, a gene sequence encoding a promoter $P_2$ to be controlled by the transcription factor $T_2$, and/or a gene sequence encoding a promoter $P_N$ to be controlled by the transcription factor $T_N$, and a gene sequence encoding a reporter Rx functionally linked to the promoter sequence $P_1$, the promoter sequence $P_2$, and/or the promoter sequence $P_N$, where N represents an integer of 3 or more;

(2) a step of introducing the ligand $L_1$, the ligand $L_2$, and/or the ligand $L_N$ into the cells or the cell-free protein synthesis system of (1); and (3) a step of selecting one of the fusion mutants of the binder $B_1$ or the transcription factor $T_1$, the binder $B_2$ or the transcription factor $T_2$, and the binder $B_N$ or the transcription factor $T_N$ as a genetic switch or a transcription factor for forming the switch through use of an expression amount of the reporter as an indicator.

2. The method according to the above-mentioned item 1, wherein in the method (A), the step of selecting includes selecting a fusion mutant having a high ratio of an expression amount of the reporter obtained by introduction of the ligand $L_1$ and the ligand $L_2$ to an expression amount of the reporter obtained by introduction of the ligand $L_1$ or the ligand $L_2$ as a genetic switch having a 2-input/AND-type output sensor function or a transcription factor for forming the switch.

3. The method according to the above-mentioned item 1, wherein in the method (A), when the promoter $P_2$ to be controlled by the transcription factor $T_2$ is used, the step of selecting includes selecting a fusion mutant having a high ratio of an expression amount of the reporter obtained by introduction of the ligand $L_1$ and the ligand $L_2$ to an expression amount of the reporter obtained by introduction of the ligand $L_2$ as a genetic switch having a 2-input/AND-type output sensor function or a transcription factor for forming the switch, or when the promoter $P_1$ to be controlled by the transcription factor $T_1$ is used, the step of selecting includes selecting a fusion mutant having a high ratio of an expression amount of the reporter obtained by introduction of the ligand $L_1$ and the ligand $L_2$ to an expression amount of the reporter obtained by introduction of the ligand $L_1$ as a genetic switch having a 2-input/AND-type output sensor function or a transcription factor for forming the switch.

4. The method according to the above-mentioned item 1, wherein in the method (A), when the promoter $P_1$ to be controlled by the transcription factor $T_1$ is used, the step of selecting includes selecting a fusion mutant having a high ratio of an expression amount of the reporter obtained by introduction of the ligand $L_2$ to an expression amount of the reporter obtained without any ligand as a genetic switch having a 2-input/OR-type sensor function or a transcription factor for forming the switch, or when the promoter $P_2$ to be controlled by the transcription factor $T_2$ is used, the step of selecting includes selecting a fusion mutant having a high ratio of an expression amount of the reporter obtained by introduction of the ligand $L_1$ to an expression amount of the reporter obtained without any ligand as a genetic switch having a 2-input/OR-type sensor function or a transcription factor for forming the switch.

5. The method according to the above-mentioned item 1, wherein in the method (A), when the promoter $P_1$ to be controlled by the transcription factor $T_1$ is used, the step of selecting includes selecting a fusion mutant having a high ratio of an expression amount of the reporter obtained by introduction of the ligand $L_1$ to an expression amount of the reporter obtained by introduction of the ligand $L_2$ as a genetic switch for an output-type sensor that specifically responds to the ligand $L_1$ or a transcription factor for forming the switch, or when the promoter $P_2$ to be controlled by the transcription factor $T_2$ is used, the step of selecting includes selecting a fusion mutant having a high ratio of an expression amount of the reporter obtained by introduction of the ligand $L_2$ to an expression amount of the reporter obtained by introduction of the ligand $L_1$ as a genetic switch for an output-type sensor that specifically responds to the ligand $L_2$ or a transcription factor for forming the switch.

6. The method according to the above-mentioned item 1, wherein in the method (A), when the promoter $P_1$ to be controlled by the transcription factor $T_1$ is used, the step of selecting includes selecting a fusion mutant having a high ratio of an expression amount of the reporter obtained without any ligand to an expression amount of the reporter obtained by introduction of the ligand $L_1$, and having a high ratio of the expression amount of the reporter obtained without any ligand to an expression amount of the reporter obtained by introduction of the ligand $L_2$ as a genetic switch having a NOR-type sensor function or a transcription factor for forming the switch.

7. The method according to the above-mentioned item 1, wherein in the method (A), when the promoter $P_1$ to be controlled by the transcription factor $T_1$ is used, the step of selecting includes selecting a fusion mutant having a high ratio of an expression amount of the reporter obtained without any ligand or obtained by introduction of one of the ligand $L_1$ or the ligand $L_2$ to an expression amount of the reporter obtained by introduction of the ligand $L_1$ and the ligand $L_2$ as a genetic switch having a NAND-type sensor function or a transcription factor for forming the switch.

8. The method according to the above-mentioned item 1, wherein in the method (A), the step of selecting includes selecting a fusion mutant in which both of an expression amount of the reporter obtained by introduction of the ligand $L_1$ and an expression amount of the reporter obtained by introduction of the ligand $L_2$ are decreased as a genetic switch having a function as a 2-input/3-stage output reduction-type sensor or a transcription factor for forming the switch.

9. The method according to the above-mentioned item 1, wherein in the method (A), the step of selecting includes selecting a fusion mutant in which both of an expression amount of the reporter obtained by introduction of the ligand $L_1$ and an expression amount of the reporter obtained by introduction of the ligand $L_2$ are increased as a genetic switch having a function as a 2-input/3-stage output increase-type sensor or a transcription factor for forming the switch.

10. The method according to the above-mentioned item 1, wherein in the method (B),
N=3, and
the step of selecting includes selecting a fusion mutant in which an expression amount of the reporter obtained by introduction of the ligand $L_1$, an expression amount of the reporter obtained by introduction of the ligand $L_2$, and an expression amount of the reporter obtained by introduction of a ligand $L_3$ are decreased as a genetic switch having a function as a 3-input/4-stage output reduction-type sensor or a transcription factor for forming the switch.

11. The method according to the above-mentioned item 1, wherein in the method (B),
N=3, and
the step of selecting includes selecting a fusion mutant in which an expression amount of the reporter obtained by introduction of the ligand $L_1$, an expression amount of the reporter obtained by introduction of the ligand $L_2$, and an expression amount of the reporter obtained by introduction of a ligand $L_3$ are increased as a genetic switch having a function as a 3-input/4-stage output increase-type sensor or a transcription factor for forming the switch.

12. The method according to the above-mentioned item 1, wherein in the method (B),
N=3,
the promoter $P_1$ to be controlled by the transcription factor $T_1$, a reporter $R_1$ functionally linked to the promoter sequence $P_1$, the promoter $P_2$ to be controlled by the transcription factor $T_2$, a reporter $R_2$ functionally linked to the promoter sequence $P_2$, a promoter $P_3$ to be controlled by a transcription factor $T_3$, and a reporter $R_3$ functionally linked to a promoter sequence $P_3$ are used,
a library of nucleic acids of fusion mutants of a ligand $L_1$ binding-type transcription factor $T_1$ lacking a ligand binding ability as a result of mutation introduction, the binder $B_2$ or the transcription factor $T_2$, and a binder $B_3$ or the transcription factor $T_3$ is used, and
the step of selecting includes selecting a fusion mutant in which an expression amount of the reporter obtained by introduction of the ligand $L_1$ and an expression amount of the reporter obtained by introduction of the ligand $L_2$ are prevented from being increased, in which an expression amount of the reporter obtained by introduction of a ligand $L_3$ is increased, and which expresses the reporter $R_1$, the reporter $R_2$, and the reporter $R_3$ as a genetic switch for a multi-output-type sensor that specifically responds to the ligand $L_3$ or a transcription factor for forming the switch.

13. The method according to the above-mentioned item 1, wherein in the method (B),
N=3,
the promoter $P_1$ to be controlled by the transcription factor $T_1$, a reporter $R_1$ functionally linked to the promoter sequence $P_1$, the promoter $P_2$ to be controlled by the transcription factor $T_2$, a reporter $R_2$ functionally linked to the promoter sequence $P_2$, a promoter $P_3$ to be controlled by a transcription factor $T_3$, and a reporter $R_3$ functionally linked to a promoter sequence $P_3$ are used,
a library of nucleic acids of fusion mutants of the binder $B_1$ or the transcription factor $T_1$ lacking a ligand binding ability as a result of mutation introduction, the binder $B_2$ or the transcription factor $T_2$ lacking a ligand binding ability as a result of mutation introduction, and a binder $B_3$ or the transcription factor $T_3$ is used, and
the step of selecting includes selecting a fusion mutant in which an expression amount of the reporter obtained by introduction of the ligand $L_2$ and an expression amount of the reporter obtained by introduction of a ligand $L_3$ are increased, in which an expression amount of the reporter obtained by introduction of the ligand $L_1$ is prevented from being increased, and which expresses the reporter $R_2$ as a genetic switch for a multi-output-type sensor that specifically responds to the ligand $L_2$ and the ligand $L_3$ or a transcription factor for forming the switch.

14. The method according to any one of the above-mentioned items 1 to 13, wherein the binder $B_1$, the binder $B_2$, the binder $B_3$, and the binder $B_N$ are each selected from a transcription factor, an enzyme, an antibody, a histone, a chaperone, or a ribosome.

15. The method according to any one of the above-mentioned items 1 to 13, wherein the binder $B_1$, the binder $B_2$, the binder $B_3$, and the binder $B_N$ are each a transcription factor or an enzyme.

16. A production method for a genetic switch for detection of a ligand L1 or a transcription factor for forming the switch, the production method including the following steps of (1) to (3):

(1) a step of introducing, into cells, or adding, to a cell-free protein synthesis system, a library of nucleic acids of fusion mutants of a binder B1 or a transcription factor T1, which responds to a ligand L1, and a transcription factor T2, the library being obtained by introducing mutations into a genetic construct carrying a gene sequence encoding the binder B1 or the transcription factor T1 and a gene sequence encoding the transcription factor T2, and an expression vector carrying a gene sequence encoding a promoter P2 to be controlled by the transcription factor T2 and a gene sequence encoding a reporter Rx functionally linked to the promoter P2, where X represents an integer of 1 or more;

(2) a step of adding the ligand L1 and/or the ligand L2 to the cells or the cell-free protein synthesis system of (1); and (3) a step of selecting a fusion mutant having a high ratio of an expression amount of the reporter obtained by introduction of the ligand L1 and the ligand L2 to an expression amount of the reporter obtained by introduction of the ligand L2 or a fusion mutant having a high ratio of an expression amount of the reporter obtained by introduction of the ligand L1 to an expression amount of the reporter obtained by introduction of the ligand L2 as a genetic switch for detection of the ligand L1 or a transcription factor for forming the switch.

17. The production method according to the above-mentioned item 16, wherein the ligand $L_1$ is arsenic.

18. A production method for a transcription factor capable of enhancing expression of a promoter P2 to be controlled by a transcription factor T2 through use of a ligand L1, the production method including the following steps of (1) to (3):

(1) a step of introducing, into cells, or adding, to a cell-free protein synthesis system, a library of nucleic acids of fusion mutants of a binder $B_1$ or a transcription factor $T_1$, which responds to the ligand $L_1$, and a binder $B_2$ or the transcription factor $T_2$, which responds to a ligand $L_2$, the library being obtained by introducing mutations into a genetic construct carrying a gene sequence encoding the binder $B_1$ or the transcription factor $T_1$ and a gene sequence encoding the binder $B_2$ or the transcription factor $T_2$, and a reporter expression vector carrying a gene sequence encoding the promoter $P_2$ to be controlled by the transcription factor $T_2$ and a gene sequence encoding a reporter Rx functionally linked to the promoter $P_2$, where X represents an integer of 1 or more;

(2) a step of adding the ligand $L_1$ and/or the ligand $L_2$ to the cells or the cell-free protein synthesis system of (1); and (3) a step of selecting a fusion mutant having a high ratio of an expression amount of the reporter obtained by introduction of the ligand $L_1$ to an expression amount of the reporter obtained by introduction of the ligand $L_2$ as a transcription factor capable of enhancing expression of the promoter $P_2$ to be controlled by the transcription factor $T_2$ through use of the ligand $L_1$.

19. A genetic switch or a transcription factor for forming the switch, which is obtained by the production method of at least one of the above-mentioned items 1 to 18.

20. A gene fusion mutant, which is obtained by the production method of at least one of the above-mentioned items 1 to 15, wherein the gene fusion mutant is capable of enhancing or repressing expression of the promoter P1, the promoter P2, and/or the promoter Pn to be controlled by T1, T2, and/or Tn through use of the ligand L1, the ligand L2, and/or the ligand LN.

21. The gene fusion mutant according to the above-mentioned item 20, wherein the gene fusion mutant is any one of the following (1) to (9):

(1) a gene fusion mutant capable of enhancing expression of the promoter P2 to be controlled by the transcription factor T2 through use of the ligand L1;

(2) a gene fusion mutant capable of decreasing expression of the promoter P2 to be controlled by the transcription factor T2 through use of the ligand L1;

(3) a gene fusion mutant capable of enhancing or repressing expression of the promoters P1, P2, and Pn to be controlled by the transcription factor T1, the transcription factor T2, and the transcription factor Tn through use of the ligand L1;

(4) a gene fusion mutant capable of enhancing or repressing expression of the promoters P2 and Pn to be controlled by the transcription factor T2 and the transcription factor Tn through use of the ligand L1;

(5) a gene fusion mutant capable of enhancing or repressing expression of the promoters P1, P2, and Pn to be controlled by the transcription factor T1, the transcription factor T2, and the transcription factor Tn through use of the ligands L1 and L2;

(6) a gene fusion mutant capable of enhancing or repressing expression of the promoters P2 and Pn to be controlled by the transcription factor T2 and the transcription factor Tn through use of the ligands L1 and L2;

(7) a gene fusion mutant capable of enhancing expression of the promoters P1, P2, and Pn to be controlled by T1, T2, and Tn through use of the ligands L1, L2, and LN;

(8) a gene fusion mutant capable of repressing expression of the promoters P1, P2, and Pn to be controlled by T1, T2, and Tn through use of the ligands L1, L2, and LN; and (9) a gene fusion mutant in which, through use of the ligand $L_1$, expression of the promoter P1 to be controlled by the transcription factor $T_1$ is repressed, expression of the promoter $P_2$ to be controlled by the transcription factor $T_2$ is enhanced, and expression of the promoter $P_3$ to be controlled by the transcription factor $T_3$ is enhanced.

22. A method of using a genetic switch or a transcription factor for forming the switch obtained by the production method of at least one of the above-mentioned items 1 to 18, or the genetic switch or the transcription factor for forming the switch of the above-mentioned item 19 as a sensor for detection of the ligand $L_1$, the ligand $L_2$, and/or the ligand $L_N$, protein synthesis, induction of protein secretion, induction of a biosynthetic pathway, regulation of a flow rate of a biosynthetic pathway, induction of cell proliferation, induction of a physiological function, or a control mechanism for a physiological function.

23. A method of using a genetic switch or a transcription factor for forming the switch obtained by the production method of at least one of the above-mentioned items 1 to 18, or the genetic switch or the transcription factor for forming the switch of the above-mentioned item 19 as a sensor for detection of the ligand $L_1$, the ligand $L_2$, and/or the ligand $L_N$, the production method including the following steps (1) to (6) of adjusting detection sensitivity of the ligand $L_1$, the ligand $L_2$, and/or the ligand $L_N$:

(1) when response sensitivity to the ligand $L_1$ is to be increased, an addition concentration of the ligand $L_2$ and/or the ligand $L_N$ is increased;

(2) when response sensitivity to the ligand $L_1$ is to be decreased, an addition concentration of the ligand $L_2$ and/or the ligand $L_N$ is decreased;

(3) when response sensitivity to the ligand $L_2$ is to be increased, an addition concentration of the ligand $L_1$ and/or the ligand $L_N$ is increased;

(4) when response sensitivity to the ligand $L_2$ is to be decreased, an addition concentration of the ligand $L_1$ and/or the ligand $L_N$ is decreased;

(5) when response sensitivity to the ligand $L_N$ is to be increased, an addition concentration of the ligand $L_1$ and/or the ligand $L_2$ is increased; and (6) when response sensitivity to the ligand $L_N$ is to be decreased, an addition concentration of the ligand $L_1$ and/or the ligand $L_2$ is decreased.

24. (A) A genetic switch, including a fusion mutant of a binder $B_1$ or a transcription factor $T_1$, which responds to a ligand $L_1$, and a binder $B_2$ or a transcription factor $T_2$, which responds to a ligand $L_2$, the fusion mutant being obtained by introducing a mutation into a genetic construct carrying a gene sequence encoding the binder $B_1$ or the transcription factor $T_1$ and a gene sequence encoding the binder $B_2$ or the transcription factor $T_2$, or (B) a genetic switch, including a fusion mutant of a binder $B_1$ or a transcription factor $T_1$, which responds to a ligand $L_1$, a binder $B_2$ or a transcription factor $T_2$, which responds to a ligand $L_2$, and a binder $B_N$ or a transcription factor $T_N$, which responds to a ligand $L_N$, the fusion mutant being obtained by introducing a mutation into a genetic construct carrying a gene sequence encoding the binder $B_1$ or the transcription factor $T_1$, a gene sequence encoding the binder $B_2$ or the transcription factor $T_2$, and a gene sequence encoding the binder $B_N$ or the transcription factor $T_N$.

25. The genetic switch according to the above-mentioned item 24, wherein in the (A), the genetic switch has a high ratio of an expression amount of a reporter obtained by introduction of the ligand $L_1$ and the ligand $L_2$ to an expression amount of the reporter obtained by introduction of the ligand $L_1$ or the ligand $L_2$ and has a 2-input/AND-type output sensor function.

26. The genetic switch according to the above-mentioned item 24, wherein in the (A), when a promoter $P_2$ to be controlled by the transcription factor $T_2$ is used, the genetic switch has a high ratio of an expression amount of a reporter obtained by introduction of the ligand $L_1$ and the ligand $L_2$ to an expression amount of the reporter obtained by introduction of the ligand $L_2$ and has a 2-input/AND-type output sensor function, or when a promoter $P_1$ to be controlled by the transcription factor $T_1$ is used, the genetic switch has a high ratio of an expression amount of a reporter obtained by introduction of the ligand $L_1$ and the ligand $L_2$ to an expression amount of the reporter obtained by introduction of the ligand $L_1$ and has a 2-input/AND-type output sensor function.

27. The genetic switch according to the above-mentioned item 24, wherein in the (A), when a promoter $P_1$ to be controlled by the transcription factor $T_1$ is used, the genetic switch has a high ratio of an expression amount of a reporter obtained by introduction of the ligand $L_2$ to an expression amount of the reporter obtained without any ligand and has a 2-input/OR-type sensor function, or when a promoter $P_2$ to be controlled by the transcription factor $T_2$ is used, the genetic switch has a high ratio of an expression amount of a reporter obtained by introduction of the ligand $L_1$ to an expression amount of the reporter obtained without any ligand and has a 2-input/OR-type sensor function.

28. The genetic switch according to the above-mentioned item 24, wherein in the (A), when a promoter $P_1$ to be controlled by the transcription factor $T_1$ is used, the genetic switch has a high ratio of an expression amount of a reporter obtained by introduction of the ligand $L_1$ to an expression amount of the reporter obtained by introduction of the ligand $L_2$ and has a function of an output-type sensor that specifically responds to the ligand $L_1$, or when a promoter $P_2$ to be controlled by the transcription factor $T_2$ is used, the genetic switch has a high ratio of an expression amount of a reporter obtained by introduction of the ligand $L_2$ to an expression amount of the reporter obtained by introduction of the ligand $L_1$ and has a function of an output-type sensor that specifically responds to the ligand $L_2$.

29. The genetic switch according to the above-mentioned item 24, wherein in the (A), when a promoter $P_1$ to be controlled by the transcription factor $T_1$ is used, the genetic switch has a high ratio of an expression amount of a reporter obtained without any ligand to an expression amount of the reporter obtained by introduction of the ligand $L_1$, has a high ratio of the expression amount of the reporter obtained without any ligand to an expression amount of the reporter obtained by introduction of the ligand $L_2$, and has a NOR-type sensor function.

30. The genetic switch according to the above-mentioned item 24, wherein in the (A), when a promoter $P_1$ to be controlled by the transcription factor $T_1$ is used, the genetic switch has a high ratio of an expression amount of a reporter obtained without any ligand or obtained by introduction of one of the ligand $L_1$ or the ligand $L_2$ to an expression amount of the reporter obtained by introduction of the ligand $L_1$ and the ligand $L_2$ and has a NAND-type sensor function.

31. The genetic switch according to the above-mentioned item 24, wherein in the (A), the genetic switch decreases both of an expression amount of a reporter obtained by introduction of the ligand $L_1$ and an expression amount of the reporter obtained by introduction of the ligand $L_2$ and has a function as a 2-input/3-stage output reduction-type sensor.

32. The genetic switch according to the above-mentioned item 24, wherein in the (A), the genetic switch increases both of an expression amount of a reporter obtained by introduction of the ligand $L_1$ and an expression amount of the reporter obtained by introduction of the ligand $L_2$ and has a function as a 2-input/3-stage output increase-type sensor.

33. The genetic switch according to the above-mentioned item 24, wherein in the (B), N=3, and the genetic switch decreases an expression amount of a reporter obtained by introduction of the ligand $L_1$, an expression amount of the reporter obtained by introduction of the ligand $L_2$, and an expression amount of the reporter obtained by introduction of a ligand $L_3$ and has a function as a 3-input/4-stage output reduction-type sensor.

34. The genetic switch according to the above-mentioned item 24, wherein in the (B), N=3, and the genetic switch increases an expression amount of a reporter obtained by introduction of the ligand $L_1$, an expression amount of the reporter obtained by introduction of the ligand $L_2$, and an expression amount of the reporter obtained by introduction of a ligand $L_3$ and has a function as a 3-input/4-stage output increase-type sensor.

35. The genetic switch according to the above-mentioned item 24, wherein in the (B), N=3, and the genetic switch is prevented from increasing an expression amount of a reporter obtained by introduction of the ligand $L_1$ and an expression amount of the reporter obtained by introduction of the ligand $L_2$, increases an expression amount of the reporter obtained by introduction of a ligand $L_3$, expresses a reporter $R_1$, a reporter $R_2$, and a reporter $R_3$, and has a function as a multi-output-type sensor that specifically responds to the ligand $L_3$.

36. The genetic switch according to the above-mentioned item 24, wherein in the (B), N=3, and the genetic switch increases an expression amount of a reporter obtained by introduction of the ligand $L_2$ and an expression amount of the reporter obtained by introduction of a ligand $L_3$, is prevented from increasing an expression amount of the reporter obtained by introduction of the ligand $L_1$, expresses a reporter $R_2$, and has a function as a multi-output-type sensor that specifically responds to the ligand $L_2$ and the ligand $L_3$.

37. The genetic switch according to any one of the above-mentioned items 24 to 36, wherein the binder $B_1$, the binder $B_2$, the binder $B_3$, and the binder $B_N$ are each selected from a transcription factor, an enzyme, an antibody, a histone, a chaperone, or a ribosome.

38. The genetic switch according to any one of the above-mentioned items 24 to 36, wherein the binder $B_1$, the binder $B_2$, the binder $B_3$, and the binder $B_N$ are each a transcription factor or an enzyme.

39. A genetic switch for detection of a ligand $L_1$, which is obtained by introducing a mutation into a genetic construct carrying a gene sequence encoding a binder $B_1$ or a transcription factor $T_1$, which responds to a ligand $L_1$, and a gene sequence encoding a transcription factor $T_2$, wherein the genetic switch for detection of a ligand $L_1$ has a high ratio of an expression amount of a reporter obtained by introduction of the ligand $L_1$ and a ligand $L_2$ to an expression amount of the reporter obtained by introduction of the ligand $L_2$ or a high ratio of an expression amount of the reporter obtained by introduction of the ligand $L_1$ to the expression amount of the reporter obtained by introduction of the ligand $L_2$, and has a function of detecting the ligand $L_1$.

40. The genetic switch according to the above-mentioned item 39, wherein the ligand $L_1$ is arsenic.

Alternatively, the following invention may be given as an example.

1. A production method for a multi-input/multi-output-type genetic switch or a transcription factor for forming the switch, the method including one of (A) or (B), the method (A) including the following steps of (1) to (3):
(A)
(1) a step of introducing, into cells, or adding, to a cell-free protein synthesis system, a library of nucleic acids of fusion mutants of a transcription factor $T_1$, which responds to a ligand $L_1$, and a transcription factor $T_2$, which responds to a ligand $L_2$, the library being obtained by introducing mutations into a genetic construct carrying a gene sequence encoding the transcription factor $T_1$ and a gene sequence encoding the transcription factor $T_2$, and a reporter expression vector carrying a gene sequence encoding a promoter $P_1$ to be controlled by the transcription factor $T_1$ and/or a gene sequence encoding a promoter $P_2$ to be controlled by the transcription factor $T_2$, and a gene sequence encoding a reporter $R_x$ functionally linked to the promoter sequence $P_1$ and/or the promoter sequence $P_2$, where "x" represents an integer of 1 or more;

(2) a step of adding the ligand $L_1$ and/or the ligand $L_2$ to the cells or the cell-free protein synthesis system of (1); and (3) a step of selecting one of the fusion mutants of the transcription factor $T_1$ and the transcription factor $T_2$ as a genetic switch or a transcription factor for forming the switch through use of an expression amount of the reporter as an indicator, or the method (B) including the steps of (1) to (3):
(B)
(1) a step of introducing, into cells, or adding, to a cell-free protein synthesis system, a library of nucleic acids of fusion mutants of a transcription factor $T_1$, which responds to a ligand $L_1$, a transcription factor $T_2$, which responds to a ligand $L_2$, and a transcription factor $T_N$, which responds to a ligand $L_N$, the library being obtained by introducing mutations into a genetic construct carrying a gene sequence encoding the transcription factor $T_1$, a gene sequence encoding the transcription factor $T_2$, and a gene sequence encoding the transcription factor $T_N$, and a reporter expression vector carrying a gene sequence encoding a promoter $P_1$ to be controlled by the transcription factor $T_1$, a gene sequence encoding a promoter $P_2$ to be controlled by the transcription factor $T_2$, and/or a gene sequence encoding a promoter $P_N$ to be controlled by the transcription factor $T_N$, and a gene sequence encoding a reporter $R_x$ functionally linked to the promoter sequence $P_1$, the promoter sequence $P_2$, and/or the promoter sequence $P_N$, where "N" represents an integer of 3 or more;

(2) a step of introducing the ligand $L_1$, the ligand $L_2$, and/or the ligand $L_N$ into the cells or the cell-free protein synthesis system of (1); and (3) a step of selecting one of the fusion mutants of the transcription factor $T_1$, the transcription factor $T_2$, and the transcription factor $T_N$ as a genetic switch or a transcription factor for forming the switch through use of an expression amount of the reporter as an indicator.

2. The method according to the above-mentioned item 1, wherein in the method (A), the step of selecting includes selecting a fusion mutant having a high ratio of an expression amount of the reporter obtained by introduction of the ligand $L_1$ and the ligand $L_2$ to an expression amount of the reporter obtained by introduction of the ligand $L_1$ or the ligand $L_2$ as a genetic switch having a 2-input/AND-type output sensor function or a transcription factor for forming the switch.

3. The method according to the above-mentioned item 1, wherein in the method (A), when the promoter $P_2$ to be controlled by the transcription factor $T_2$ is used, the step of selecting includes selecting a fusion mutant having a high ratio of an expression amount of the reporter obtained by introduction of the ligand $L_1$ and the ligand $L_2$ to an expression amount of the reporter obtained by introduction of the ligand $L_2$ as a genetic switch having a 2-input/AND-type output sensor function or a transcription factor for forming the switch, or when the promoter $P_1$ to be controlled by the transcription factor $T_1$ is used, the step of selecting includes selecting a fusion mutant having a high ratio of an expression amount of the reporter obtained by introduction of the ligand $L_1$ and the ligand $L_2$ to an expression amount of the reporter obtained by introduction of the ligand $L_1$ as a genetic switch having a 2-input/AND-type output sensor function or a transcription factor for forming the switch.

4. The method according to the above-mentioned item 1, wherein in the method (A), when the promoter $P_1$ to be controlled by the transcription factor $T_1$ is used, the step of selecting includes selecting a fusion mutant having a high ratio of an expression amount of the reporter obtained by introduction of the ligand $L_2$ to an expression amount of the reporter obtained without any ligand as a genetic switch having a 2-input/OR-type sensor function or a transcription factor for forming the switch, or when the promoter $P_2$ to be controlled by the transcription factor $T_2$ is used, the step of selecting includes selecting a fusion mutant having a high ratio of an expression amount of the reporter obtained by introduction of the ligand $L_1$ to an expression amount of the reporter obtained without any ligand as a genetic switch having a 2-input/OR-type sensor function or a transcription factor for forming the switch.

5. The method according to the above-mentioned item 1, wherein in the method (A), when the promoter $P_1$ to be controlled by the transcription factor $T_1$ is used, the step of selecting includes selecting a fusion mutant having a high ratio of an expression amount of the reporter obtained by introduction of the ligand $L_1$ to an expression amount of the reporter obtained by introduction of the ligand $L_2$ as a genetic switch for an output-type sensor that specifically responds to the ligand $L_1$ or a transcription factor for forming the switch, or when the promoter $P_2$ to be controlled by the transcription factor $T_2$ is used, the step of selecting includes selecting a fusion mutant having a high ratio of an expression amount of the reporter obtained by introduction of the ligand $L_2$ to an expression amount of the reporter obtained by introduction of the ligand $L_1$ as a genetic switch for an output-type sensor that specifically responds to the ligand $L_2$ or a transcription factor for forming the switch.

6. The method according to the above-mentioned item 1, wherein in the method (A), when a repressor-type promoter $P_1$ to be controlled by the transcription factor $T_1$ is used, the step of selecting includes selecting a fusion mutant having a high ratio of an expression amount of the reporter obtained by introduction of the ligand $L_1$ or an expression amount of the reporter obtained by introduction of the ligand $L_2$ to an expression amount of the reporter obtained without any ligand as a genetic switch having a NOR-type sensor function or a transcription factor for forming the switch.

7. The method according to the above-mentioned item 1, wherein in the method (A), when a repressor-type promoter $P_1$ to be controlled by the transcription factor $T_1$ is used, the step of selecting includes selecting a fusion mutant having a high ratio of an expression amount of the reporter obtained without any ligand or obtained by introduction of one of the ligand $L_1$ or the ligand $L_2$ to an expression amount of the reporter obtained by introduction of the ligand $L_1$ and the ligand $L_2$ as a genetic switch having a NAND-type sensor function or a transcription factor for forming the switch.

8. The method according to the above-mentioned item 1, wherein in the method (A), the step of selecting includes selecting a fusion mutant in which both of an expression amount of the reporter obtained by introduction of the ligand $L_1$ and an expression amount of the reporter obtained by introduction of the ligand $L_2$ are decreased as a genetic switch having a function as a 2-input/3-stage output reduction-type sensor or a transcription factor for forming the switch.

9. The method according to the above-mentioned item 1, wherein in the method (A), the step of selecting includes selecting a fusion mutant in which both of an expression amount of the reporter obtained by introduction of the ligand $L_1$ and an expression amount of the reporter obtained by introduction of the ligand $L_2$ are increased as a genetic switch having a function as a 2-input/3-stage output increase-type sensor or a transcription factor for forming the switch.

10. The method according to the above-mentioned item 1, wherein in the method (B), $N=3$, and the step of selecting includes selecting a fusion mutant in which an expression amount of the reporter obtained by introduction of the ligand $L_1$, an expression amount of the reporter obtained by introduction of the ligand $L_2$, and an expression amount of the reporter obtained by introduction of a ligand $L_3$ are decreased as a genetic switch having a function as a 3-input/4-stage output reduction-type sensor or a transcription factor for forming the switch.

11. The method according to the above-mentioned item 1, wherein in the method (B), $N=3$, and the step of selecting includes selecting a fusion mutant in which an expression amount of the reporter obtained by introduction of the ligand $L_1$, an expression amount of the reporter obtained by introduction of the ligand $L_2$, and an expression amount of the reporter obtained by introduction of a ligand $L_3$ are increased as a genetic switch having a function as a 3-input/4-stage output increase-type sensor or a transcription factor for forming the switch.

12. The method according to the above-mentioned item 1, wherein in the method (B), $N=3$, a repressor-type promoter $P_1$ to be controlled by the transcription factor $T_1$, a reporter $R_1$ functionally linked to the promoter sequence $P_1$, an activator-type promoter $P_2$ to be controlled by the transcription factor $T_2$, a reporter $R_2$ functionally linked to the promoter sequence $P_2$, an activator-type promoter $P_3$ to be controlled by a transcription factor $T_3$, and a reporter $R_3$ functionally linked to a promoter sequence $P_3$ are used, a library of nucleic acids of fusion mutants of the transcription factor $T_1$ lacking a ligand binding ability as a result of mutation introduction, the transcription factor $T_2$, and the transcription factor $T_3$ is used, and the step of selecting includes selecting a fusion mutant in which an expression amount of the reporter obtained by introduction of the ligand $L_1$ and an expression amount of the reporter obtained by introduction of the ligand $L_2$ are prevented from being increased, in which an expression amount of the reporter obtained by introduction of a ligand $L_3$ is increased, and which expresses the reporter $R_1$, the reporter $R_2$, and the reporter $R_3$ as a genetic switch for a multi-output-type sensor that specifically responds to the ligand $L_3$ or a transcription factor for forming the switch.

13. The method according to the above-mentioned item 1, wherein in the method (B), $N=3$, a repressor-type promoter $P_1$ to be controlled by the transcription factor $T_1$, a reporter $R_1$ functionally linked to the promoter sequence $P_1$, an activator-type promoter $P_2$ to be controlled by the transcription factor $T_2$, a reporter $R_2$ functionally linked to the promoter sequence $P_2$, an activator-type promoter $P_3$ to be controlled by a transcription factor $T_3$, and a reporter $R_3$ functionally linked to a promoter sequence $P_3$ are used, a library of nucleic acids of fusion mutants of the transcription factor $T_1$ lacking a ligand binding ability as a result of mutation introduction, the transcription factor $T_2$ lacking a ligand binding ability as a result of mutation introduction, and the transcription factor $T_3$ is used, and the step of selecting includes selecting a fusion mutant in which an expression amount of the reporter obtained by introduction of the ligand $L_2$ and an expression amount of the reporter obtained by introduction of a ligand $L_3$ are increased, in which an expression amount of the reporter obtained by introduction of the ligand $L_1$ is prevented from being increased, and which expresses the reporter $R_2$ as a genetic switch for a multi-output-type sensor that specifically responds to the ligand $L_2$ and the ligand $L_3$ or a transcription factor for forming the switch.

14. A production method for a genetic switch for detection of a ligand $L_1$ or a transcription factor for forming the switch, including the following steps of (1) to (3):

(1) a step of introducing, into cells, or adding, to a cell-free protein synthesis system, a library of nucleic acids of fusion mutants of a transcription factor $T_1$, which responds to a ligand $L_1$, and a transcription factor LuxR, the library being obtained by introducing mutations into a genetic construct carrying a gene sequence encoding the transcription factor $T_1$ and a gene sequence encoding the transcription factor LuxR, and an expression vector carrying a gene sequence encoding a promoter $P_{lux}$ to be controlled by the transcription factor LuxR and a gene sequence encoding a reporter $R_x$ functionally linked to the promoter $P_{lux}$, where "x" represents an integer of 1 or more;

(2) a step of adding the ligand $L_1$ and/or a ligand AHL to the cells or the cell-free protein synthesis system of (1); and (3) a step of selecting a fusion mutant having a high ratio of an expression amount of the reporter obtained by introduction of the ligand $L_1$ and the ligand AHL to an expression amount of the reporter obtained by introduction of the ligand AHL or a fusion mutant having a high ratio of an expression amount of the reporter obtained by introduction of the ligand $L_1$ to an expression amount of the reporter obtained by introduction of the ligand AHL as a genetic switch for detection of the ligand $L_1$ or a transcription factor for forming the switch.

15. The method according to the above-mentioned item 14, wherein the ligand $L_1$ is arsenic.

16. A production method for a transcription factor capable of enhancing expression of a promoter $P_2$ to be controlled by a transcription factor $T_2$ through use of a ligand $L_1$, including the following steps of (1) to (3):

(1) a step of introducing, into cells, or adding, to a cell-free protein synthesis system, a library of nucleic acids of fusion mutants of a transcription factor $T_1$, which responds to the ligand $L_1$, and the transcription factor $T_2$, which responds to a ligand $L_2$, the library being obtained by introducing mutations into a genetic construct carrying a gene sequence encoding the transcription factor $T_1$ and a gene sequence encoding the transcription factor $T_2$, and a reporter expression vector carrying a gene sequence encoding the promoter $P_2$ to be controlled by the transcription factor $T_2$ and a gene sequence encoding a reporter $R_x$ functionally linked to the promoter $P_2$, where "x" represents an integer of 1 or more;

(2) a step of adding the ligand $L_1$ and/or the ligand $L_2$ to the cells or the cell-free protein synthesis system of (1); and (3) a step of selecting a fusion mutant having a high ratio of an expression amount of the reporter obtained by introduction of the ligand $L_1$ to an expression amount of the reporter obtained by introduction of the ligand $L_2$ as a transcription factor capable of enhancing expression of the promoter $P_2$ to be controlled by the transcription factor $T_2$ through use of the ligand $L_1$.

17. A method of using a genetic switch or a transcription factor for forming the switch obtained by the production method of at least one of the above-mentioned items 1 to 16 as a sensor for detection of the ligand $L_1$, the ligand $L_2$, and/or the ligand $L_N$.

18. The use method according to the above-mentioned item 17, wherein the method includes the following step (1) to (6) of adjusting detection sensitivity of the ligand $L_1$, the ligand $L_2$, and/or the ligand $L_N$:

(1) when response sensitivity to the ligand $L_1$ is to be increased, an addition concentration of the ligand $L_2$ and/or the ligand $L_N$ is increased;

(2) when response sensitivity to the ligand $L_1$ is to be decreased, an addition concentration of the ligand $L_2$ and/or the ligand $L_N$ is decreased;

(3) when response sensitivity to the ligand $L_2$ is to be increased, an addition concentration of the ligand $L_1$ and/or the ligand $L_N$ is increased;

(4) when response sensitivity to the ligand $L_2$ is to be decreased, an addition concentration of the ligand $L_1$ and/or the ligand $L_N$ is decreased;

(5) when response sensitivity to the ligand $L_N$ is to be increased, an addition concentration of the ligand $L_1$ and/or the ligand $L_2$ is increased; and (6) when response sensitivity to the ligand $L_N$ is to be decreased, an addition concentration of the ligand $L_1$ and/or the ligand $L_2$ is decreased.

19. A fusion mutant of AraC-LuxR$_{N86K\ and\ C245W}$ having an amino acid substitution selected from any one of the following groups (1) to (5) in an amino acid sequence set forth in SEQ ID NO: 15.

(1) F74L, P86T, V249A, and N298I
(2) P39R, I197N, and N252S
(3) E295K
(4) M175K and K491E
(5) H80F, H81K, Y82L, N393I, Y439H, R523L, and F541L 20. A fusion mutant of TetR-AraC-LuxR$_{N86K\ and\ C245W}$ having the following amino acid substitutions in an amino acid sequence set forth in SEQ ID NO: 16:

K46R, D95G, K108N, I134V, V145A, L204P, I214N, P216T, F217S, L409Q, T545A, and S569T.

21. A fusion mutant of ArsR-LuxR$_{N86K\ and\ C245W}$ having an amino acid substitution or deletion selected from any one of the following groups (1) and (2) in an amino acid sequence set forth in SEQ ID NO: 17.

(1) E16D and $T_{17}$-
(2) I84N, N102D, F240L, and P277A

Advantageous Effects of Invention

The present invention has been able to provide the production method for a multi-input/multi-output-type genetic switch or a transcription factor for forming the switch, and the multi-input/multi-output-type genetic switch or the transcription factor for forming the switch, or the gene fusion mutant.

BRIEF DESCRIPTION OF DRAWINGS

FIG. 17 shows examples of genetic switches for two ligands.

FIG. 18 shows examples of genetic switches for three ligands.

DESCRIPTION OF EMBODIMENTS

Figure 1:
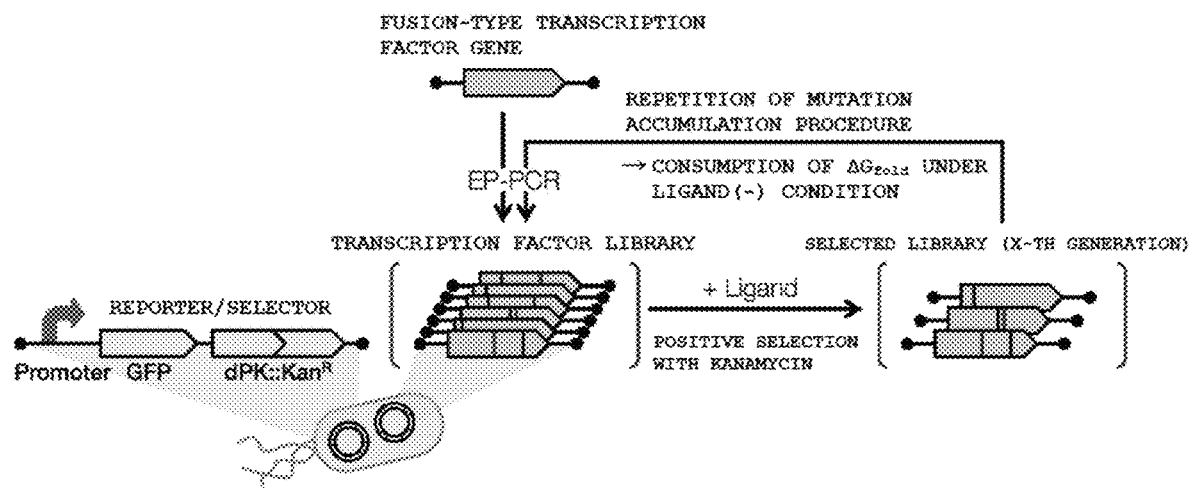
FIG. 1 is an outline of a production method for a multi-input/multi-output-type genetic switch.

The present invention relates to "a production method for a multi-input/multi-output-type genetic switch or a transcription factor for forming the switch", "a multi-input/multi-output-type genetic switch or a transcription factor for forming the switch", and to "a gene fusion mutant".

(Multi-Input/Multi-Output-Type)

The term "multi-input/multi-output (gate)-type" in the present invention means being capable of showing a plurality of kinds of responses to a plurality of ligands.

In the present invention, the following terms are used for describing the contents of the invention: "ligand $L_1$", "ligand $L_2$", "ligand $L_N$", "transcription factor $T_1$", "transcription factor $T_2$", "transcription factor $T_N$", "promoter $P_1$", "promoter $P_2$", "promoter $P_N$", "reporter R.", "binder $B_1$", "binder $B_2$", "binder $B_N$", and the like. Symbol "x" represents an integer of 1 or more, and "N" represents an integer of 3 or more.

In addition, in ligands, when "N" represents 3, three ligands, i.e., a ligand 1, a ligand $L_2$, and a ligand $L_3$ are meant; when "N" represents 4, four ligands, i.e., a ligand $L_1$, a ligand $L_2$, a ligand $L_3$, and a ligand $L_4$ are meant; and when "N" represents 5, five ligands, i.e., a ligand 1, a ligand $L_2$, a ligand $L_3$, a ligand $L_4$, and a ligand $L_5$ are meant. The same applies to the transcription factor $T_N$, the promoter $P_N$, and the binder $B_N$. Those terms are merely illustrative, and do not limit the contents of the present invention.

(Mode Examples of Multi-Input/Multi-Output-Type Genetic Switch or Transcription Factor)

A multi-output (gate) type that responds to two ligands, i.e., a ligand $L_1$ and a ligand $L_2$ may be exemplified by the following (see FIG. 17). As apparent from the results of Examples to be described below, the multi-input/multi-output-type genetic switch or the transcription factor for forming the switch of the present invention does not merely output "0" or "1", but can change its output amount in a manner dependent on the amounts of the ligands L (in particular, the concentrations of the ligands L in an environment). Output amounts are X1<X2<X3, and X1 represents an output value of substantially 0 or more.

(1) An OR gate
(2) An AND gate
(3) A NOR gate
(4) A NAND gate
(5) A gate that responds to the ligand $L_1$
(6) A gate that responds to the ligand $L_2$
(7) A 2-input-type 3-stage output reduction-type gate (its output decreases as the number (amount) of ligands increases)
(8) A 2-input-type 3-stage output increase-type gate (its output increases as the number (amount) of ligands increases)

Figure 18:
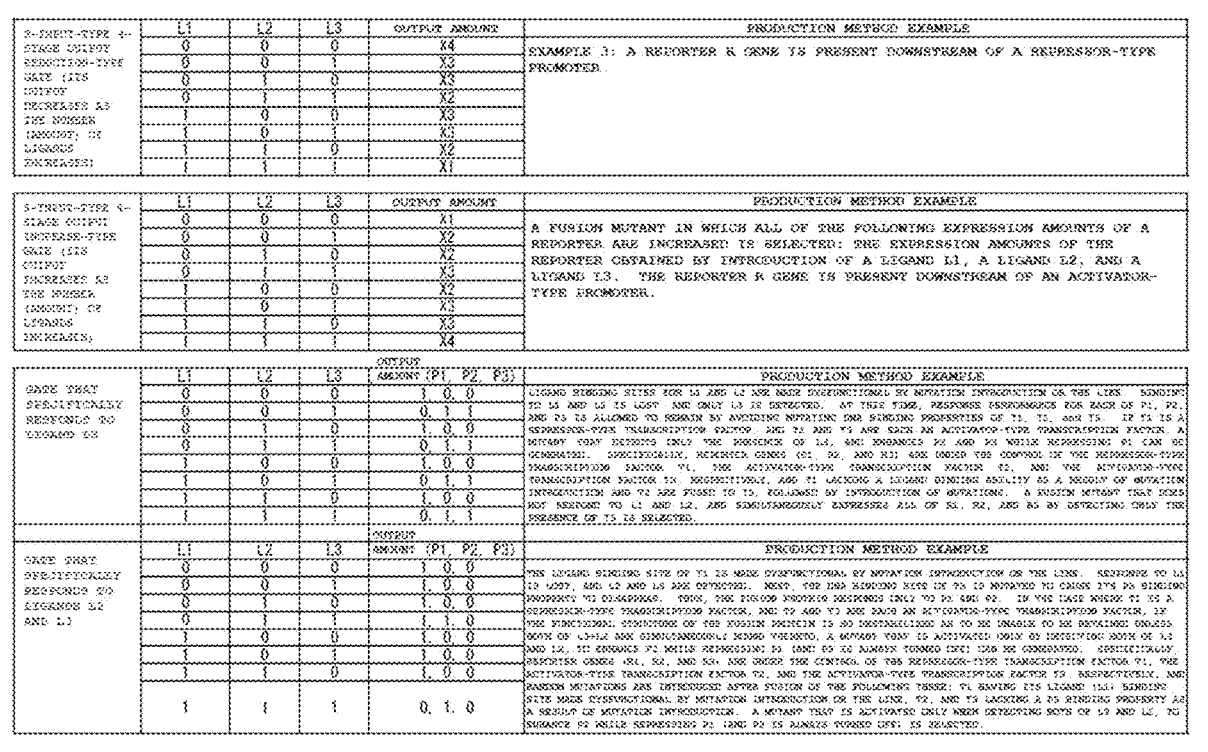

A multi-output (gate) type that responds to three ligands, i.e., a ligand $L_1$, a ligand $L_2$, and a ligand $L_3$ may be exemplified by the following (see FIG. 18).

(1) A 3-input-type 4-stage output reduction-type gate (its output decreases as the number (amount) of ligands increases)
(2) A 3-input-type 4-stage output increase-type gate (its output increases as the number (amount) of ligands increases)
(3) A gate that responds to the ligand $L_3$
(4) A gate that responds to the ligands $L_2$ and $L_3$ Output amounts are X1<X2<X3<X4, and X1 represents an output value of substantially 0 or more.

A multi-output (gate) type that responds to N ligands may be exemplified by the following.

(1) An N-input-type N+1-stage output reduction-type gate (its output decreases as the number (amount) of ligands increases)
(2) An N-input-type N+1-stage output increase-type gate (its output increases as the number (amount) of ligands increases)
(3) An N-input-type 2-stage output increase-type gate (its output differs between a case in which the number of ligands is N and any other case.)
(4) An N-input-type 2-stage output reduction-type gate (its output differs between a case in which the number of ligands is N and any other case.)

(Gene Fusion Mutant that Functions as Multi-Input/Multi-Output-Type Genetic Switch)

A gene fusion mutant that functions as a multi-input/multi-output-type genetic switch is capable of enhancing or repressing the expression of a promoter $P_1$, a promoter $P_2$, and/or a promoter $P_N$ to be controlled by $T_1$, $T_2$, and/or $T_N$ through use of a ligand $L_1$, a ligand $L_2$, and/or a ligand $L_N$.

More specifically, the gene fusion mutant may be exemplified by the following.

(1) A gene fusion mutant capable of enhancing expression of the promoter $P_2$ to be controlled by the transcription factor $T_2$ through use of the ligand $L_1$
(2) A gene fusion mutant capable of decreasing expression of the promoter $P_2$ to be controlled by the transcription factor $T_2$ through use of the ligand $L_1$
(3) A gene fusion mutant capable of enhancing or repressing expression of the promoters $P_1$, $P_2$, and $P_N$ to be controlled by the transcription factor $T_1$, the transcription factor $T_2$, and the transcription factor $T_N$ through use of the ligand $L_1$ (4) A gene fusion mutant capable of enhancing or repressing expression of the promoters $P_2$ and $P_N$ to be controlled by the transcription factor $T_2$ and the transcription factor $T_N$ through use of the ligand $L_1$ (5) A gene fusion mutant capable of enhancing or repressing expression of the promoters $P_1$, $P_2$, and $P_N$ to be controlled by the transcription factor $T_1$, the transcription factor $T_2$, and the transcription factor $T_N$ through use of the ligands $L_1$ and $L_2$ (6) A gene fusion mutant capable of enhancing or repressing expression of the promoters $P_2$ and $P_N$ to be controlled by the transcription factor $T_2$ and the transcription factor $T_N$ through use of the ligands $L_1$ and $L_2$ (7) A gene fusion mutant capable of enhancing expression of the promoters $P_1$, $P_2$, and $P_N$ to be controlled by the transcription factors $T_1$, $T_2$, and $T_N$ through use of the ligands $L_1$, $L_2$, and $L_N$ (8) A gene fusion mutant capable of repressing expression of the promoters $P_1$, $P_2$, and $P_N$ to be controlled by the transcription factors $T_1$, $T_2$, and $T_N$ through use of the ligands $L_1$, $L_2$, and $L_N$ (9) A gene fusion mutant capable of repressing the expression of the promoter $P_1$ to be controlled by the transcription factor $T_1$, the transcription factor $T_2$, and a transcription factor $T_3$, and enhancing the expression of the promoter $P_2$ and the promoter $P_3$ through use of the ligand $L_1$ More specifically, on the basis of Examples to be described below, the following gene fusion mutants may be given as examples.

(1) A transcription factor $T_1$-$T_2$ (AraC-LuxR) gene fusion mutant that gives a response of one of AND (AHL/Arabinose), OR (AHL/Arabinose), Ignore-AHL (Arabinose-only), and Ignore-arabinose (AHL-only) types acts on a promoter $P_1$ and a promoter $P_2$, and can simultaneously control genes downstream of the promoters.

(2) A transcription factor $T_1$-$T_2$-$T_3$ (TraR-AraC-LuxR) gene fusion mutant responds to a ligand $L_1$ (aTc), a ligand $L_2$ (arabinose), and a ligand $L_3$ (AHL), and can simultaneously control genes (including an operon) downstream of a promoter $P_1$ (TetP), a promoter $P_2$ (pBAD), and a promoter $P_3$ (pLux).

(Production Method for Multi-Input/Multi-Output-Type Genetic Switch)

The "production method for a multi-input/multi-output-type genetic switch or a transcription factor for forming the switch" of the present invention (hereinafter sometimes abbreviated as "production method of the present invention (method of the present invention)") essentially includes the steps of "fusing two or more transcription factor genes to each other or one or more transcription factors and one or more binders to each other" and "introducing mutations into the fusion-type transcription factor gene," and other steps are not particularly limited. For example, the production method of the present invention includes the following steps or steps that are substantially the same as the following steps.

In addition, reference may be made to a method described in the literature "PLoS ONE 10 (3):e0120243." previously published by the inventors of the present invention.

(Steps of Production Method of the Present Invention)

A production method for a multi-input/multi-output-type genetic switch or a transcription factor for forming the switch, the method including one of (A) or (B), the method (A) including the following steps of (1) to (3):

(A)

(1) a step of introducing, into cells, or adding, to a cell-free protein synthesis system, a library of nucleic acids of fusion mutants of a binder $B_1$ or a transcription factor $T_1$, which responds to a ligand $L_1$, and a binder $B_2$ or a transcription factor $T_2$, which responds to a ligand $L_2$, the library being obtained by introducing mutations into a genetic construct carrying a gene sequence encoding the binder $B_1$ or the transcription factor $T_1$ and a gene sequence encoding the binder $B_2$ or the transcription factor $T_2$, and a reporter expression vector carrying a gene sequence encoding a promoter $P_1$ to be controlled by the transcription factor $T_1$ and/or a gene sequence encoding a promoter $P_2$ to be controlled by the transcription factor $T_2$, and a gene sequence encoding a reporter $R_x$ functionally linked to the promoter sequence $P_1$ and/or the promoter sequence $P_2$, where "x" represents an integer of 1 or more;

(2) a step of adding the ligand $L_1$ and/or the ligand $L_2$ to the cells or the cell-free protein synthesis system of (1); and (3) a step of selecting one of the fusion mutants of the binder $B_1$ or the transcription factor $T_1$ and the binder $B_1$ or the transcription factor $T_2$ as a genetic switch or a transcription factor for forming the switch through use of an expression amount of the reporter as an indicator, or (B)

(1) a step of introducing, into cells, or adding, to a cell-free protein synthesis system, a library of nucleic acids of fusion mutants of a binder $B_1$ or a transcription factor $T_1$, which responds to a ligand $L_1$, a binder $B_2$ or a transcription factor $T_2$, which responds to a ligand $L_2$, and a binder $B_N$ or a transcription factor $T_N$, which responds to a ligand $L_N$, the library being obtained by introducing mutations into a genetic construct carrying a gene sequence encoding the binder $B_1$ or the transcription factor $T_1$, a gene sequence encoding the binder $B_2$ or the transcription factor $T_2$, and a gene sequence encoding the binder $B_N$ or the transcription factor $T_N$, and a reporter expression vector carrying a gene sequence encoding a promoter $P_1$ to be controlled by the transcription factor $T_1$, a gene sequence encoding a promoter $P_2$ to be controlled by the transcription factor $T_2$, and/or a gene sequence encoding a promoter $P_N$ to be controlled by the transcription factor $T_N$, and a gene sequence encoding a reporter $R_x$ functionally linked to the promoter sequence $P_1$, the promoter sequence $P_2$, and/or the promoter sequence $P_N$, where "N" represents an integer of 3 or more;

(2) a step of introducing the ligand $L_1$, the ligand $L_2$, and/or the ligand $L_N$ into the cells or the cell-free protein synthesis system of (1); and (3) a step of selecting one of the fusion mutants of the binder $B_1$ or the transcription factor $T_1$, the binder $B_2$ or the transcription factor $T_2$, and the binder $B_N$ or the transcription factor $T_N$ as a genetic switch or a transcription factor for forming the switch through use of an expression amount of the reporter as an indicator.

More specifically, the steps are as described below.

(A)

(1) A step of introducing, into cells, or adding, to a cell-free protein synthesis system, a library of nucleic acids of fusion mutants of a transcription factor $T_1$, which responds to a ligand $L_1$, and a transcription factor $T_2$, which responds to a ligand $L_2$, the library being obtained by introducing mutations into a genetic construct carrying a gene sequence encoding the transcription factor $T_1$ and a gene sequence encoding the transcription factor $T_2$, and a reporter expression vector carrying a gene sequence encoding a promoter $P_1$ to be controlled by the transcription factor $T_1$ and/or a gene sequence encoding a promoter $P_2$ to be controlled by the transcription factor $T_2$, and a gene sequence encoding a reporter $R_x$ functionally linked to the promoter sequence $P_1$ and/or the promoter sequence $P_2$, where "x" represents an integer of 1 or more (2) A step of adding the ligand $L_1$ and/or the ligand $L_2$ to the cells or the cell-free protein synthesis system of (1)

(3) A step of selecting one of the fusion mutants of the transcription factor $T_1$ and the transcription factor $T_2$ as a genetic switch or a transcription factor for forming the switch through use of an expression amount of the reporter as an indicator (B)

(1) A step of introducing, into cells, or adding, to a cell-free protein synthesis system, a library of nucleic acids of fusion mutants of a transcription factor $T_1$, which responds to a ligand $L_1$, a transcription factor $T_2$, which responds to a ligand $L_2$, and a transcription factor $T_N$, which responds to a ligand $L_N$, the library being obtained by introducing mutations into a genetic construct carrying a gene sequence encoding the transcription factor $T_1$, a gene sequence encoding the transcription factor $T_2$, and a gene sequence encoding the transcription factor $T_N$, and a reporter expression vector carrying a gene sequence encoding a promoter $P_1$ to be controlled by the transcription factor $T_1$, a gene sequence encoding a promoter $P_2$ to be controlled by the transcription factor $T_2$, and/or a gene sequence encoding a promoter $P_N$ to be controlled by the transcription factor $T_N$, and a gene sequence encoding a reporter $R_x$ functionally linked to the promoter sequence $P_1$, the promoter sequence $P_2$, and/or the promoter sequence $P_N$, where "N" represents an integer of 3 or more (2) A step of introducing the ligand $L_1$, the ligand $L_2$, and/or the ligand $L_N$ into the cells or the cell-free protein synthesis system of (1)

(3) A step of selecting one of the fusion mutants of the transcription factor $T_1$, the transcription factor $T_2$, and the transcription factor $T_N$ as a genetic switch or a transcription factor for forming the switch through use of an expression amount of the reporter as an indicator (Genetic Switch)

The "genetic switch" in the present invention means a "gene obtained by fusing two or more transcription factors to each other or one or more transcription factors and one or more binders to each other (fusion-type transcription factor gene)" having a switch function when expressed as a protein, and in particular, means a "fusion-type transcription factor gene having a mutation introduced therein" or a "gene fusion mutant" having a switch function when expressed as a protein.

A spacer may be introduced between the transcription factors or between the transcription factor and the binder as required. A recognition sequence of a restriction enzyme may be preferably inserted. An example thereof in the case of using a restriction enzyme XbaI may be an amino acid sequence SR (base sequence TCTAGA) derived from the recognition sequence of the enzyme, and an example thereof in the case of using a restriction enzyme SpeI may be an amino acid sequence TS (base sequence ACTAGT) derived from the recognition sequence of the enzyme.

The genetic switch of the present invention has any of various gate functions as described above.

(Ligand)

The "ligand L" in the present invention means a substance, such as a compound, which changes the function of a genetic switch by binding to a transcription factor, and as a result, induces direct or indirect regulation of the expression of a gene or a plurality of genes. The "ligand" may also be said to be a "compound that activates a genetic switch." The activating substance varies for each genetic switch.

(Binder)

The "binder B" in the present invention is selected from a transcription factor, an enzyme, an antibody, a histone, a chaperone, or a ribosome, but is preferably a transcription factor or an enzyme.

(Promoter)

The "promoter P" in the present invention means a nucleic acid sequence having promoter activity to be controlled by a transcription factor. The promoter means a nucleic acid sequence that is located 5'-upstream of translation initiation of a gene encoding a reporter R gene or an active portion thereof, and that controls the transcription of the reporter R.

The promoter is appropriately selected and used depending on the kind of host cells to be used. When bacteria are used as the hosts, any promoter may be used without any particular limitation as long as the promoter enables expression in the host cells, such as *E. coli*. Examples thereof may include promoters derived from *E. coli* and a phage, such as a λPR promoter, a PL promoter, a trp promoter, and a lac promoter. An artificially designed and modified promoter, such as a tac promoter, may be used. When yeast is used as the host, any promoter may be used without any particular limitation as long as the promoter enables expression in the yeast. Examples thereof may include a gal1 promoter, a gal10 promoter, a heat shock protein promoter, an MFα1 promoter, a PHO5 promoter, a PGK promoter, a GAP promoter, an ADH promoter, and an AOX1 promoter. When animal cells are used as the hosts, it is preferred that a recombinant vector be autonomously replicable in the cells, and at the same time, be constituted of the promoter, an RNA splice site, a gene of interest, a polyadenylation site, and a transcription termination sequence. In addition, an origin of replication may be contained as desired. As the promoter, there may be used an SRα promoter, an SV40 promoter, an LTR promoter, a CMV promoter, and the like. In addition, an early gene promoter of cytomegalovirus or the like may be used.

(Combination of Ligand L, Transcription Factor T, and Promoter P)

Combinations of a ligand L, a transcription factor T that responds to the ligand L, and a promoter P to be controlled by the transcription factor T may be exemplified by the following.

Activator-Type Promoter

Arabinose, AraC, and $P_{BAD}$ (Arabinose Operon)

Transcription does not occur unless an activator protein is bound to operator DNA. When arabinose is present in the environment, the conformation of the arabinose activator changes. The arabinose activator whose conformation has changed binds to the operator. Consequently, an RNA polymerase can transcribe the operon, with the result that a reporter R gene downstream of $P_{BAD}$ is expressed.

AHL, LuxR, and $P_{lux}$

When AHL is present in the environment, AHL binds to the transcription factor (transcription regulatory factor) LuxR. Then, the AHL-LUxR complex activates the pluX promoter, with the result that a reporter gene R, which is a downstream gene, is expressed.

Xylose, XylR, and $P_{xyl}$

Repressor-Type Promoter aTc, TetR, and Ptet

Arsenic, ArsR, and $P_{ars}$

IPTG, LacI, and $P_{lac}$ (Library of Nucleic Acids of Fusion Mutants)

The "library of nucleic acids of fusion mutants" in the present invention is fusion mutants of a transcription factor $T_1$ or a binder $B_1$, which responds to a ligand $L_1$, and a transcription factor $T_2$ or a binder $B_2$, which responds to a ligand $L_2$ (fusion mutants of a transcription factor $T_1$ or a binder $B_1$, which responds to a ligand $L_1$, the transcription factor $T_2$ or the binder $B_2$, which responds to a ligand $L_2$, and a transcription factor $T_N$ or a binder $B_N$, which responds to a ligand $L_N$), having a plurality of kinds of mutations obtained by introducing mutations known per se (e.g., random mutations, or site-directed mutations using stability prediction software, such as Fold-X) into a genetic construct (including an expression vector) carrying a gene sequence encoding the transcription factor $T_1$ or the binder $B_1$ and a gene sequence encoding the transcription factor $T_2$ or the binder $B_2$ or a genetic construct (including an expression vector) carrying a gene sequence encoding the transcription factor $T_1$ or the binder $B_1$, a gene sequence encoding the transcription factor $T_2$ or the binder $B_2$, and a gene sequence encoding the transcription factor $T_N$ or the binder $B_N$.

A fusion method for the transcription factor $T_1$ and the transcription factor $T_2$ is not particularly limited, and may be in-frame fusion in a tandem form or a fusion mode involving inserting one of the genes into a loop portion of the other transcription factor.

In addition, as an example of the mutations of the present invention, it is preferred to cause destabilization of a protein (fusion mutant). First, the stability of a protein refers to the stability of its folding state, i.e., a free energy change (ΔGfold) occurring when a polypeptide chain forming the protein forms a functional structure (is folded). In addition, the "destabilization" means that the free energy change (ΔGfold) associated with folding energy is reduced and ultimately canceled. For example, when a given amino acid substitution reduces the stability of the functional structure (fold), the amino acid substitution is a "mutation that causes destabilization (destabilizing mutation)." Specifically, if moderate destabilization can be induced with a mutation, the folded state of the fusion mutant can be retained (i.e., ΔGfold<0) only when a ligand is present.

(Reporter)

The "reporter Rx" in the present invention is not particularly limited as long as the reporter $R_x$ serves as an indicator for selecting a fusion mutant, but examples thereof may include a fluorescent protein (GFP), a thymidine kinase (see JP 2013-17473 A), alkyladenine DNA glycosidase (see WO 2012/060407 A1), a pigment synthesis protein (see JP 2014-223038 A), and a pigment protein (amilCP).

Specifically, in the case where a fluorescent protein or a pigment protein is used, a fusion mutant is selected on the basis of the coloration of a culture solution when a ligand L is added or not added into the medium. In the case where a thymidine kinase, alkyladenine DNA glycosylase, any of various drug transporters or drug resistance markers, a toxin-antitoxin pair, or the like is used, a fusion mutant is selected through use of the following indicator: the survival or death of cells or whether or not cells can proliferate.

Further, the reporter R is not particularly limited as long as the reporter R is functionally linked to its corresponding promoter P, but the kind of the reporter R may be changed for each promoter P. Examples thereof may include combinations such as promoter P1-reporter R1, promoter P2-reporter R2, and promoter P3-reporter R3.

(Reporter Expression Vector)

The "reporter expression vector" in the present invention carries: a gene sequence encoding a promoter $P_1$ to be controlled by a transcription factor $T_1$ and/or a gene sequence encoding a promoter $P_2$ to be controlled by a transcription factor $T_2$, and a gene sequence encoding a reporter $R_x$ functionally linked to the promoter $P_1$ sequence and/or a gene sequence encoding the reporter $R_x$ functionally linked to the promoter $P_2$ sequence; or a gene sequence encoding a promoter $P_1$ to be controlled by a transcription factor $T_1$, a gene sequence encoding a promoter $P_2$ to be controlled by a transcription factor $T_2$, and/or a gene sequence encoding a promoter $P_N$ to be controlled by a transcription factor $T_N$, and a gene sequence encoding a reporter $R_x$ functionally linked to the promoter $P_1$ sequence, a gene sequence encoding the reporter $R_x$ functionally linked to the promoter $P_2$ sequence, and/or a gene sequence encoding the reporter $R_x$ functionally linked to the promoter $P_3$ sequence. A plurality of kinds of the reporters $R_x$ may be present, or one or a plurality thereof may be present downstream of each promoter.

The expression vector refers to DNA that transfers an exogenous gene to host cells, in other words, vector DNA, the DNA allowing a gene of interest to be expressed in the host cells. The vector DNA is not particularly limited as long as the vector DNA is replicable in the host, and is appropriately selected depending on the kind of the host and intended use. The vector DNA may be vector DNA lacking a part of DNA except a part needed for replication as well as vector DNA obtained by extracting naturally occurring DNA. Typical examples of the vector DNA may include vector DNAs derived from a plasmid, a bacteriophage, and a virus. Examples of the plasmid DNA may include an *E. coli*-derived plasmid, a *Bacillus subtilis*-derived plasmid, and a yeast-derived plasmid. An example of the bacteriophage DNA is A phage. Examples of the virus-derived vector DNA may include vectors derived from animal viruses, such as a retrovirus, a vaccinia virus, an adenovirus, a papovavirus, SV40, a fowlpox virus, and a pseudorabies virus, or vectors derived from insect viruses, such as a baculovirus. Other examples of the vector DNA may include transposon-derived, insertion element-derived, and yeast chromosome element-derived vector DNAs. Alternatively, for example, there may be given vector DNA prepared by combining the above-mentioned materials, such as vector DNA prepared by combining genetic elements of a plasmid and a bacteriophage (e.g., a cosmid or a phagemid). It is required to incorporate a gene of interest into the vector DNA so that the gene of interest may be expressed, and at least the gene of interest and a regulatory DNA element, such as a promoter, are included as the constituent elements of the vector DNA. In addition to those elements, as desired, gene sequences carrying information on replication and control may be further incorporated in combination into the vector DNA by a method known per se. Examples of such gene sequences may include: cis-elements, such as a ribosome binding sequence, a terminator, a signal sequence, and an enhancer; a splicing signal; and selection markers (selectors: a dihydrofolate reductase gene, an ampicillin resistance gene, a neomycin resistance gene, a kanamycin resistance gene, and the like). One or more kinds of gene sequences selected therefrom may be incorporated into the vector DNA.

A genetic engineering technology known per se may be applied as a method of incorporating the gene of interest into the vector DNA. For example, there may be employed a method involving treating the gene of interest with an appropriate restriction enzyme to cleave the gene at a specific site, then mixing the resultant with vector DNA treated in the same manner, and recombining them with a ligase. Alternatively, desired vector DNA may be obtained by ligating the gene of interest with an appropriate linker, and inserting the resultant into a multiple cloning site of a vector suited for the purpose.

A method of introducing the expression vector into host cells is not particularly limited as long as the method is an introduction method by which the vector DNA can be introduced into the host cells and the gene of interest can be expressed in the host cells, and any known method appropriately selected depending on the kind of the host cells may be used. Examples thereof may include an electroporation method, a calcium phosphate method, and a lipofection method.

(Cells or Cell-Free Protein Synthesis System)

The "cells or cell-free protein synthesis system" in the present invention is not particularly limited as long as the environment allows the transcription factor T, the promoter P, and the reporter $R_x$ to express a protein. For example, the cells may be any of prokaryotic cells and isolated eukaryotic cells, but are preferably prokaryotic cells having short cell cycles and high proliferation rates. Cells having such properties are useful for a rapid production method for a genetic switch. An example of the cell-free protein synthesis system may be a known cell-free protein synthesis system (e.g., wheat or *E. coli*) containing components essential for protein synthesis.

In the "step of adding the ligand $L_1$ and/or the ligand $L_2$ to the cells or the cell-free protein synthesis system," the addition of the ligand $L_1$ and/or the ligand $L_2$ to the cells or the cell-free protein synthesis system may be before, after, or substantially simultaneous with the addition of the library of nucleic acids of fusion mutants and/or the reporter expression vector to the cells.

(Selecting as Genetic Switch or Transcription Factor for Forming the Switch)

In the "step of selecting as a genetic switch or a transcription factor for forming the switch" in the present invention, a fusion mutant showing the properties of a multi-input/multi-output-type genetic switch type of interest is selected through use of the expression amount of the reporter $R_x$ as an indicator.

The gene sequence and/or amino acid sequence of the selected fusion is analyzed by a method known per se. Thus, information (base sequence, amino acid sequence) on the multi-input/multi-output-type genetic switch or the transcription factor can be obtained.

Further, with the information, the multi-input/multi-output-type genetic switch or the transcription factor can be easily obtained by using a protein synthesis system known per se.

(Genetic Circuit)

The "genetic circuit" in the present invention has at least the following.

A gene sequence encoding a transcription factor $T_1$ that responds to a ligand $L_1$ gene sequence encoding a transcription factor $T_2$ that responds to a ligand $L_2$ A gene sequence encoding a promoter $P_1$ to be controlled by the transcription factor $T_1$ and/or a gene sequence encoding a promoter $P_2$ to be controlled by the transcription factor $T_2$ A reporter $R_x$ functionally linked to the promoter $P_1$ sequence and/or a reporter $R_x$ functionally linked to the promoter $P_2$ sequence All of the foregoing may be contained in the same genetic construct, or may be separately contained in a plurality of genetic constructs.

As required, the genetic circuit may further contain cis-elements, such as a ribosome binding sequence, a terminator, a signal sequence, and an enhancer, a splicing signal, selection markers (selectors: a dihydrofolate reductase gene, an ampicillin resistance gene, a neomycin resistance gene, a kanamycin resistance gene, and the like), and the like.

The genetic circuit may also further contain an operator (DNA region to which a repressor or an activator binds) sequence or a regulatory gene sequence.

(Biosensor)

The configuration of a "biosensor" in the present invention is not particularly limited as long as the biosensor can show a plurality of kinds of responses to a plurality of ligands, but an example thereof may be cells serving as a system in which transcription factors, promoters, and reporters can be expressed as proteins (serving as a system capable of expressing a genetic circuit) or a cell-free protein synthesis system containing a genetic circuit.

Figure 16:
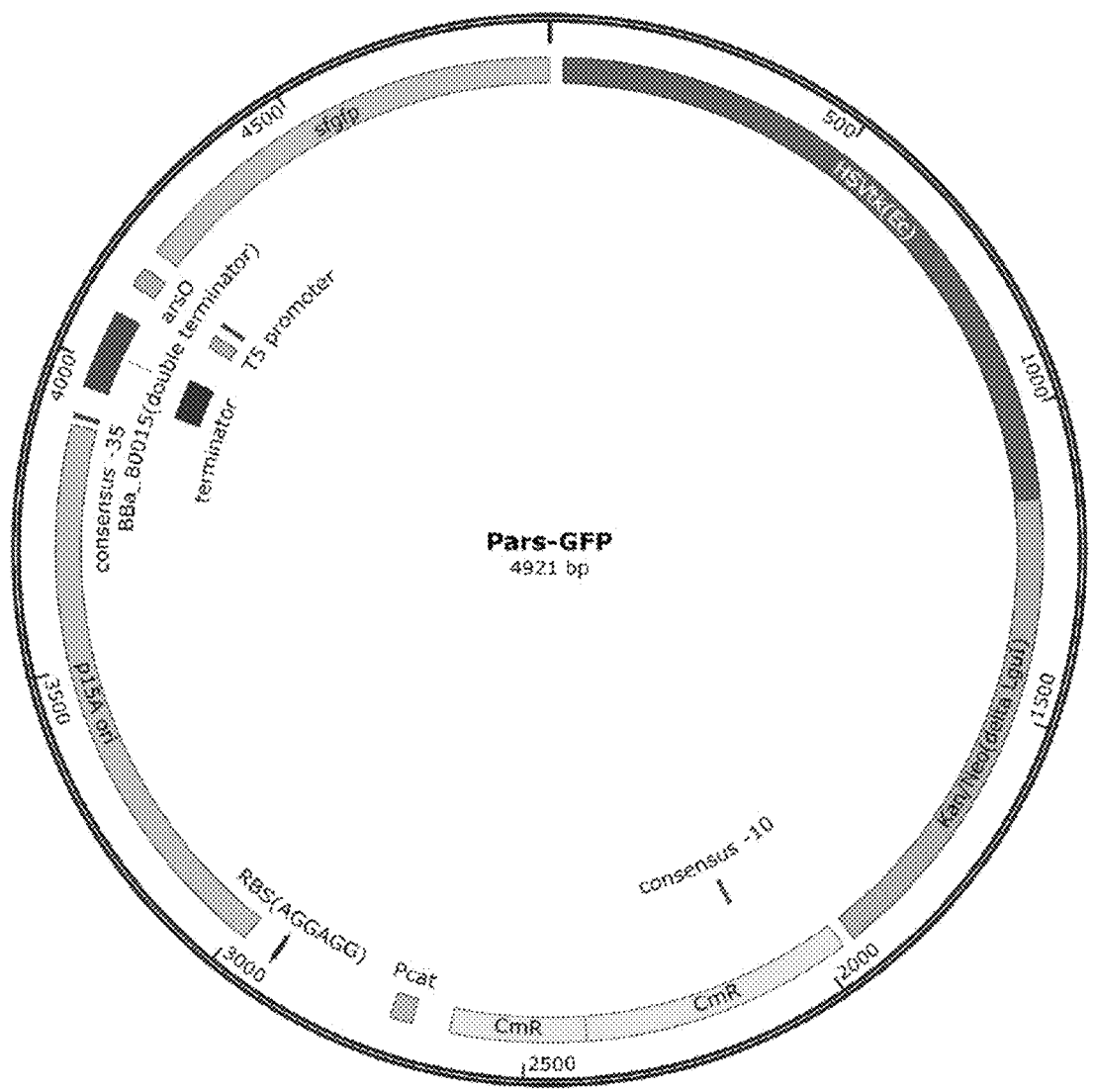
FIG. 16 is an outline of the plasmid structure of Pars-GFP.

Examples of Production Method for Multi-Input/Multi-Output-Type Genetic Switch or Transcription Factor In the multi-input/multi-output-type genetic switch of the present invention, a multi-input/multi-output-type genetic switch or transcription factor of interest may be selected by a method described in FIG. 16 and FIG. 17.

Example 1 of Production Method for Multi-Input/Multi-Output-Type Genetic Switch or Transcription Factor As an example of the production method of the present invention in which mutation introduction is performed 2 or more times, a production method for a genetic switch or transcription factor for an output-type sensor that specifically responds to the ligand $L_2$ is described:

(i) when the promoter $P_1$ to be controlled by the transcription factor $T_1$ is used, a step of obtaining a fusion mutant having a high ratio of an expression amount of the reporter obtained by introduction of the ligand $L_2$ to an expression amount of the reporter obtained by introduction of the ligand $L_1$ as a parent of a second generation;

(ii) a step of introducing random mutations into the parent of the second generation to obtain a second generation library of nucleic acids or proteins of fusion mutants;

(iii) a step of introducing, into cells, the second generation library and an expression vector carrying a gene sequence encoding the promoter $P_1$ to be controlled by the transcription factor $T_1$ and a gene sequence encoding a reporter functionally linked to the promoter sequence;

(iV) a step of introducing the ligand $L_1$ and/or the ligand $L_2$ into the cells of (iii);

(V) a step of selecting a fusion mutant having a high ratio of an expression amount of the reporter obtained by introduction of the ligand $L_2$ to an expression amount of the reporter obtained without any ligand as a genetic switch for a 2-input/1-way output-type sensor that specifically responds to the ligand $L_2$.

As required, the steps (i) to (V) may be repeated to increase the number of times of mutation introduction and the number of times of selection.

Example 2 of Production Method for Multi-Input/Multi-Output-Type Genetic Switch or Transcription Factor When the number of kinds of transcription factors included in the mutant fusion is increased, it is also appropriate to partially mutate only a certain transcription factor in advance (see Example 3). With this, the ligand binding site of the transcription factor T may be made dysfunctional.

(Production Method for Genetic Switch for Detection of Ligand or Transcription Factor)

In the production method of the present invention, a genetic switch for detection of the ligand $L_1$ or a transcription factor for forming the switch may be obtained through the following steps.

(1) A step of introducing, into cells, or adding, to a cell-free protein synthesis system, a library of nucleic acids of fusion mutants of a binder $B_1$ or a transcription factor $T_1$, which responds to a ligand $L_1$, and a transcription factor $T_2$, the library being obtained by introducing mutations into a genetic construct carrying a gene sequence encoding the binder $B_1$ or the transcription factor $T_1$ and a gene sequence encoding the transcription factor $T_2$, and an expression vector carrying a gene sequence encoding a promoter $P_2$ to be controlled by the transcription factor $T_2$ and a gene sequence encoding a reporter $R_x$ functionally linked to the promoter $P_2$, where X represents an integer of 1 or more (2) A step of adding the ligand $L_1$ and/or the ligand $L_2$ to the cells or the cell-free protein synthesis system of (1)

(3) A step of selecting a fusion mutant having a high ratio of an expression amount of the reporter obtained by introduction of the ligand $L_1$ and the ligand $L_2$ to an expression amount of the reporter obtained by introduction of the ligand $L_2$ or a fusion mutant having a high ratio of an expression amount of the reporter obtained by introduction of the ligand $L_1$ to an expression amount of the reporter obtained by introduction of the ligand $L_2$ as a genetic switch for detection of the ligand $L_1$ or a transcription factor for forming the switch More specifically, on the basis of Example 6 to be described below, a genetic switch for high-sensitivity ligand detection or a transcription factor therefor can be obtained by using AHL as a ligand, LuxR as a transcription factor, and $P_{lux}$ as a promoter. A production example is as described below.

(1) A step of introducing, into cells or a cell-free protein synthesis system, a library of nucleic acids of fusion mutants of a transcription factor $T_1$, which responds to a ligand and a transcription factor LuxR, the library being obtained by introducing mutations into a genetic construct carrying a gene sequence encoding the transcription factor $T_1$ and a gene sequence encoding the transcription factor LuxR, and an expression vector carrying a gene sequence encoding a promoter $P_{lux}$ to be controlled by the transcription factor LuxR and a gene sequence encoding a reporter $R_x$ functionally linked to the promoter sequence (2) A step of adding the ligand $L_1$ and/or a ligand AHL to the cells or the cell-free protein synthesis system of (1)

(3) A step of selecting a fusion mutant having a high ratio of an expression amount of the reporter obtained by introduction of the ligand $L_1$ and the ligand AHL to an expression amount of the reporter obtained by introduction of the ligand AHL or a fusion mutant having a high ratio of an expression amount of the reporter obtained by introduction of the ligand $L_1$ to an expression amount of the reporter obtained by introduction of the ligand AHL as a genetic switch for detection of the ligand $L_1$ or a transcription factor therefor An example of the ligand may be arsenic.

(Method of Adjusting Detection Sensitivity of Ligand)

In the biosensor of the present invention, the detection sensitivity of the ligand $L_1$, the ligand $L_2$, and/or the ligand $L_N$ can be easily adjusted as described below.

(1) When response sensitivity to the ligand $L_1$ is to be increased, an addition concentration of the ligand $L_2$ and/or the ligand $L_N$ is increased.

(2) When response sensitivity to the ligand $L_1$ is to be decreased, an addition concentration of the ligand $L_2$ and/or the ligand $L_N$ is decreased.

(3) When response sensitivity to the ligand $L_2$ is to be increased, an addition concentration of the ligand $L_1$ and/or the ligand $L_N$ is increased.

(4) When response sensitivity to the ligand $L_2$ is to be decreased, an addition concentration of the ligand $L_1$ and/or the ligand $L_N$ is decreased.

(5) When response sensitivity to the ligand $L_N$ is to be increased, an addition concentration of the ligand $L_1$ and/or the ligand $L_2$ is increased.

(6) When response sensitivity to the ligand $L_N$ is to be decreased, an addition concentration of the ligand $L_1$ and/or the ligand $L_2$ is decreased.

(Production Method for Transcription Factor Capable of Increasing Expression of Promoter $P_2$ to be Controlled by Transcription Factor $T_2$ Through Use of Ligand $L_1$)

In the production method of the present invention, there may be obtained such a fusion mutant that a combination of the ligand $L_1$ and the transcription factor $T_1$ can enhance/repress (ON/OFF) the expression of the promoter $P_2$ gene under the control sequence of the transcription factor $T_2$ serving as a fusion partner. For example, the following method may be given.

(1) A step of introducing, into cells or a cell-free protein synthesis system, a library of nucleic acids of fusion mutants of a transcription factor $T_1$, which responds to a ligand $L_1$, and a transcription factor $T_2$, which responds to a ligand $L_2$, the library being obtained by introducing mutations into a genetic construct carrying a gene sequence encoding the transcription factor $T_1$ and a gene sequence encoding the transcription factor $T_2$, and a reporter expression vector carrying a gene sequence encoding a promoter $P_2$ to be controlled by the transcription factor $T_2$ and a gene sequence encoding a reporter $R_x$ functionally linked to the promoter sequence (2) A step of adding the ligand $L_1$ and/or the ligand $L_2$ to the cells or the cell-free protein synthesis system of (1)

(3) A step of selecting a fusion mutant having a high ratio of an expression amount of the reporter obtained by introduction of the ligand $L_1$ to an expression amount of the reporter obtained by introduction of the ligand $L_2$ as a transcription factor capable of increasing expression of the promoter $P_2$ to be controlled by the transcription factor $T_2$ through use of the ligand $L_1$ The multi-input/multi-output-type genetic switch, the transcription factor for forming the switch, and the fusion mutant of the present invention may be used for protein synthesis, induction of protein secretion, induction of a biosynthetic pathway, regulation of a flow rate of a biosynthetic pathway, induction of cell proliferation, induction of a physiological function, or a control mechanism for a physiological function.

The present invention also relates to a "fusion mutant of AraC-LuxR$_{N86K\ and\ C245W}$", a "fusion mutant of TetR-AraC-LuxR$_{N86K\ and\ C245W}$", and a "fusion mutant of ArsR-LuxR$_{N86K\ and\ C245W}$".

The fusion mutant of AraC-LuxR$_{N86K\ and\ C245W}$ of the present invention has an amino acid substitution selected from any one of the following groups (1) to (5) in an amino acid sequence set forth in SEQ ID NO: 15 (see Table 5).

(1) F74L, P86T, V249A, and N298I (2) P39R, I197N, and N252S (3) E295K
(4) M175K and K491E
(5) H80F, H81K, Y82L, N393I, Y439H, R523L, and F541L The fusion mutant of AraC-LuxR$_{N86K\ and\ C245W}$ of the above-mentioned item (1) has AND gate-type transcriptional activity (responds when both of arabinose and homoserine lactone are present).

The fusion mutant of AraC-LuxR$_{N86K\ and\ C245W}$ of the above-mentioned item (2) has AND gate-type transcriptional activity (responds when both of arabinose and homoserine lactone are present).

The fusion mutant of AraC-LuxR$_{N86K\ and\ C245W}$ of the above-mentioned item (3) has OR gate-type transcriptional activity (responds when arabinose or homoserine lactone is present).

The fusion mutant of AraC-LuxR$_{N86K\ and\ C245W}$ of the above-mentioned item (4) has L1 only gate-type transcriptional activity (specifically responds to arabinose).

The fusion mutant of AraC-LuxR$_{N86K\ and\ C245W}$ of the above-mentioned item (5) has L2 only gate-type transcriptional activity (specifically responds to AHL).

The fusion mutant of AraC-LuxR$_{N86K\ and\ C245W}$ of the present invention contains: an amino acid sequence having 1 to 20, preferably 1 to 15, more preferably 1 to 10, most preferably 1 to 5 amino acids substituted, truncated, inserted, and/or added in the amino acid-substituted sequence described in any one of the above-mentioned items (1) to (5), and having substantially equivalent activity to the transcriptional activity of the substitution mutant of any one of the above-mentioned items (1) to (5); and an amino acid sequence having 90% or more (or 92% or more, 94% or more, 96% or more, 98% or more, 99% or more) homology to the amino acid-substituted sequence described in any one of the above-mentioned items (1) to (5), and having substantially equivalent activity to the transcriptional activity of the substitution mutant of the above-mentioned items (1) to (5).

In the introduction of a mutation into a peptide, for example, a substitution between homologous amino acids (e.g., polar amino acids, non-polar amino acids, hydrophobic amino acids, hydrophilic amino acids, positively charged amino acids, negatively charged amino acids, and aromatic amino acids) is easily conceivable from the viewpoint of preventing basic properties (e.g., physical properties, function, physiological activity, or immunological activity) of the peptide from being changed.

The fusion mutant of TetR-AraC-LuxR$_{N86K\ and\ C245W}$ of the present invention has amino acid substitutions of K46R, D95G, K108N, I134V, V145A, L204P, I214N, P216T, F217S, L409Q, T545A, and S569T in an amino acid sequence set forth in SEQ ID NO: 16.

In addition, the fusion mutant of TetR-AraC-LuxR$_{N86K\ and\ C245W}$ of the present invention has 3-input-type 4-stage output reduction-type transcriptional activity (its response reduces as the kinds and amounts of three ligands increase).

The fusion mutant of TetR-AraC-LuxR$_{N86K\ and\ C245W}$ of the present invention contains: an amino acid sequence having 1 to 20, preferably 1 to 15, more preferably 1 to 10, most preferably 1 to 5 amino acids substituted, truncated, inserted, and/or added in the amino acid sequence of the amino acid substitution mutant described above, and having substantially equivalent activity to the transcriptional activity of the substitution mutant; and an amino acid sequence having 90% or more (or 92% or more, 94% or more, 96% or more, 98% or more, or 99% or more) homology to the amino acid sequence of the amino acid substitution mutant described above, and having substantially equivalent activity to the transcriptional activity of the above-mentioned substitution mutant.

The fusion mutant of ArsR-LuxR$_{N86K\ and\ C245W}$ of the present invention has one amino acid substitution or deletion selected from one of the following groups (1) and (2) in an amino acid sequence set forth in SEQ ID NO: 17.

(1) E16D and T17-("-" means truncation).
(2) I84N, N102D, F240L, and P277A

The fusion mutant of ArsR-LuxR$_{N86K\ and\ C245W}$ of the above-mentioned item (1) is an AND-type arsenic switch having high stringency.

The fusion mutant of ArsR-LuxR$_{N86K\ and\ C245W}$ of the above-mentioned item (2) is a high-sensitivity AND-type arsenic switch.

The fusion mutant of ArsR-LuxR$_{N86K\ and\ C245W}$ of the present invention contains: an amino acid sequence having 1 to 20, preferably 1 to 15, more preferably 1 to 10, most preferably 1 to 5 amino acids substituted, truncated, inserted, and/or added in the amino acid-substituted/deleted sequence described in the above-mentioned item (1) or (2), and having substantially equivalent activity to the transcriptional activity of the substitution/deletion mutant of the above-mentioned item (1) or (2); and an amino acid sequence having 90% or more (or 92% or more, 94% or more, 96% or more, 98% or more, or 99% or more) homology to the amino acid-substituted/deleted sequence described in the above-mentioned item (1) or (2), and having substantially equivalent activity to the transcriptional activity of the substitution/deletion mutant of the above-mentioned item (1) or (2).

The present invention is described below by way of Examples, but the present invention is by no means limited to Examples.

Example 1

(Reagents)
Reagents and the like used in Example 2 and Example 3 described below are as described below.
(Pre-PCR)
On the basis of the following composition table, a plasmid was used as a template and subjected to PCR once to make DNA linear.

TABLE 1

| | Volume [μL] | Final Concentration |
|---|---|---|
| Template DNA | 1 | — |
| 5 μM Fwd primer | 3 | 0.3 μM |
| 5 μM Rev primer | 3 | 0.3 μM |
| 10× KOD plus buffer 2 (product of Toyobo Life Science) | 5 | 1× |
| 2 mM each dNTPs | 5 | 0.2 mM each |
| 25 mM MgSO$_4$ | 3 | 1.5 mM |
| 1 U/μL KOD plus (product of Toyobo Life Science) | 1 | 0.02 U/μL |
| NFW (Nuclease-free Water) | 29 | — |
| Total amount | 50 | |

{Error-Prone PCR (EP-PCR)}
On the basis of the following composition table, EP-PCR was performed using linear DNA as a template. An amplification factor was set to 100 times, 1,000 times, or 10,000 times, and a MnCl$_2$ concentration was set to 10 μM or 50 μM. For MnCl$_2$, a stock solution concentrated 10-fold was diluted before use.

TABLE 2

|  | Volume [μL] | Final Concentration |
|---|---|---|
| Template DNA | 1 | — |
| 5 μM Fwd primex | 5 | 0.5 μM |
| 5 μM Rev primer | 5 | 0.5 μM |
| 10× ThermoPol buffer | 5 | 1× |
| 2 mM each dNTPs | 5 | 0.2 mM each |
| 10 μM, 50 μM MnCl$_2$ | 5 | 10 μM, 50 μM/10 μM |
| 5 U/μl Taq | 1 | 0.1 U/μL |
| NFW | 23 | — |
| Total amount | 50 |  |

(Digestion Reaction)

On the basis of the following composition table, both of AL (AraC-LuxR$_{N86K\ and\ C245W}$, see FIG. 9) and TAL (TetR-AraC-LuxR$_{N86K\ and\ C245W}$: see FIG. 10) were subjected to digestion with NcoI-HF (product manufactured by New England Biolabs) and BamHI-HF (product manufactured by New England Biolabs). In the digestion of the vectors, rSAP (Shrimp Alkaline Phosphatase, product manufactured by New England Biolabs) was also simultaneously added. Template DNA was prepared in an amount of about 1 μg per 50 μL of a reaction system. Reaction conditions were set to 37° C. and 3 hours.

TABLE 3

|  | Volume [μL] | Final Concentration |
|---|---|---|
| Template DNA | x | 20 ng/μL |
| 10× CutSmart (product manufactured by New England Biolabs) | 5 | 1× |
| 20 U/μL NcoI-HF | 1 | 0.4 U/μL |
| 20 U/μL BamHI-HF | 1 | 0.4 U/μL |
| 1 U/μL rSAP (or NFW) | 1 | 0.02 U/μL |
| NFW | 42 − x | — |
| Total amount | 50 |  |

(Ligation Reaction)

On the basis of the following composition table, for AL, a reaction was performed using 100 ng of the vector and about 100 ng of the insert, and for TAL, a reaction was performed using 100 ng of the vector and about 150 ng of the insert. Reaction conditions were set to 16° C. overnight.

TABLE 4

|  | Volume [μL] | Final Concentration |
|---|---|---|
| Insert DNA | x |  |
| Vector DNA | y |  |
| 10× T4 DNA ligase buffer (product manufactured by New England Biolabs) | 1 | 1× |
| 400 U/μL T4 DNA ligase | 1 | 40 U/μL |
| NFW | 8 − x − y |  |
| Total amount | 10 |  |

Example 2

(Development of Multi-Input/Multi-Output Sensor)

In this Example, as an example of the production of a multi-input/multi-output sensor, an arabinose-responsive transcription factor AraC (obtained by PCR from *E. coli* MG1655) and a mutant of an AHL (homoserine lactone)-responsive transcription factor LuxR {N86K, C245W: Kimura et al., J. Gen. Appl. Microbiol., 62, 240-247 (2016)} were used.

(Confirmation of Characteristics of AraC-LuxR$_{N86K\ and\ C245W}$)

As illustrated in FIG. 2(a), an AraC-LuxR$_{N86K\ and\ C245W}$ fusion (SEQ ID NO: 15) was generated on the basis of a method known per se. The results of addition of L-arabinose and/or AHL to medium in which the fusion is present are shown in FIG. 2(b).

AraC-LuxR$_{N86K\ and\ C245W}$ has a structure in which two transcription factor proteins are fused in tandem. Therefore, it was confirmed that the function of each transcription factor was unchanged. More specifically, the fusion protein enhanced the gene downstream of the arabinose promoter by responding only to arabinose, but AHL did not interfere therewith at all. Similarly, the expression of the gene downstream of the Lux promoter was enhanced by the fusion protein in an AHL-dependent manner, but was not enhanced with arabinose.

(Generation of Mutants of AraC-LuxR$_{N86K\ and\ C245W}$)

As illustrated in FIG. 2(c) and FIG. 2(d), random mutations were introduced into AraC-LuxR$_{N86K\ and\ C245W}$ by a known EP-PCR method to generate mutants of AraC-LuxR$_{N86K\ and\ C245W}$. The details are as described below.

Example 2-1: Development Example 1 of 2-Input/AND-Type Sensor

Figure 9:
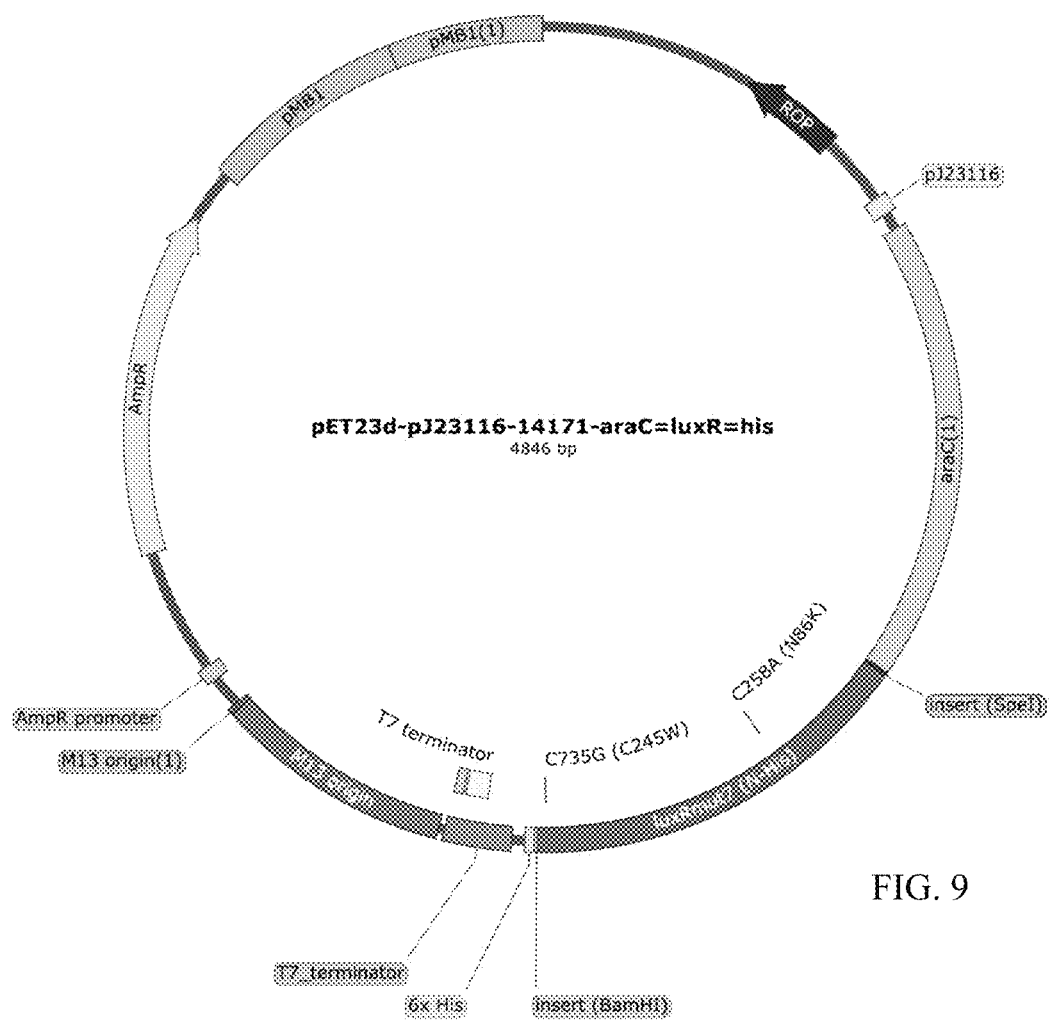
FIG. 9 is an outline of the plasmid structure of AraC-LuxR$_{N86K\ and\ C245W}$.
Figure 10:
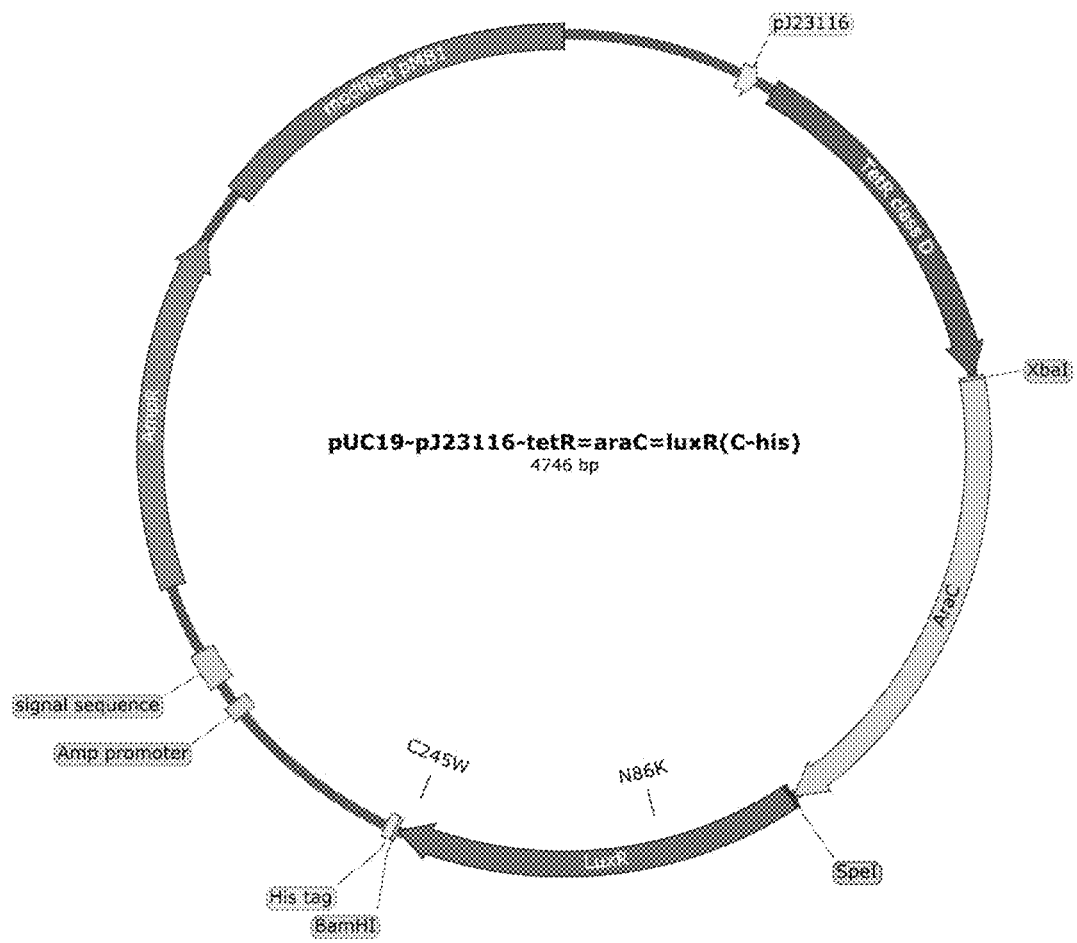
FIG. 10 is an outline of the plasmid structure of TetR-AraC-LuxR$_{N86K\ and\ C245W}$.

The full length of AraC-LuxR$_{N86K\ and\ C245W}$ (plasmid: FIG. 9) was subjected to EP-PCR (50 μM MnCl$_2$, amplification factor: 10,000 times) to generate a mutant pool having random mutations introduced therein (the library size was 3×10$^6$). Through use of P$_{lux}$-GFP as a reporter, 90 colonies showing fluorescence on solid medium containing 10 μM AHL and 13 mM L-arabinose were picked. The ligand responsiveness of those colonies was evaluated (see FIG. 2). Specifically, culture was performed under separate conditions of "10 μM AHL alone" and "10 μM AHL+13 mM L-arabinose", and 15 mutants each having an improved BOTH (L-arabinose+AHL)/AHL ratio of 2 times or more were obtained. Among the mutants, a mutant having high stringency at the time of addition of AHL alone, and having a function as an AND (logical product) gate (2-input/AND-type sensor) even when the reporter was changed to P$_{BAD7}$-GFP was able to be obtained (see FIG. 2(d)).

Through only one round of EP-PCR/screening, a mutant of AraC-LuxR$_{N86K\ and\ C245W}$ (see Table 5: F74L, P86T, V249A, and N298I) was able to be obtained.

More specifically, it was confirmed that GFP expression under P$_{lux}$ control acted as an AND gate that responded only when both of arabinose and AHL were present. Further, it was confirmed that a similar action was obtained for not only the Lux promoter, but also the arabinose promoter {araP (P$_{BAD}$)}. That is, the obtained mutant of AraC-LuxR$_{N86K\ and\ C245W}$ (see Table 5: F74L, P86T, V249A, and N298I) was able to be caused to independently AND-respond to each of two different promoters. Accordingly, it was confirmed that this mutant was capable of functioning as a "2-input/AND-type" sensor capable of making an "arabinose/AHL" AND-type output to each of the arabinose promoter and the Lux promoter independently.

A method for the evaluation of the above-mentioned ligand responsiveness is specifically as described below.

200 μL of a measurement sample obtained by diluting the culture solution 10-fold with physiological saline was injected into a microwell plate (product manufactured by Nunc), and was measured for cell density when irradiated at 595 nm and fluorescence at 535 nm when excited at 485 nm, through use of FilterMaxF5 (commercially available absorbance/fluorescence detection apparatus, product manufactured by Molecular Devices). In addition, as a blank sample, 200 μL of a blank sample obtained by diluting cell-free liquid medium 10-fold with physiological saline was also subjected to measurement simultaneously. Data analysis was performed with a value obtained by subtracting the value of the blank sample from the measured value of the sample and performing correction for the dilution factor. The same applies to Examples 2-2, 2-3, 2-4, and 2-5 described below.

Example 2-2: Development Example 2 of 2-Input/AND-Type Output Sensor

Figure 3:
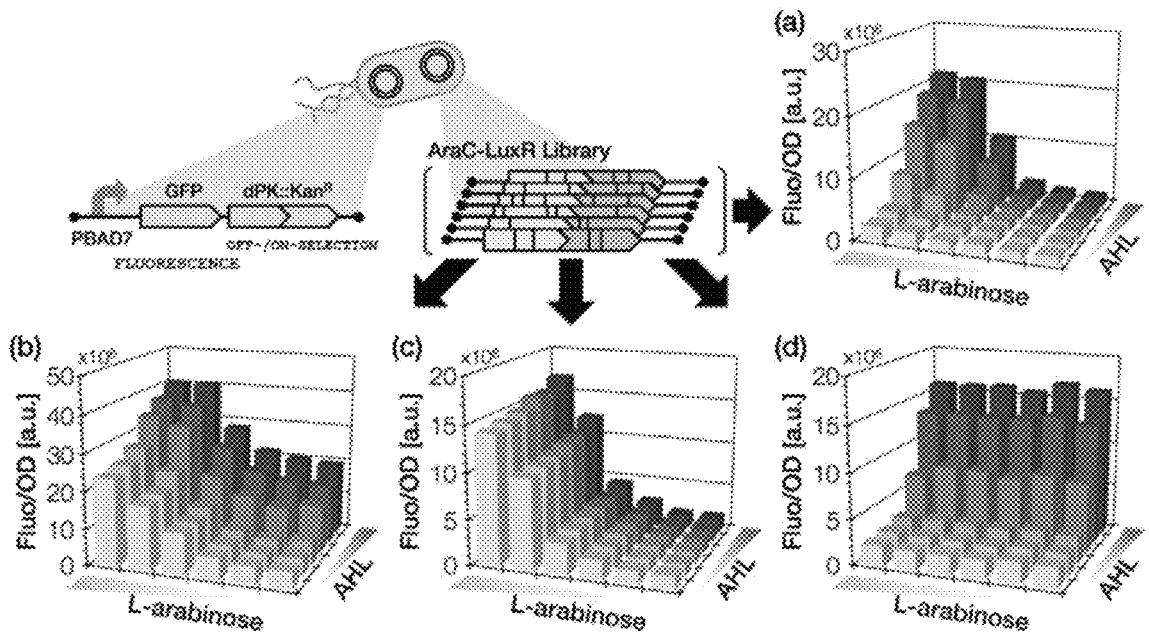
FIG. 3(a) shows ligand evaluation results of an AND gate-type genetic switch.
FIG. 3(b) shows ligand evaluation results of an OR gate-type genetic switch.
FIG. 3(c) shows ligand evaluation results of an $L_1$ only gate-type genetic switch.
FIG. 3(d) shows ligand evaluation results of an $L_2$ only gate-type genetic switch.

The full length of AraC-LuxR$_{N86K\ and\ C245W}$ was subjected to EP-PCR (50 μM MnCl$_2$, amplification factor: 10,000 times) to generate a mutant pool having random mutations introduced therein (the library size was 3×10$^6$). Unlike Example 2-1 described above, through use of P$_{BAD7}$-GFP as a reporter, 90 colonies were randomly picked (see FIG. 3). The ligand responsiveness of those colonies was evaluated. Specifically, culture was performed under separate conditions of "13 mM L-arabinose alone" and "13 mM L-arabinose+100 μM AHL", and 7 mutants each having an improved BOTH (L-arabinose+AHL)/L-arabinose ratio of 2 times or more were obtained. Fluorescence intensity measurement results of the mutant showing the highest BOTH/L-arabinose ratio among those mutants are shown in FIG. 3(a).

Through only one round of EP-PCR/screening, a mutant of AraC-LuxR$_{N86K\ and\ C245W}$ (see Table 5: P39R, I197N, and N252S) was able to be obtained.

Example 2-3: Development Example of 2-Input/OR-Type Output Sensor

The library illustrated in FIG. 2(c) is a mixture of mutants of AraC-LuxR$_{N86K\ and\ C245W}$ having various mutations. In this Example, screening was performed using a GFP reporter arranged downstream of P$_{BAD7}$, and it was confirmed that it was possible to obtain an "OR-type (logical sum-type)" biosensor that enhanced the reporter gene downstream of P$_{BAD}$ in the presence of one of arabinose and AHL unlike the 2-input/AND type (FIG. 2(d)). The details areas described below.

The full length of AraC-LuxR$_{N86K\ and\ C245W}$ was subjected to EP-PCR (50 μM MnCl$_2$, amplification factor: 10,000 times) to generate a mutant pool having random mutations introduced therein (the library size was 3×10$^6$). Through use of P$_{BAD7}$-GFP as a reporter, 90 colonies showing fluorescence on solid medium containing 10 μM AHL were picked. The ligand responsiveness of those colonies was evaluated. Specifically, culture was performed under separate conditions of "no ligand" and "10 μM AHL", and 2 mutants each having an improved AHL/none ratio of 3 times or more were obtained. Fluorescence intensity measurement results of the mutant showing the highest AHL/none ratio among those mutants are shown in FIG. 3(b).

Through only one round of EP-PCR/screening, a mutant of AraC-LuxR$_{N86K\ and\ C245W}$ (see Table 5: E295K) was obtained.

That is, a 2-input/OR-type sensor was able to be developed.

Example 2-4: Development Example 1 of 2-Input/1-Way Output-Type Sensor

In this Example, as an example of a 2-input/1-way output-type sensor, a genetic switch using P$_{BAD}$ as an "arabinose-only" gate that did not respond to AHL and was activated only with arabinose (showed a response thereto in a concentration-dependent manner) was developed. The details are as described below.

The full length of AraC-LuxR$_{N86K\ and\ C245W}$ was subjected to EP-PCR (50 μM MnCl$_2$, amplification factor: 10,000 times) to generate a mutant pool having random mutations introduced therein (the library size was 3×10$^6$). Through use of P$_{BAD7}$-GFP as a reporter, 90 colonies showing fluorescence on solid medium containing 13 mM L-arabinose were picked. The ligand responsiveness of those colonies was evaluated. Specifically, culture was performed under separate conditions of "13 mM L-arabinose" and "10 μM AHL", and 46 mutants each having an improved L-arabinose/AHL ratio of 2 times or more were obtained. Fluorescence intensity measurement results of a mutant having a high L-arabinose/AHL ratio and having low leaky expression in the presence of AHL alone among those mutants are shown in FIG. 3(c).

Through only one round of EP-PCR/screening, a mutant of AraC-LuxR$_{N86K\ and\ C245W}$ (see Table 5: M175K and K491E) was obtained.

That is, a 2-input/1-way output-type sensor was able to be developed.

Example 2-5: Development Example 2 of 2-Input/1-Way Output-Type Sensor

In this Example, as an example of a 2-input/1-way output-type sensor, a genetic switch using P$_{BAD}$ as an "AHL-only" gate that did not respond to arabinose and was activated only with AHL (showed a response thereto in a concentration-dependent manner) was developed.

First, mutations were introduced into amino acid residues required for arabinose recognition by the ligand (arabinose) binding site of AraC, to thereby reduce the affinity of AraC-LuxR for arabinose. Then, EP-PCR/screening was performed using a library having the thus reduced affinity. The details are as described below.

First generation: The L-arabinose binding residues of AraC-LuxR (H80, H81, and Y82) were randomized by a known method to generate a library (the library size was 3×10$^6$). Through use of P$_{BAD7}$-GFP as a reporter, 48 colonies showing fluorescence on solid medium containing 10 μM AHL were selected. The ligand responsiveness of those colonies was evaluated. Specifically, culture was performed under separate conditions of "no ligand", "13 mM L-arabinose", and "10 μM AHL", and 5 mutants each of which did not respond to L-arabinose and showed fluorescence when AHL was added were obtained. Of those, a mutant (H80F, H81K, and Y82L) having an AHL/none ratio and an L-arabinose/none ratio of 1.0 times and 1.6 times, respectively was adopted as a parent of a second generation.

Second generation: The full length of the mutant obtained in the first generation was subjected to EP-PCR (50 μM MnCl$_2$, amplification factor: 10,000 times) to generate a mutant pool having random mutations introduced therein (the library size was 5×10$^5$). Through use of P$_{BAD7}$-GFP as a reporter, 41 colonies showing intermediate to high levels of fluorescence were picked from a total of 1,600 colonies formed on solid medium containing 10 μM AHL. The ligand responsiveness of those colonies was evaluated. Specifically, culture was performed under separate conditions of "no ligand", "13 mM L-arabinose", and "10 μM AHL", and 5 mutants each of which did not respond to L-arabinose and had an AHL/none ratio of 2 times or more were obtained. Fluorescence intensity measurement results of the mutant having the highest AHL/none ratio among those mutants are shown in FIG. 3(d).

Through two rounds of screening (evolutionary engineering), a mutant of AraC-LuxR$_{N86K\ and\ C245W}$ (see Table 5: H80F, H81K, Y82L, N393I, Y439H, R523L, and F541L) was obtained.

That is, a 2-input/1-way output-type sensor different from that of Example 2-4 was able to be developed.

Example 3

Example 3: Development Example of 3-Input-Type Sensor

Generation of TetR-AraC-LuxR$_{N86K\ and\ C245W}$ Fusion

Figure 4:
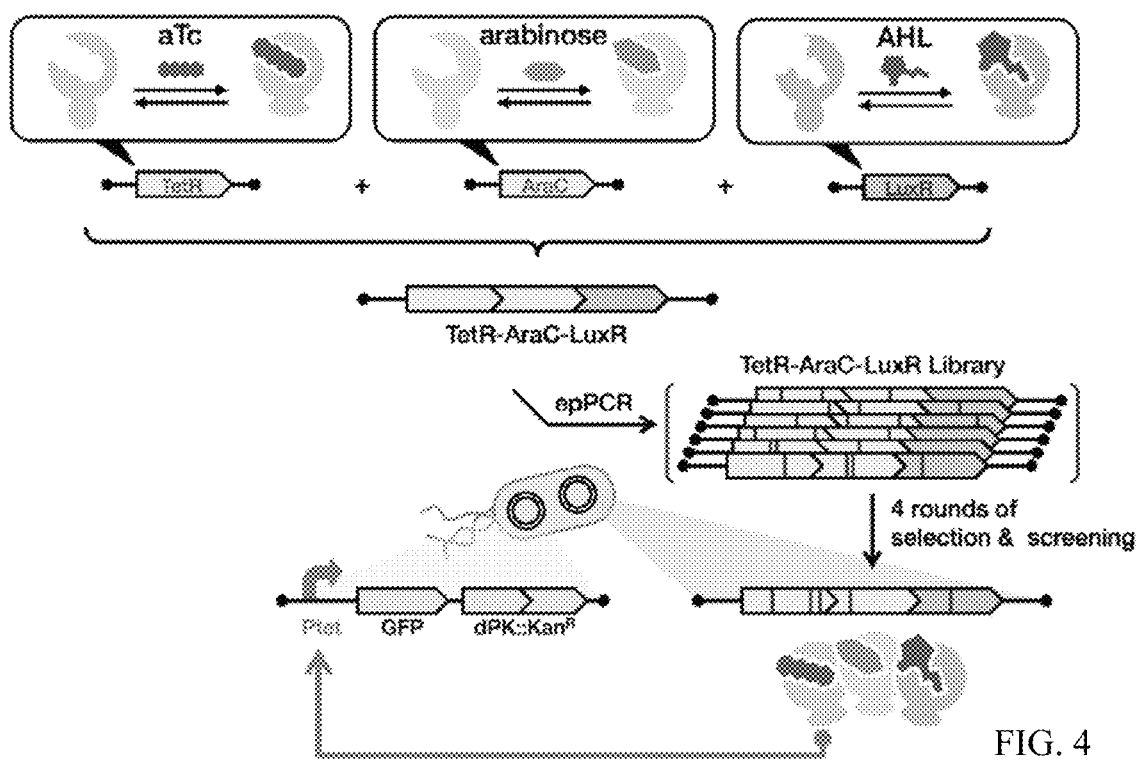
FIG. 4 is an outline of the generation of a fusion mutant of TetR-AraC-LuxR$_{N86K\ and\ C245W}$.

A 3-input-type sensor was developed on the basis of the 2-input-type sensor generated in Example 2. Another transcription factor, TetR (tetracycline-responsive transcription factor), was further fused to the N-terminus of the AraC-LuxR$_{N86K\ and\ C245W}$ fusion generated in Example 2 to generate TetR-AraC-LuxR$_{N86K\ and\ C245W}$ (see FIG. 4). It was confirmed that this three-transcription factor fusion protein (SEQ ID NO: 16) retained a function for each of target promoters. Further, it was confirmed that each transcription factor responded only to its corresponding target ligand (see FIG. 5(a)). Specifically, for TetP (Tet promoter), an action was exhibited by responding only to the target substance of TetR, i.e., aTc (anhydrotetracycline). That is, no response was made to arabinose or AHL.

Generation of Mutants of TetR-AraC-LuxR$_{N86K\ and\ C245W}$

Figure 15:
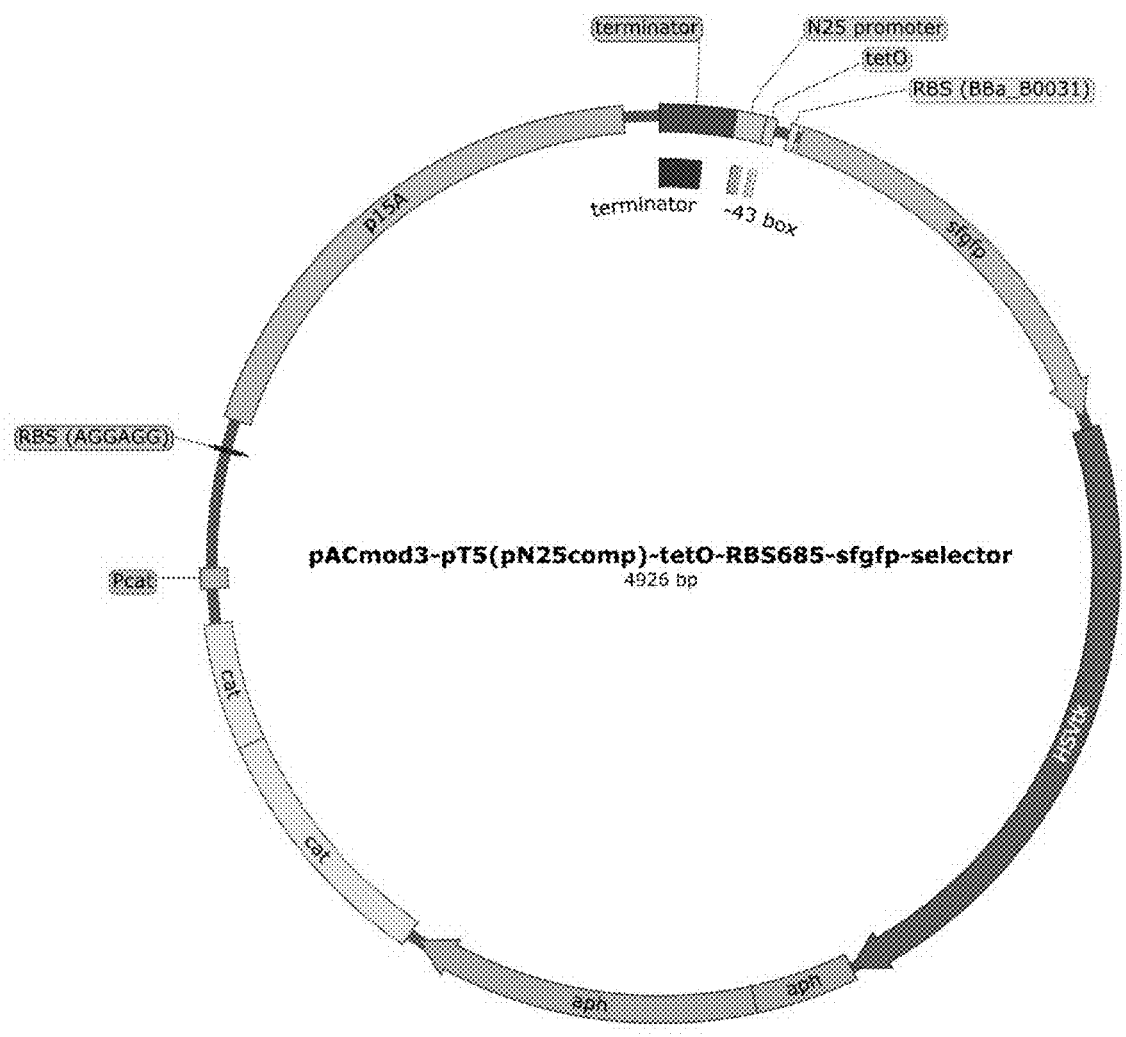
FIG. 15 is an outline of the plasmid structure of Ptet-GFP-TK::APH.

First generation: The full length of TetR-AraC-LuxR$_{N86K\ and\ C245W}$ (see FIG. 10) was subjected to EP-PCR (50 μM MnCl$_2$, amplification factor: 1,000) to generate a mutant pool having random mutations introduced therein (the library size was 1×10$^5$). Through use of P$_{tet}$-GFP (see FIG. 15: Ptet-GFP-TK::APH) as a reporter, 35 colonies showing weak fluorescence were picked from a total of 3,700 colonies formed on solid medium containing 216 nM aTc, 13 mM L-arabinose, and 10 μM AHL. The ligand responsiveness of those colonies was qualitatively evaluated by a spot method. In eight kinds of solid media obtained by combining the presence or absence of each ligand, it was confirmed that one mutant showed transcription repression when bound to all ligands. A TetR domain was fused again to AraC-LuxR$_{N86K\ and\ C245W}$ in order to remove base truncation that had been introduced into the above-mentioned mutant, and the resultant was adopted as a parent of a second generation.

Second generation: The full length of the mutant obtained in the first generation was subjected to EP-PCR (10 μM MnCl$_2$, amplification factor: 1,000 times) to generate a mutant pool having random mutations introduced therein (the library size was 7×10$^5$). Through use of P$_{lux}$-APH (Aminoglycoside phosphotransferase: kanamycin resistance gene) as a selector, selection was performed in order to remove mutants each having base truncation or a stop codon occurring therein (3 hours with 216 nM aTc, 13 mM L-arabinose, 10 μM AHL, and 30 μg/mL Kanamycin).

Next, through use of Ptet-GFP as a reporter, 8 colonies showing weak fluorescence were picked from a total of 2,000 colonies formed on solid medium containing 216 nM aTc, 13 mM L-arabinose, and 10 μM AHL. The ligand responsiveness of those colonies was qualitatively evaluated by a spot method. In eight kinds of solid media obtained by combining the presence or absence of each ligand, 3 mutants showed staged transcription repression and had no base truncation or stop codon occurring therein. Of those, a mutant suppressed in leaky expression under the condition of including all ligands was used as a parent of a third generation.

Third generation: The full length of the mutant obtained in the second generation was subjected to EP-PCR (10 μM MnCl$_2$, amplification factor: 1,000 times) to generate a mutant pool having random mutations introduced therein (the library size was 3×10$^4$). Through use of P$_{lux}$-APH as a selector, selection was performed in order to remove mutants each having base truncation or a stop codon occurring therein (3 hours with 216 nM aTc, 13 mM L-arabinose, 10 μM AHL, and 60 μg/mL kanamycin). Next, through use of Ptet-APH as a selector, selection was performed in order to concentrate mutants showing weakened transcription repression activity with the addition of aTc alone (3 hours with 216 nM aTc and 30 μg/mL kanamycin). Further, through use of Ptet-GFP as a reporter, 184 colonies showing weak fluorescence were picked from a total of 384 colonies formed on solid medium containing 216 nM aTc, 13 mM L-arabinose, and 10 μM AHL. The ligand responsiveness of those colonies was evaluated. Specifically, culture was performed under separate conditions of "no ligand", "216 nM aTc alone", and "216 nM aTc, 13 mM L-arabinose, and 10 μM AHL", and 5 mutants showed high transcription repression when all ligands were added, while showing weak transcription repression with aTc alone. The 5 mutants all had similar functions, but had different mutation sites, and hence all of these mutants were used as parents of a fourth generation.

Figure 5:
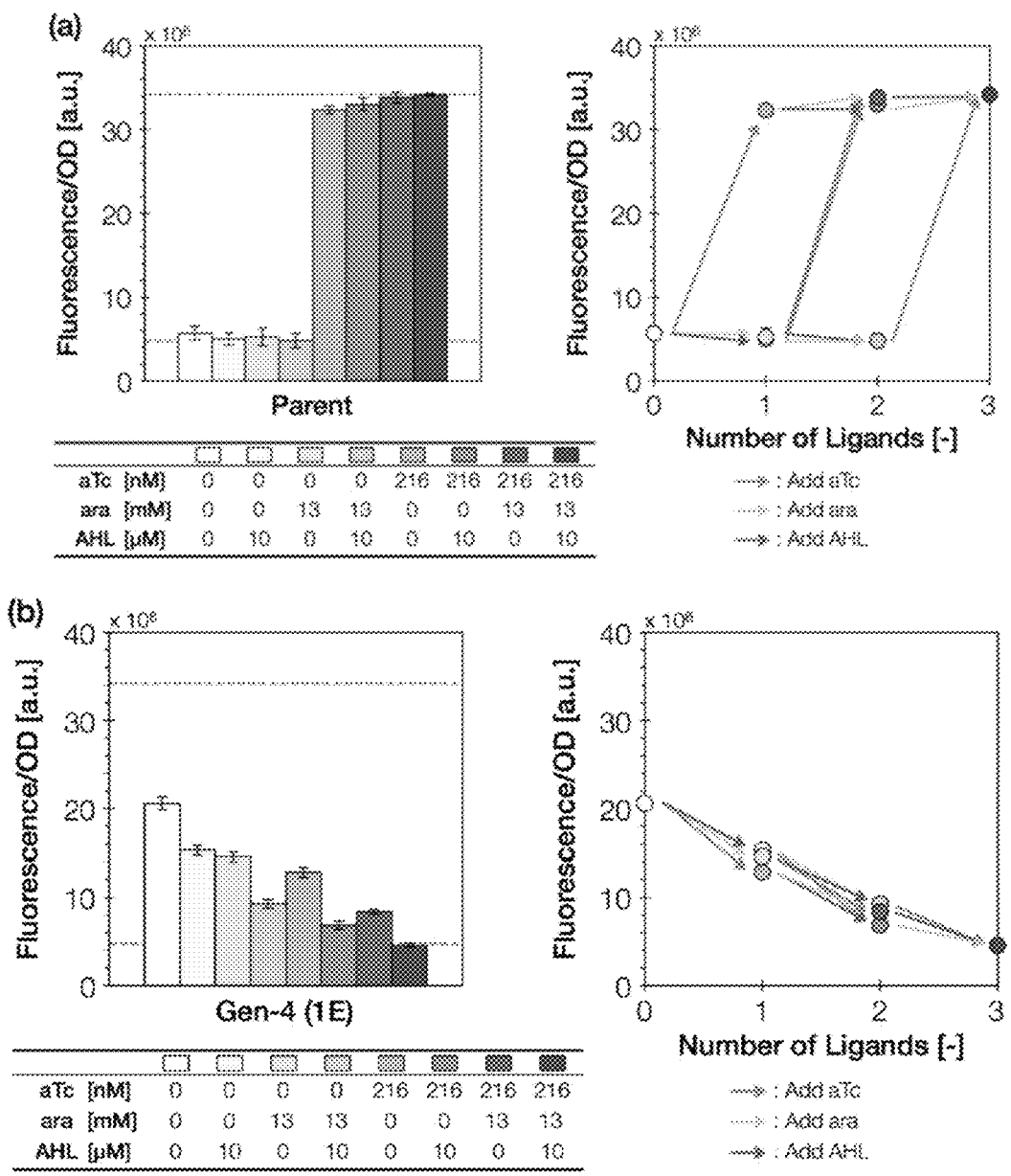
FIG. 5(a) shows ligand evaluation results of the TetR-AraC-LuxR$_{N86K\ and\ C245W}$ fusion (before mutation introduction)
FIG. 5(b) shows ligand evaluation results of a 3-input-type 4-stage output reduction-type genetic switch.

Fourth generation: the five mutants obtained in the third generation were mixed and the full length was subjected to EP-PCR (10 μM MnCl$_2$, amplification factor: 1,000 times) to generate a mutant pool having random mutations introduced therein (the library size was 2×10$^4$). Through use of P$_{lux}$-APH as a selector, selection was performed in order to remove mutants each having base truncation or a stop codon occurring therein (3 hours with 216 nM aTc, 13 mM L-arabinose, 10 μM AHL, and 30 μg/mL Kan). Further, through use of Ptet-APH as a selector, selection was performed in order to concentrate mutants showing weakened transcription repression activity with the addition of aTc alone (3 hours with 216 nM aTc and 30 μg/mL Kan). Next, through use of Ptet-GFP as a reporter, 45 colonies showing weak fluorescence were picked from a total of 900 colonies formed on solid medium containing 216 nM aTc, 13 mM L-arabinose, and 10 μM AHL. The ligand responsiveness of those colonies was qualitatively evaluated by a spot method. In eight kinds of solid media obtained by combining the presence or absence of each ligand, 3 mutants were improved in transcription repression activity as the number of ligands increased. Those 3 mutants have the same mutations introduced therein, and fluorescence intensity measurement results of one of the mutants are shown in FIG. 5(b).

Through four rounds of screening (evolutionary engineering), a mutant of TetR-AraC-LuxR$_{N86K\ and\ C245W}$ (see Table 5: K46R, D95G, K108N, I134V, V145A, L204P, I214N, P216T, F217S, L409Q, T545A, and S569T) was obtained.

That is, a 3-input-type sensor (in particular, 3-input-type 3-stage output reduction sensor) was able to be developed.

TABLE 5

Mutation sites of mutants

| Name | See | Non-Synonymous Mutation | Synonymous Mutation |
|---|---|---|---|
| pluxAND 4-9G | FIG. 2(d) | T220C (F74L), C256A (P86T), T746C (V249A), A893T (N298I) | A1221G (K407K), A1536G (T521T) |
| AND 4-2A | FIG. 3(a) | C116G (P39R), T590A (I197N), A755G (N252S) | A1104G (L368L), A1200T (P400P) |
| OR 4-9G | FIG. 3(b) | G883A (E295K) | T192C (F64F) A801G (K267K) |
| ARA 4-5H | FIG. 3(c) | T524A (M175K), A1471G (K491E) | T1449C (C483C), T1518C (T506T) |
| AHL Gen2-4-8B | FIG. 3(d) | TTT (H80F), AAG (H81K), TTG (Y82L), A1178T (N393I), T1315C (Y439H), G1568T (R523L), T1621C (F541L) | C864T (A288A), A1167T (I389I) |
| TAL Gen 4-1E | FIG. 5(b) | A137G (K46R), A284G (D95G), A324T (K108N), A400G (I134V), T434C (V145A), T611C (L204P), T641A (I214N), C646A (P216T), T650C (F217S), T1226A (L409Q), A1633G (T545A), T1705A (S569T) | G1263A (Q421Q), T2160C (G720G) |

Example 4

In this Example, in order to ascertain that the 2-input-type sensor developed in the foregoing was capable of functioning as a genetic switch in a combination other than AraC and LuxR, ArsR, which was known as an arsenic sensor, was used in place of the arabinose sensor (AraC). The details are as described below (see FIG. 6(a)).

As an arsenic standard solution (hereinafter As(III)), an arsenic standard solution (As 1000) was purchased from Wako Pure Chemical Industries, Ltd. and used in this Example.

Figure 11:
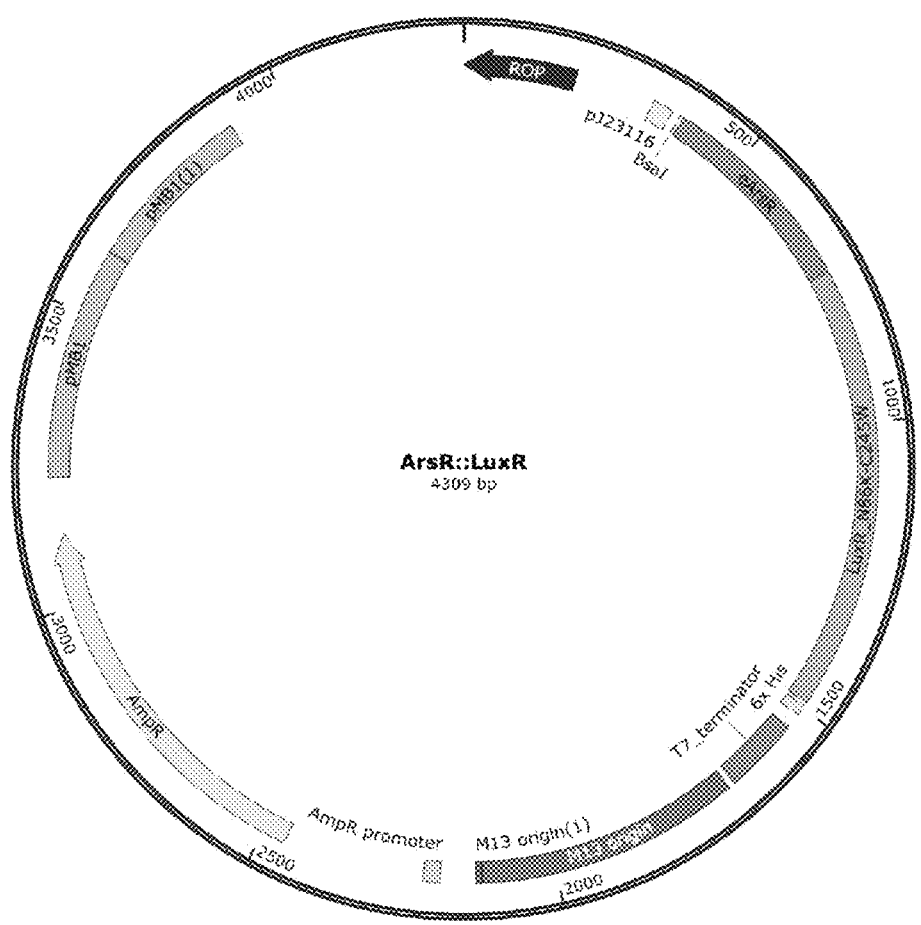
FIG. 11 is an outline of the plasmid structure of ArsR::LuxR$_{N86K\text{-}C245W}$.

(1-1) Generation of ArsR::LuxR$_{N86K\ and\ C245W}$ (SEQ ID NO: 17) (see FIG. 11)

(1-1-1) Preparation of Vector for ArsR::LuxR$_{N86K\ and\ C245W}$

Plasmid 1 (see Table 7) was subjected to PCR (KOD plus) treatment with Primers 1 and 2 (see Table 6: SEQ ID NOS: 1 and 2) to give a PCR product. Next, the PCR product was subjected to DpnI treatment and then subjected to gel extraction. The extract was subjected to digestion with XhoI (commercially available restriction enzyme) and SpeI-HF (commercially available restriction enzyme), and further subjected to gel extraction.

Figure 12:
FIG. 12 is an outline of the plasmid structure of ArsR.

(1-1-2) Preparation of ArsR Domain (see FIG. 12)

The genome of the *E. coli* strain MG1655 was used as a template and subjected to PCR (KOD plus) treatment with Primers 3 and 4 (see Table 6: SEQ ID NOS: 3 and 4) to give a PCR product. Next, the PCR product was subjected to DpnI treatment and then subjected to gel extraction. The extract was subjected to digestion with XhoI and SpeI-HF, and further subjected to gel extraction.

(1-1-3) Recovery of ArsR::LuxR$_{N86K\ and\ C245W}$

The vector fragment of the section "1-1-1" and the insert fragment of the section "1-1-2" were subjected to ligation. Next, XL10-Gold (commercially available competent cells) was transformed with the ligation product, and clones were recovered.

(1-2) Generation of ArsR (1-2-1) Preparation of Vector Side

Plasmid 1 (see Table 7) was subjected to PCR (KOD plus) treatment with Primers 1 and 2 (see Table 6) to give a PCR product. Next, the PCR product was subjected to DpnI treatment and then subjected to gel extraction. The extract was subjected to digestion with XhoI and SpeI-HF, and further subjected to gel extraction.

(1-2-2) Preparation of Insert Side

The genome of the *E. coli* strain MG1655 was used as a template and subjected to PCR (KOD plus) treatment with Primers 3 and 5 (see Table 6: SEQ ID NOS: 3 and 5) to give a PCR product. Next, the PCR product was subjected to DpnI treatment and then subjected to gel extraction. The extract was subjected to digestion with XhoI and SpeI-HF, and further subjected to gel extraction.

(1-2-3) Recovery of ArsR

The vector fragment of the section "1-2-1" and the insert fragment of the section "1-2-2" were subjected to ligation. Next, XL10-Gold was transformed with the ligation product, and clones were recovered.

(1-4) Generation of P$_{ars}$-GFP (1-4-1) Generation of P$_{ars}^{[rbs]}$GFP Library Plasmid 2 (see Table 7) was used as a template and subjected to PCR (KOD plus) treatment with Primers 6 and 7 (see Table 6: SEQ ID NOS: 6 and 7) to give a PCR product. Next, the PCR product was subjected to gel extraction. The gel extraction product was subjected to the Golden Gate method using a commercially available product to assemble DNA fragments, followed by column purification. XL10-Gold was transformed with the purified Golden Gate product and then subjected to liquid culture, and an RBS library was recovered.

(1-4-2) Recovery of P$_{ars}$-GFP Having Appropriate RBS (Pars-GFP Having Such RBS as to Show High Fluorescence Under ArsR Expression Plasmid-Free Condition)

*E. coli* MG1655 was cotransformed with the RBS library of the section "1-4-1". Next, from colonies isolated on solid medium, one showing strong fluorescence was selected, and cultured overnight. Next, a P$_{ars}$-GFP plasmid was recovered from the culture solution. Further, *E. coli* MG1655 was cotransformed with the recovered P$_{ars}$-GFP and ArsR (Plasmid 4: see Table 7). Next, colonies on solid medium were isolated, and confirmed to show weak fluorescence as compared to the one showing strong fluorescence obtained from the above-mentioned colonies.

TABLE 6

| No. | Name | Sequence | Note |
| --- | --- | --- | --- |
| 1 | SpeI-lux-Fwd | TTTT ACTAGT GAAAACATAAATGCCGACGACACA | Fwd primer for PCR of vector for ArsR-LuxR |
| 2 | SpeI-tetR-Rev | TTTT ACTAGT GGACCCACTTTCACATTTAAGTTGTTTTT | Rev primer for PCR of vector for ArsR-LuxR |
| 3 | pET23d-XhoI-Fwd | TTTT CTCGAG ATGTCATTTCTGTTACCCATCCAATTGTTC | Fwd primer for PR of ArsR domain and ArsR insert |
| 4 | SpeI-eArsR-Rev | TTTT ACTAGT ACTGCAAATGTTCTTACTGTCCCCG | Rev Primer for PCR of ArsR domain |
| 5 | BamHI-eArsR-Rev | TTTT GGATCC ACTGCAAATGTTCTTACTGTCCCCG | Rev primer for PCR of ArsR insert |
| 6 | pACmod3 PT5-arsO-sfgfp Rev | TTTT GGTCTC a AAACATATATGACTTAACGAATGTGTATT ATACAGAAAAATTTTCCTGAAAGCAAATAAATTT TTCATG | Rev primer for PCR of $P_{ars}$-GFP |
| 7 | pACmod3 PT5-arsO-sfgfp Fwd | TTTT GGTCTC a GTTTTGACTTTAGCACGAGCTSAA KAATACARGRAGACKMTCAATGGGGTCTAAAGGC GAAGAAC | Fwd primer for PCR of $P_{ars}$-GFP |
| 8 | BamHI-His-Fwd | TTTT GGATCC CATCATCACCATCAC | |
| 9 | luxR-seq-Rev-1 | AGCATTCCGAAGCCATTGTTAGC | |
| 10 | ROP-seq-Fwd | GATAAAGCGGGCCATGTTAAGG | |
| 11 | Y-T7tn-gfp-sq-R | TCAGCAAAAAACCCCTCAAGACCCGTTTA | |
| 12 | pUc vector Rev (KpnI) | TTTT GGTACCCCTGGGGTGCCTAATGAGTG | |
| 13 | pUC vector Fwd (HindIII) | TTTT AAGCTTCATATGGTGCACTCTCAGTACAATC | |
| 14 | Pet23d-Fwd (KpnI) | TTTT GGTACCGTGAGGGTAAACAACTGGCG | |
| 15 | prpC-luxR-Fwd | GTTATATCTCGGAGGTTTAC ATGAGCGACACAACGATCCT | Fwd primer for PCR of PrpC domain |
| 16 | prpC-luxR-Fwd | TCGGCATTTATGTTTTCACTAGT CTGGCGCTTATCCAGCG | Fwd primer for PCR of PrpC domain |
| 17 | prpD-luxR-Fwd | GTTATATCTCGGAGGTTTAC ATGTCAGCTCAAATCAACAACATC | Fwd primer for PCR of PrpD domain |
| 18 | prpD-luxR-Fwd | | Fwd primer for PCR of PrpD domain |
| 19 | mTagBFP Fwd | CCATTTGATCGCAAATATCAAGACG | |
| 20 | pMCvec-Plux-ApaI PCR1 Rev | TTTATTCGACTATAACAAACCATTTTCTTGCGTA AACCTGTACGATCCTACAGGTGGTACC TATAAACGCAGAAAG | |
| 21 | pMCvec-Plux-ApaI PCR2 Rev | TTTT GGGCCC TTTATTCGACTATAACAAACCATTTTCTTGCG | |
| 22 | sfGFP standard PBS library Fwd (ApaI-XhoI) | TTTT GGGCCC RMSCYYTAWGGAGGY CTCGAG ATGGGGTCTAAAGGCGAAGAAC | |
| 23 | aph-HindIII Rev | TTTT AAGCTT A TCAAGAAGAACTCGTCAAGAAGGC | |
| 24 | Fusion-ml-inv-Fwd | CATCATCACCATCACCACTAATGAA | Fwd primer for amplifying vector for library plasmid |
| 25 | Fusion-ml-inv-Rev | GTAAACCTCCGAGATATAACTAGAG | Fwd primer for amplifying vector for library plasmid |
| 26 | Fusion-mutlibrary-Fwd | CTCTAGTTATATCTCGGAGGTTTAc | Fwd primer for generating mutant libraries of PrpC-LuxR and PrpD-LuxR |

TABLE 6-continued

| No. | Name | Sequence | Note |
|---|---|---|---|
| 27 | Fusion-mutlibrary-Rev | TTCATTAGTGGTGATGGTGATGATG | Rev primer for generating mutant libraries of PrpC-LuxR and PrpD-LuxR |

TABLE 7

Figure 13:
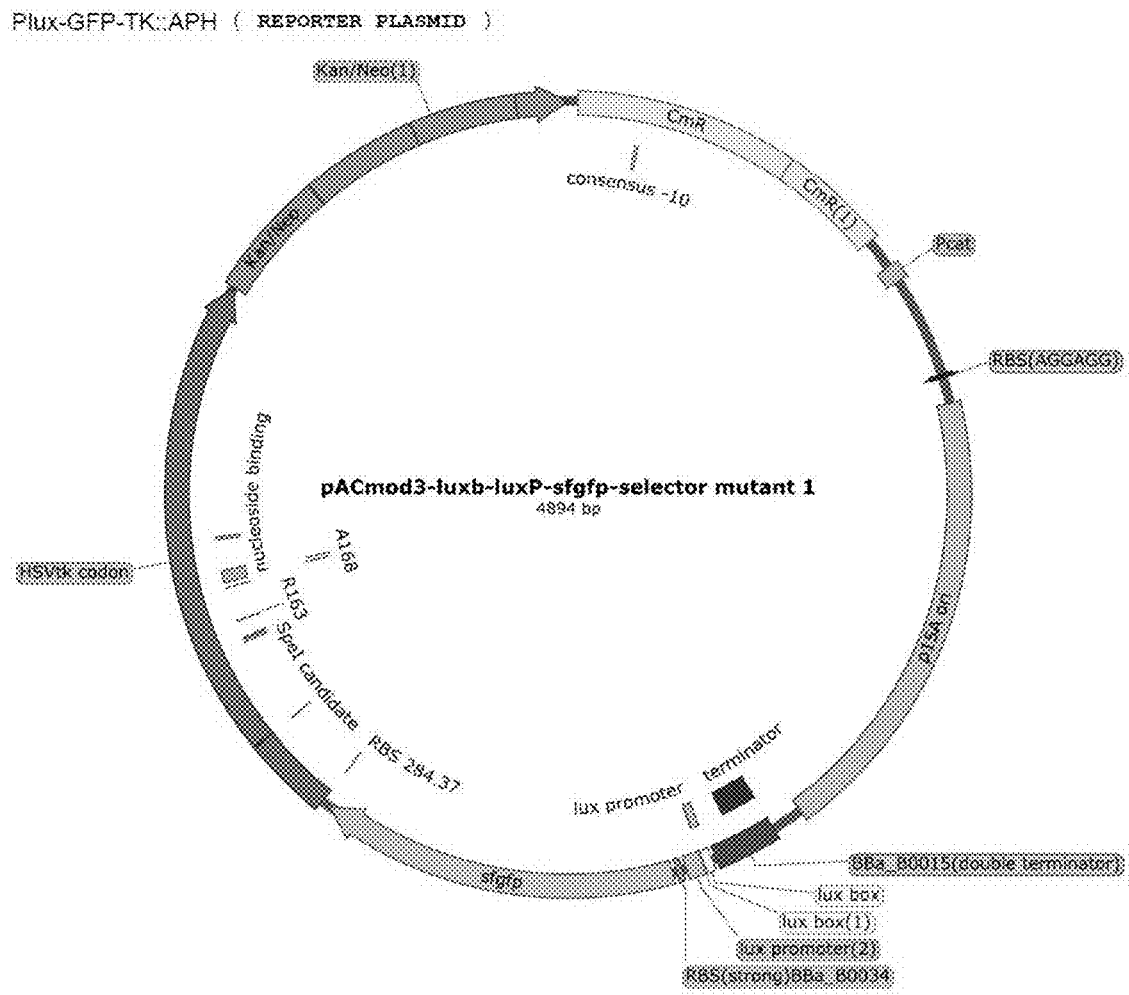
FIG. 13 is an outline of the plasmid structure of Plux-GFP-TK::APH.
Figure 14:
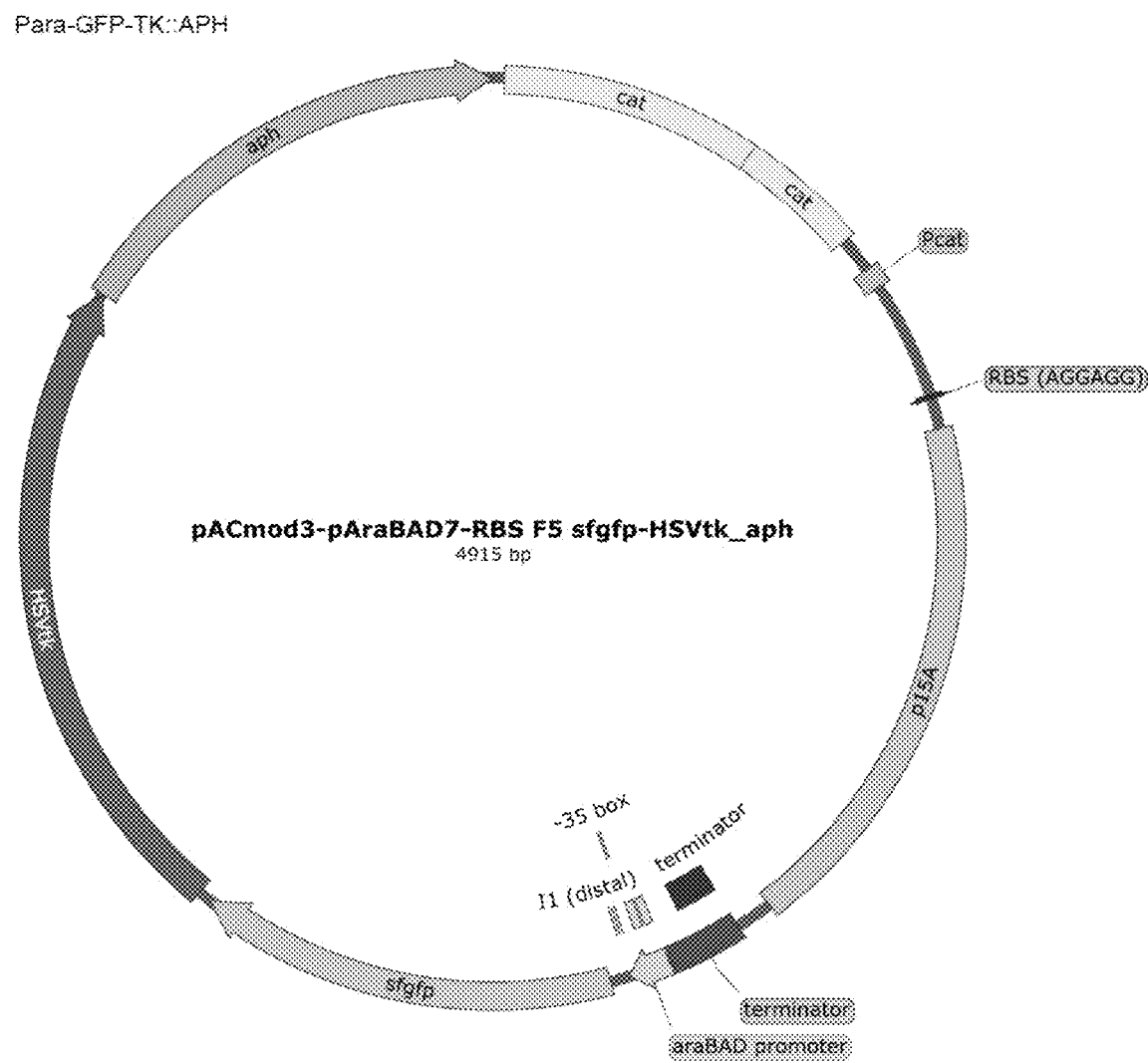
FIG. 14 is an outline of the plasmid structure of Para-GFP-TK::APH.

| No. | Name | Construct |
|---|---|---|
| 1 | TL (Tet R-LuxR$_{N86K\ and\ C245W}$) | pET23d-P$_{J23116}$-tetR::luxR$_{N86K\text{-}C245W}$::his |
| 2 | GFP | pACmod3-P$_{T5}$-sfgp-HSVtk:aph |
| 3 | ArsR::LuxR (FIG. 11) | pET23d-P$_{J23116}$-arsR::luxR$_{N86K\text{-}C245W}$::his |
| 4 | ArsR (FIG. 12) | pET23d-P$_{J23116}$-arsR::his |
| 5 | P$_{lux}$-GFP (FIG. 13) | pACmod3-P$_{lux}$-sfgfp-HSVtk:aph |
| 6 | P$_{ars}$-GFP (FIG. 14) | pACmod3-P$_{TS/arsO}{}^{high}$sfgfp-HSVtk:aph |
| 7 | ArsR::LuxR | pET23d-P$_{J23116}$-(arsR::luxR)::his |
| 8 | pUC-TAL | pUC19-P$_{J23116}$-tal::his |
| 9 | pUC-ArsR | pUC19-P$_{J23116}$-arsR::his |
| 10 | pUC-ArsR::LuxR | pUC19-P$_{J23116}$-(arsR::luxR)::his |
| 11 | pUC-phi | pUC19-P$_{J23116}$-phi |
| 12 | AL (AraC-LuxR$_{N86K\ and\ C245W}$) | pET23d-P$_{J23116}$-araC::luxR$_{N86K\text{-}C245W}$ |
| 13 | pMC-P$_{lux}$-GFP | pMC-P$_{lux}$-sfgfp-HSVtk::aph |
| 14 | pET23d-PrpC::LuxR | pET23d-P$_{J23116}$-(prpC::luxR$_{N56K\text{-}C245W}$)::his |
| 15 | pET23d-PrpD::LuxR | pET23d-P$_{J23116}$-(prpD::luxR$_{N86K\text{-}C245W}$)::his |
| 16 | pMC-BFP | pMC-P$_{N25}$-mTagBFP |
| 17 | LuxR | pTrcHis2-P$_{tra}$-luxR |
| 18 | pET23d-PrpC::LuxRmut | pET23d-P$_{J23116}$-(prpC$_{K318R}$::luxR$_{N86K\text{-}C245W}$)::his |
| 19 | pET23d-PrpD::LuxRmut | pET23d-P$_{J23116}$-(prpD$_{S163T\text{-}A225G\text{-}I285V}$::luxR$_{N86K\text{-}C245W}$)::his |

(2-1) Generation of ArsR::LuxR Library (2-1-1) Preparation of Vector Fragment

Plasmid 3 (see Table 7) was used as a template and subjected to PCR (KOD plus) treatment with Primers 8 and 9 (see Table 6: SEQ ID NOS: 8 and 9) to give a PCR product. Next, the PCR product was subjected to DpnI treatment and then subjected to gel extraction. The extract was subjected to digestion with XhoI, BamHI-HF, and rSAP, and further subjected to gel extraction.

(2-1-2) Preparation of ArsR::LuxR Fragment Having Random Mutations Introduced Throughout Entire Gene Plasmid 3 (see Table 7) was used as a template and subjected to PCR (KOD plus) treatment with Primers 10 and 11 (see Table 6: SEQ ID NOS: 10 and 11) to give a PCR product. Next, the PCR product was subjected to DpnI treatment and then subjected to gel extraction. The gel extraction product was used as a template and subjected to PCR (Taq, 10 μM or 50 μM MnCl$_2$) treatment with Primers 10 and 11 (see Table 6) to give a PCR product. Next, the PCR product was subjected to gel extraction. The extract was subjected to digestion with XhoI and BamHI-HF, and further subjected to gel extraction.

(2-1-3) Recovery of ArsR::LuxR Library

The vector fragment of the section "2-1-1" and the insert fragment of the section "2-1-2" were subjected to ligation. Next, the ligation product was subjected to column purification. Next, an E. coli strain BW25113 was trans formed with the purified ligation product and subjected to liquid culture, and a library was recovered from the resultant culture solution.

(2-2) Evaluation of Reporter (GFP) Expression Amount

MG1655 was transformed with an arbitrary reporter plasmid. Next, one transformant was selected, and competent cells (E. coli) were generated. The E. coli was transformed with the library (plasmids). An arbitrary number of isolated colonies were selected, and subjected to liquid culture overnight. A1/100 amount of the preculture solution was inoculated into liquid medium containing As(III) or AHL at an arbitrary concentration, and was cultured for 12 hours. Next, 200 μL of a measurement sample obtained by diluting the culture solution 10-fold with physiological saline was prepared. Cell density (OD$_{595}$) and fluorescence at 535 nm at the time of excitation at 485 nm were measured using FilterMax F5 (commercially available absorbance detection apparatus). As a blank sample (control), 200 μL of a blank sample obtained by diluting liquid medium 10-fold with physiological saline was also subjected to measurement simultaneously. Data analysis was performed with a value obtained by subtracting the measured value of the blank sample from the measured value of the sample.

(2-3) Selection of ArsR::LuxR Library

MG1655 was transformed with a reporter P$_{lux}$-GFP (Plasmid 5: see Table 7). Then, one transformant was selected, and competent cells (E. coli) were generated. The E. coli was transformed with the ArsR::LuxR library of the section "2-1", inoculated into 10 mL of liquid medium, and cultured overnight. Next, the preculture solution in an amount corresponding to 10$^7$ cells was inoculated into 10 mL of liquid medium containing 1 μM AHL and 5,000 ppb (67 μM) As(III), and was cultured for 1 hour. Next, 100 μg/mL kanamycin was added, followed by culture for 3 hours. Next, the culture solution was centrifuged and the supernatant was removed. Further, the resultant was resuspended in 10 mL of liquid medium containing 1 μM AHL and 5,000 ppb (67 μM) As(III). The culture solution was again centrifuged and the supernatant was removed (an operation of removing kanamycin was performed). The operation of removing kanamycin was performed again. Next, the resultant was resuspended in 10 mL of liquid medium containing 1 μM AHL and 5,000 ppb (67 μM) As(III), and was cultured overnight. Finally, cells were collected from the culture solution to recover concentrated library plasmids.

(3-1) Generation of High-Sensitivity 2-Input AND-Type Arsenic Switch (ArsR-LuxR)

MG1655 was transformed with a reporter plasmid $P_{lux}$-GFP (Plasmid 5: see Table 7). Next, one transformant was selected, and competent cells (*E. coli*) were generated. The competent cells (*E. coli*) were transformed with the ArsR-LuxR library of the section "2-1". 89 of colonies formed on solid medium were randomly selected.

Fluorescence intensities per cell density in the case of culture under separate conditions of "medium containing 1 μM AHL" and "medium containing 1 μM AHL and 5,000 ppb As(III)" were evaluated by the method of the section "2-2". A mutant showing weak fluorescence under the condition of adding AHL alone, and showing strong fluorescence under the condition of adding AHL and As(III) was recovered.

The recovered mutant was used as a template to generate a library by the method of the section "2-1". The competent cells (*E. coli*) were transformed with the generated library. 59 of colonies formed on solid medium were randomly selected. Fluorescence intensities per cell density in the case of culture under separate conditions of "medium containing 1 μM AHL" and "medium containing 1 μM AHL and 5 ppb As(III)" were evaluated by the method of the section "2-2". A mutant showing weak fluorescence under the condition of adding AHL alone, and showing strong fluorescence under the condition of adding AHL and As(III) was recovered.

Figure 6:
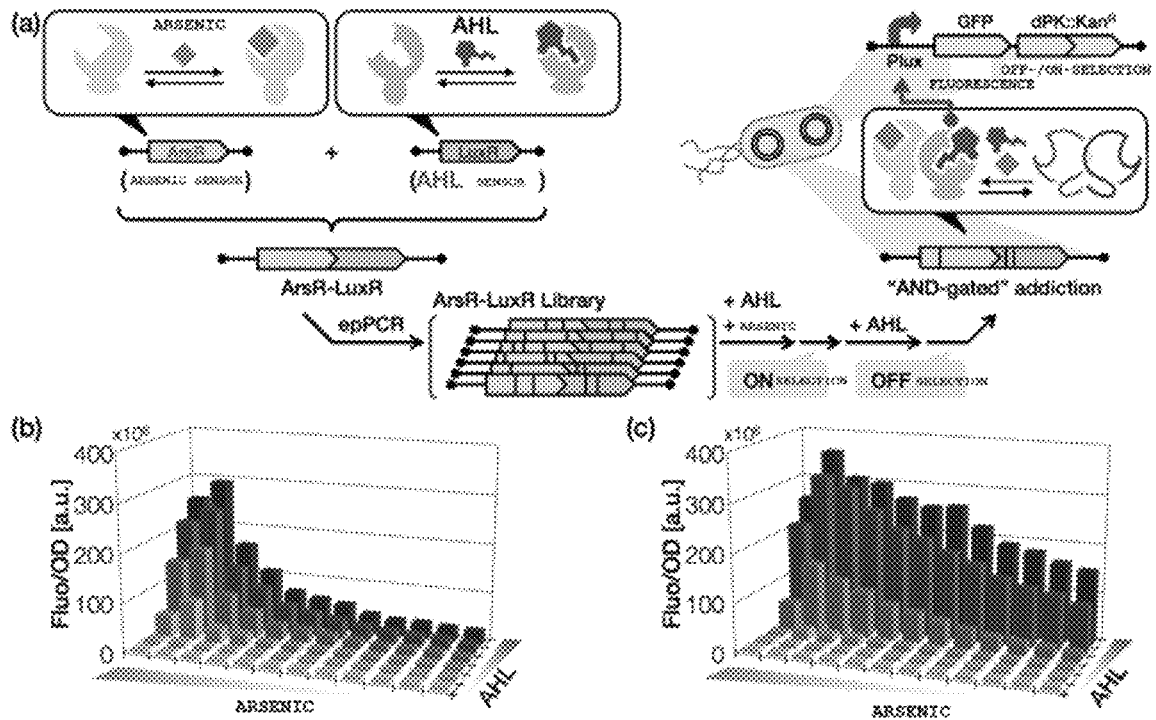
FIG. 6(a) is an outline of the generation of a fusion mutant of ArsR::LuxR$_{N86K-C245W}$
FIG. 6(b) shows ligand evaluation results of an AND-type arsenic switch having high stringency.
FIG. 6(c) shows ligand evaluation results of a high-sensitivity AND-type arsenic switch.

It was confirmed by the method of the section "2-2" that a high-sensitivity AND-type arsenic switch had been generated (see FIG. 6(*c*)).

(3-2) Generation of 2-Input AND-Type Arsenic Switch Having High Stringency (ArsR-LuxR)

MG1655 was transformed with a reporter-plasmid $P_{lux}$-GFP (Plasmid 5: see Table 7). Next, one transformant was selected, and competent cells (*E. coli*) were generated. The competent cells (*E. coli*) were transformed with the ArsR-LuxR library of the section "2-1".

Mutants showing fluorescence when 1 μM AHL and 5,000 ppb As(III) were added were concentrated by the method of the section "2-3". Next, the competent cells (*E. coli*) were transformed with the concentrated library. Next, 80 colonies showing weak fluorescence on solid medium containing 1 μM AHL were selected.

Fluorescence intensities per cell density in the case of culture under separate conditions of "medium containing 1 μM AHL", "medium containing 1 μM AHL and 5 ppb As(III)", and "medium containing 1 μM AHL and 500 ppb As(III)" were evaluated by the method of the section "2-2". A mutant showing weak fluorescence under the condition of adding AHL alone, and showing strong fluorescence under the condition of adding AHL and 5 ppb As(III) and under the condition of adding AHL and 500 ppb As(III) was recovered.

It was confirmed by the method of the section "2-2" that an AND-type arsenic switch having high stringency had been generated (see FIG. 6(*b*)).

(Evaluation of Arsenic Responsiveness of ArsR/$P_{ars}$)

In this Example, the performance of a 2-input AND-type arsenic switch in the case of not using $P_{lux}$ in a reporter plasmid was evaluated.

(4-1) Change to pUC Vector (4-1-1) Preparation of Vector pUC-TAL (Plasmid 8: see Table 7, TetR-AraC-LuxR$_{N86K\ and\ C245W}$) was used as a template and subjected to PCR (KOD plus) treatment with Primers 12 and 13 (see Table 6: SEQ ID NOS: 12 and 13) to give a PCR product. Next, the PCR product was subjected to gel extraction. The extract was subjected to digestion with KpnI-HF (known restriction enzyme), HindIII-HF, and rSAP, and further subjected to gel extraction.

(4-1-2) Preparation of Insert

ArsR and ArsR::LuxR (Plasmids 4 and 7: see Table 7) were each used as a template and subjected to PCR (KOD plus) treatment with Primers 11 and 14 (see Table 6: SEQ ID NOS: 11 and 14) to give a PCR product. Next, the PCR product was subjected to gel extraction. The extract was subjected to digestion with KpnI-HF and HindIII-HF, and further subjected to gel extraction.

(4-1-3) Recovery of pUC Product

The vector fragment of the section "1-2-1" and the insert fragment of the section "1-2-2" were subjected to ligation. Next, XL10-Gold was transformed with the ligation product, and clones were recovered.

(4-2) Arsenic Responsiveness Evaluation with $P_{ars}$-GFP (See FIG. 16)

MG1655 was transformed with a reporter plasmid $P_{ars}$-GFP (Plasmid 6: see Table 7). One transformant was selected, and competent cells (*E. coli*) were generated.

The competent cells (*E. coli*) were transformed with pUC-ArsR, pUC-ArsR::LuxR, or pUC-phi (Plasmids 9 to 11: see Table 7). Three of colonies formed on solid medium were randomly selected.

Figure 8:
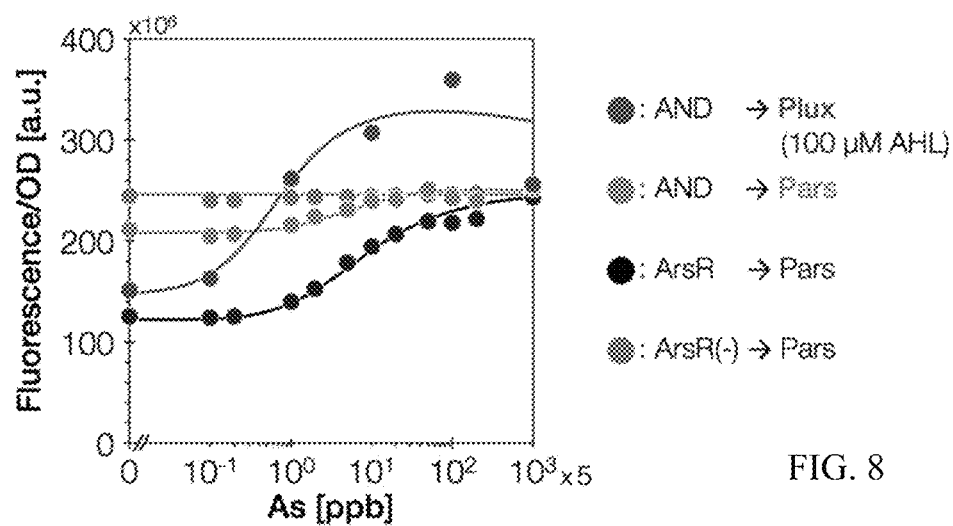
FIG. 8 shows arsenic concentration detection results in various switches {"AND→Plux" represents "pUC-ArsR::LuxR"/"pAC-PLux-GFP", "AND→Pars" represents "pUC-ArsR::LuxR"/"pAC-Pbad-GFP", "ArsR→Pars" represents "pUC-ArsR"/"pAC-Pbad-GFP", and "ArsR(-)→Pars" represents "pUC-phi"/"pAC-Pbad-GFP"}.

Fluorescence intensities per cell density in the case of culture in the presence of 100 μM AHL and at arbitrary different As(III) concentrations were evaluated by the method of the section "2-2" (see FIG. 8).

Example 5

(Selection Method for Sensitivity-Variable Genetic Switch)

Figure 2:
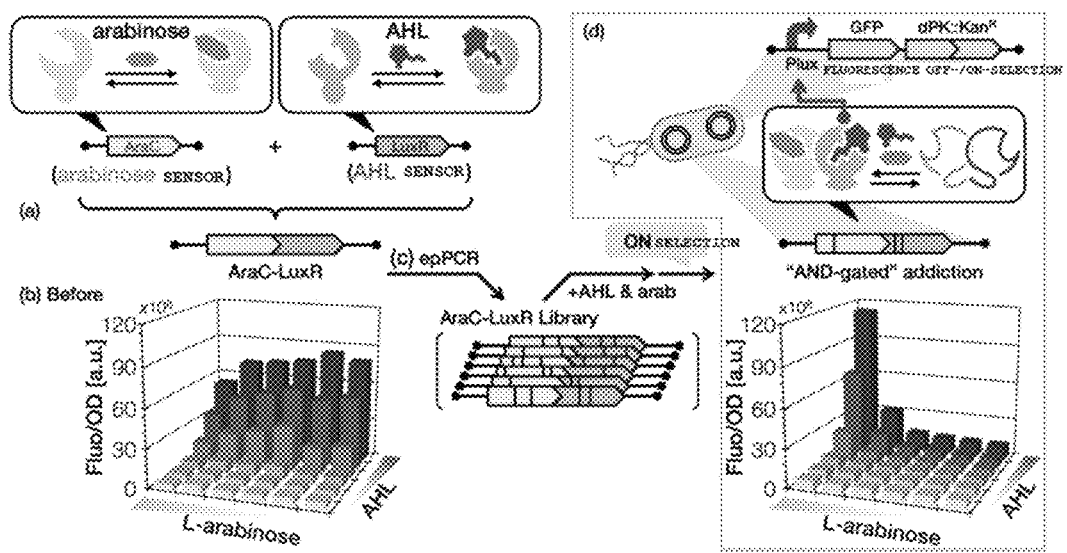
FIG. 2(a) is an illustration of an AraC-LuxR$_{N86K\ and\ C245W}$ fusion.
FIG. 2(b) shows ligand evaluation results of the AraC-LuxR$_{N86K\ and\ C245W}$ fusion (before mutation introduction)
FIG. 2(c) is an outline of the generation of a fusion mutant of AraC-LuxR$_{N86K\ and\ C245W}$.
FIG. 2(d) shows ligand evaluation results of an AND gate-type genetic switch.

The inventors of the present invention confirmed from the results of FIG. 2 and FIG. 6 described above that the response sensitivity of the sensor including the genetic switch obtained by the production method for a genetic switch of the present invention to each ligand depended on the concentration of the other ligand.

Figure 7:
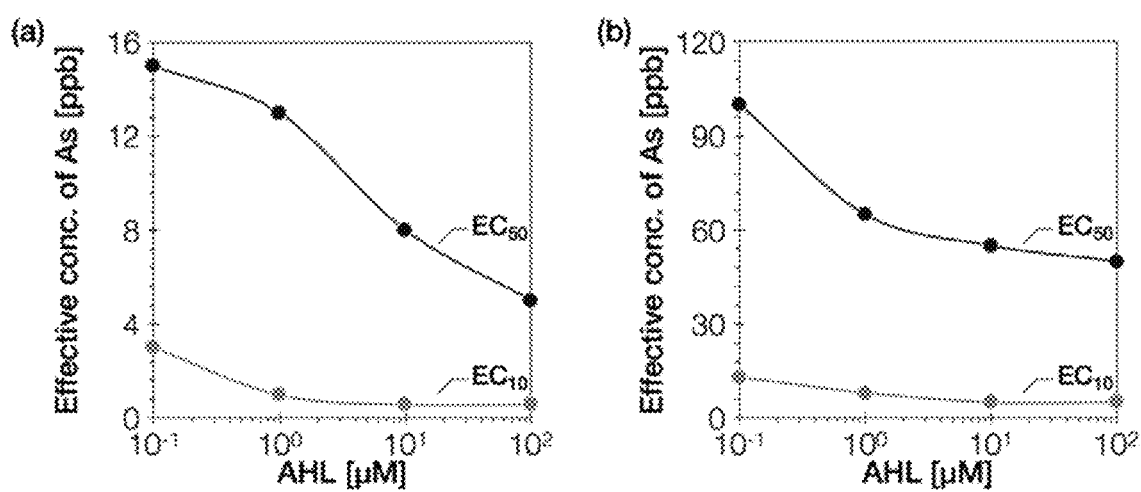
FIG. 7 are graphs obtained by plotting the EC50 value of a sensor including a 2-input AND-type arsenic switch against the concentration of AHL present in a system {FIG. 7(a) corresponds to FIG. 6(c), and FIG. 7(b) corresponds to FIG. 6(b)}.

Specifically, when the EC50 value of the sensor including the 2-input AND-type arsenic switch generated in Example 4 was plotted against the concentration of AHL present in the system, it was confirmed that the EC50 value reduced as the AHL concentration increased (see FIG. 7).

This phenomenon is a unique effect of the sensor including the genetic switch obtained by the method of the present invention. The AND-type genetic switch retains a functional structure in a manner dependent both on stabilization by binding to AHL and on stabilization by binding to arsenic. In the case of a genetic switch having such properties, as the concentration of AHL in the system increases, the effective concentration of ArsR serving as an arsenic sensor increases, and hence apparent sensitivity of "arsenic+ArsR↔arsenic•ArsR" increases.

That is, in the sensor including the genetic switch of the present invention, the sensitivity of the genetic switch to a ligand can be easily adjusted by the following method.

When the sensitivity of the ligand $L_1$ is to be increased, the addition concentration of the ligand $L_2$ is increased.

When the sensitivity of the ligand $L_1$ is to be decreased, the addition concentration of the ligand $L_2$ is decreased.

When the sensitivity of the ligand $L_2$ is to be increased, the addition concentration of the ligand $L_1$ is increased.

When the sensitivity of the ligand $L_2$ is to be decreased, the addition concentration of the ligand $L_1$ is decreased.

Example 6

(Selection Method for High-Sensitivity Genetic Switch)

The inventors of the present invention confirmed from the results of the foregoing Examples that the production method of the present invention was able to improve, for example, the sensitivity, output intensity, and stringency of the sensor.

For example, when the transcription factor LuxR is used, intentional detection with an arsenic detection switch based on the expression of a reporter gene downstream of the $P_1$ promoter has the following advantages.

(1) Output intensity and stringency: LuxR has the highest stringency (least expression leakage in a non-induced state) among transcription factors, and has a high maximum output when induced (transcription enhancing efficiency). Meanwhile, an ArsR/ArsP ($P_{ars}$) system has a low output intensity, and also has low stringency. Accordingly, the following result was obtained: the signal-to-noise ratio at the time of its response to arsenic was extremely low (see "ArsR→$P_{ars}$" of FIG. 8). In addition, in the AND of ArsR-LuxR, the following result was obtained: the stringency was even lower because of the influence of fusion (see "AND→$P_{ars}$" of FIG. 8). Meanwhile, when the reporter gene is arranged under LuxP, by virtue of an excellent SN ratio of LuxR/LuxP, a larger fluorescence value change is shown with respect to the arsenic concentration (see "ArsR→$P_{lux}$, AHL" of FIG. 8). That is, a genetic switch capable of high-sensitivity detection of a ligand can be selected by selecting a transcription factor (e.g., LuxR) capable of high-sensitivity detection as a fusion partner and selecting a promoter (e.g., LuxP) for the transcription factor.

(2) High-sensitivity detection of ligand: For example, in the case of the combination of the ArsR-LuxR transcription factor and the promoter ArsP, the expression profile of the reporter gene downstream of ArsP had an inflection point around 50 ppb. This detection sensitivity is nearly the same detection sensitivity as that in the case where ArsR alone is allowed to act on ArsP. However, in the case of the combination of the ArsR-LuxR transcription factor and the promoter $P_{lux}$, the expression profile of the reporter gene downstream of $P_{lux}$ had an inflection point around 5 ppb. This sensitivity is the world's highest sensitivity for a biosensor. An arsenic concentration serving as a WHO standard is 10 ppb. In the case of using an ArsR/ArsP system, the inflection point is present at a concentration that is one digit higher than the foregoing, and hence the ArsR/ArsP system cannot be used. However, in the case of the combination of the ArsR-LuxR transcription factor and the promoter $P_{lux}$, the combination can be used as it is for environmental monitoring.

This increase in sensitivity results from liberation from the operation mechanism of As-ArsR/ArsP as a "depressor". ArsR can originally bind to As with high affinity, but tightly binds to ArsP under an As-free state. That is, the ArsR structure in a repressed state is significantly stabilized by the binding to ArsP. Arsenic cancels the stabilized structure to release ArsR from ArsP.

That is, the equilibrium of "As+ArsR⇌As-ArsR" is significantly shifted to the left due to the presence of ArsP (that is, the sensitivity is decreased). It is considered that, in the absence of ArsP, As-ArsR binding to be read by LuxP is liberated from the sensitivity-decreasing effect, and hence the nearly one-digit increase in sensitivity is achieved.

Example 7

In this Example, in order to ascertain that it was possible to produce the 2-input-type sensor developed in the foregoing even by using an enzyme as a material, an enzyme PrpC or PrpD was used in place of the arabinose sensor (AraC) or the arsenic sensor (ArsR). The details are as described below. PrpC and PrpD are *E. coli*-derived enzymes called 2-methylcitrate synthase (EC:2.3.3.5) and 2-methylcitrate dehydratase (EC:4.2.1.3), respectively.

(1-1) Generation of PrpC::LuxR$_{N86K\text{-}C245W}$ and PrpD::LuxR$_{N86K\text{-}C245W}$ (1-1-1) Preparation of Vector for PrpC::LuxR$_{N86K\text{-}C245W}$ and PrpD::LuxR$_{N86K\text{-}C245W}$ Plasmid-12 (see Table 7) was subjected to digestion with NcoI-HF (commercially available restriction enzyme) and SpeI-HF (commercially available restriction enzyme), and subjected to gel extraction.

(1-1-2) Preparation of PrpC and PrpD Domains

The genome of the *E. coli* strain MG1655 was used as a template and subjected to PCR (Q5 ploymerase) treatment with Primer-15 and Primer-16 or Primer-17 and Primer-18 (see Table 6) to give a PCR product. Next, the PCR product was subjected to DpnI treatment and then subjected to gel extraction.

(1-1-3) Recovery of PrpC::LuxR$_{N86K\text{-}C245W}$ and PrpC::LuxR$_{N86K\text{-}C245W}$ The vector fragment of the section "1-1-1" and the insert fragment of the section "1-1-2" were subjected to the Gibson assembly method using a commercially available enzyme to assemble the DNA fragments. Next, XL10-Gold (commercially available competent cells) was transformed with the Gibson assembly product, and clones were recovered (Plasmid-14 and Plasmid-15).

(1-2) Generation of pMC-$P_{lux}$-GFP (1-2-1) Preparation of Vector for pMC-$P_{lux}$-GFP Plasmid-16 (see Table 7) was subjected to PCR (KOD plus) treatment with Primer-19 and Primer-20 (see Table 6) to give a PCR product. Next, the PCR product was subjected to DpnI treatment and then subjected to gel extraction. The extract was subjected to PCR (KOD plus) treatment with Primer-19 and Primer-21 (see Table 6) to give a PCR product. Next, the PCR product was subjected to gel extraction. The extract was subjected to digestion with ApaI (commercially available restriction enzyme), HindIII-HF (commercially available restriction enzyme), and rSAP (commercially available phosphatase), and further subjected to gel extraction.

(1-2-2) Preparation of GFP-hsvTK::APH Domain with Randomized RBS

Plasmid-5 (see Table 7) was used as a template and subjected to PCR (KOD plus) treatment with Primer-22 and Primer-23 (see Table 6) to give a PCR product. Next, the PCR product was subjected to DpnI treatment and then subjected to gel extraction. The extract was subjected to digestion with ApaI and HindIII-HF, and further subjected to gel extraction.

(1-2-3) Recovery of RBS Library of pMC-$P_{lux}$-GFP

The vector fragment of the section "1-2-1" and the insert fragment of the section "1-2-2" were subjected to ligation. Next, XL10-Gold (commercially available competent cells) was transformed with the ligation product, and clones were recovered.

(1-2-4) Recovery of pMC-P$_{lux}$-GFP

The *E. coli* strain BW25113 was transformed with the library plasmids of the section "1-2-3" and Plasmid-17. 30 of isolated colonies were randomly selected, and subjected to liquid culture overnight. A 1/100 amount of the preculture solution was inoculated into medium containing or not containing 1 μM AHL, and was cultured for 12 hours. Next, 200 μL of a measurement sample obtained by diluting the culture solution 10-fold with physiological saline was prepared. Cell density (OD595) and fluorescence at 535 nm at the time of excitation at 482 nm were measured using FilterMax F5 (commercially available absorbance detection system). As a blank sample (control), 200 μL of a blank sample obtained by diluting liquid medium 10-fold with physiological saline was also subjected to measurement simultaneously. Data analysis was performed with a value obtained by subtracting the measured value of the blank sample from the measured value of the sample. On the basis of the obtained data, the RBS mutant having the largest change between the fluorescence intensity in the case of containing AHL and that in the case of not containing AHL was isolated and recovered.

(1-3) Generation of PrpC$_{K318R}$::LuxR$_{N86K-C245W}$ and PrpD$_{S163T-A225G-I285V}$::LuxR$_{N86K-C245W}$ (1-3-1) Preparation of Vectors for PrpC::LuxR$_{N86K-C245W}$ and PrpD::LuxR$_{N86K-C245W}$ Libraries Plasmid-14 or Plasmid-15 (see Table 7) was subjected to inverse PCR (Q5 ploymerase) treatment with Primer-24 and Primer-25 (see Table 6) to give a PCR product. Next, the PCR product was subjected to DpnI treatment and then subjected to gel extraction.

(1-3-2) Preparation of PrpC-LuxR$_{N86K-C245W}$ and PrpD-LuxR$_{N86K-C245W}$ Domain Libraries Plasmid-14 or Plasmid-15 (see Table 7) was used as a template and subjected to error prone PCR (Taq ploymerase) treatment with Primer-26 and Primer-27 (see Table 6) to give a PCR product. Next, the PCR product was subjected to DpnI treatment and then subjected to gel extraction.

(1-3-3) Recovery of PrpC::LuxR$_{N86K-C245W}$ and PrpD::LuxR$_{N86K-C245W}$ Library Plasmids The vector fragment of the section "1-3-1" and the insert fragment of the section "1-3-2" were subjected to the Gibson assembly method using a commercially available enzyme to assemble the DNA fragments. Next, BW25113 (commercially available competent cells) was transformed with the Gibson assembly product, and library plasmids were recovered.

(1-3-4) Recovery of pET23d-PrpC$_{K318R}$::LuxR$_{N86K-C245W}$ and pET23d-PrpD$_{S163T-A225G-I285V}$::LuxR$_{N86K-C245W}$ The *E. coli* strain BW25113 was transformed with the library plasmids of the section "1-3-3" and Plasmid-23, and applied to a screening plate containing 10 μM AHL and 50 mM propionic acid. From isolated colonies, 48 colonies emitting GFP fluorescence were selected and subjected to liquid culture overnight. A 1/100 amount of the preculture solution was inoculated into liquid medium containing or not containing 50 mM propionic acid, and was cultured for 12 hours. Next, 200 μL of a measurement sample obtained by diluting the culture solution 10-fold with physiological saline was prepared. Cell density (OD595) and fluorescence at 535 nm at the time of excitation at 482 nm were measured using FilterMax F5 (commercially available absorbance detection system). As a blank sample (control), 200 μL of a blank sample obtained by diluting liquid medium 10-fold with physiological saline was also subjected to measurement simultaneously. Data analysis was performed with a value obtained by subtracting the measured value of the blank sample from the measured value of the sample. On the basis of the obtained data, the mutant having the largest change between the fluorescence intensity in the case of containing propionic acid and that in the case of not containing propionic acid was isolated and recovered, and its sequence was analyzed to identify mutation sites (full-length amino acid sequence of PrpC$_{K318R}$-LuxR$_{N86K\ and\ C245W}$: SEQ ID NO: 31, full-length amino acid sequence of PrpD$_{S163T-A225G-I285V}$-LuxR$_{N86K\ and\ C245W}$: SEQ ID NO: 32).

(2) Propionic Acid Responsiveness Evaluation with pMC-P$_{lux}$-GFP

BW25113 was transformed with a reporter plasmid pMC-P$_{lux}$-GFP (Plasmid 13: see Table 7). One transformant was selected, and competent cells (*E. coli*) were generated.

Figure 19:
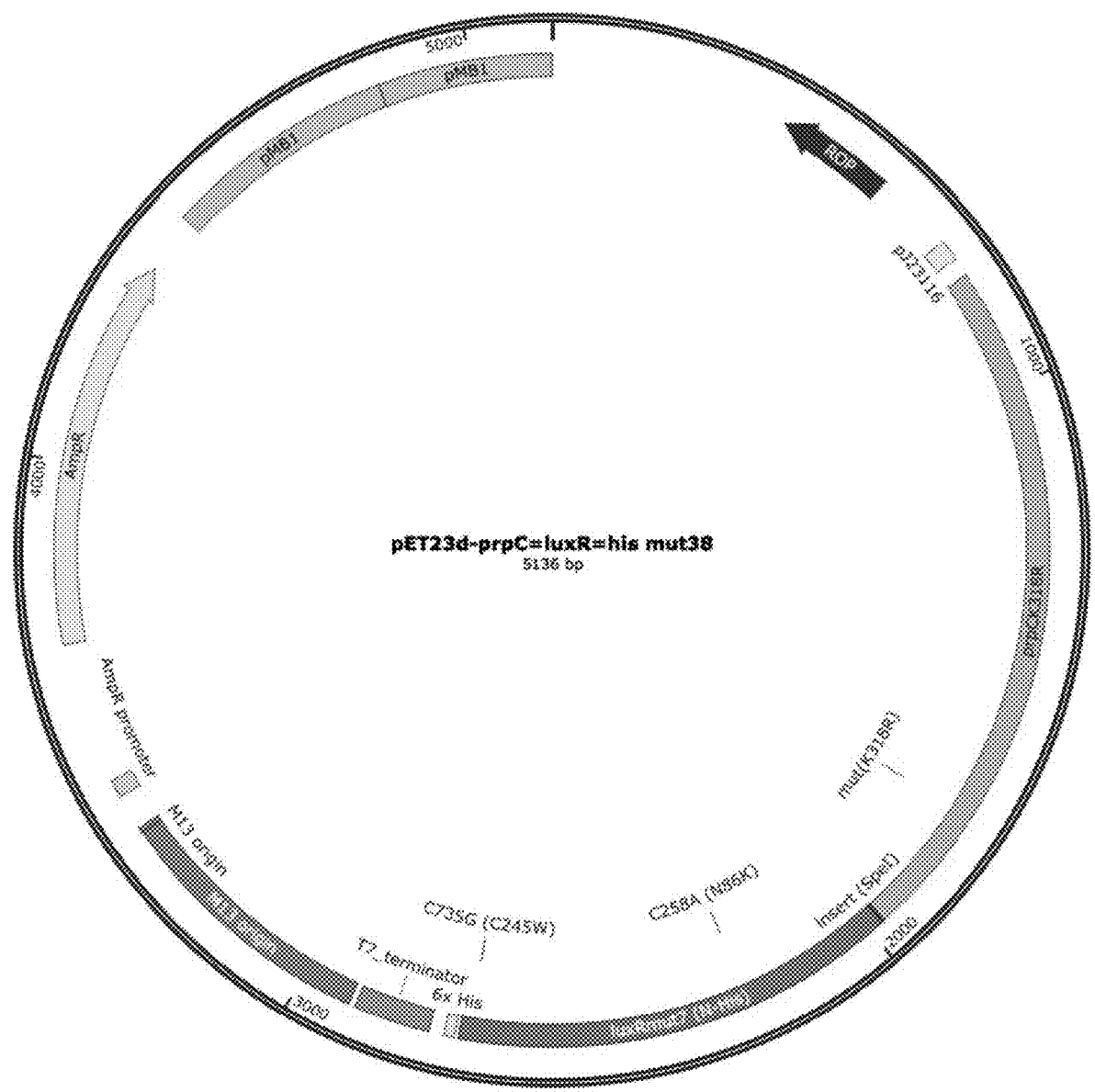
FIG. 19 is an outline of the plasmid structure of pET23d-PrpC::LuxR$_{mut}$.
Figure 20:
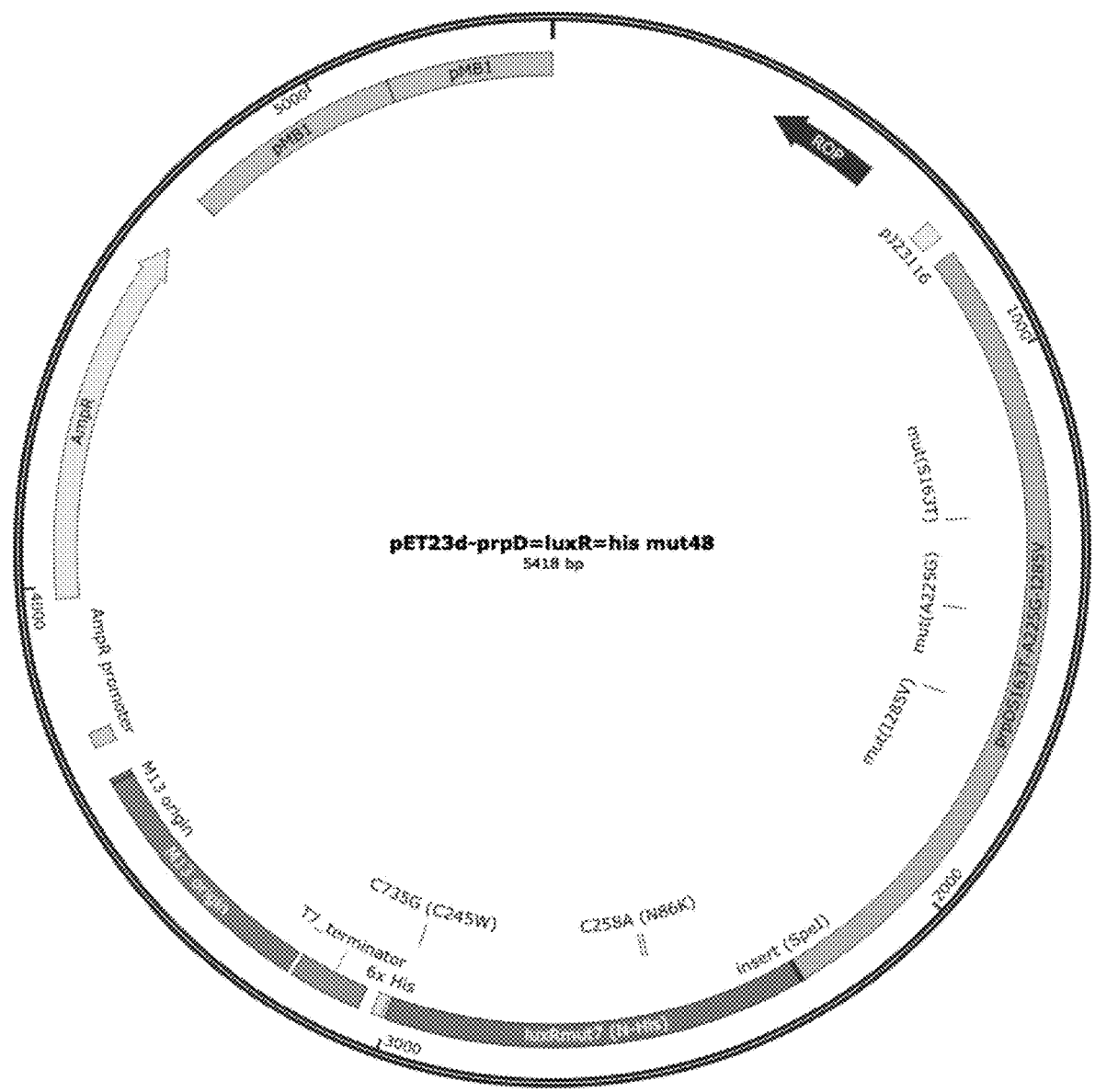
FIG. 20 is an outline of the plasmid structure of pET23d-PrpD::LuxR$_{mut}$.

The competent cells (*E. coli*) were transformed with pET23d-PrpC::LuxR$_{mut}$ (see FIG. 19) and pET23d-PrpD::LuxR$_{mut}$ (see FIG. 20) (Plasmids 18 and 19: see Table 7). Three of colonies formed on solid medium were randomly selected, and subjected to liquid culture overnight. A 1/100 amount of the preculture solution was inoculated into liquid media containing 10 μM and having arbitrary different sodium propionate concentrations, and was cultured for 12 hours. Next, 200 μL of a measurement sample obtained by diluting the culture solution 10-fold with physiological saline was prepared. Cell density (OD$_{595}$) and fluorescence at 535 nm at the time of excitation at 485 nm were measured using FilterMax F5 (commercially available absorbance detection apparatus). As a blank sample (control), 200 μL of a blank sample obtained by diluting liquid medium 10-fold with physiological saline was also subjected to measurement simultaneously. Data analysis was performed with a value obtained by subtracting the measured value of the blank sample from the measured value of the sample. Fluorescence intensities per cell density in the case of culture were evaluated.

Figure 21:
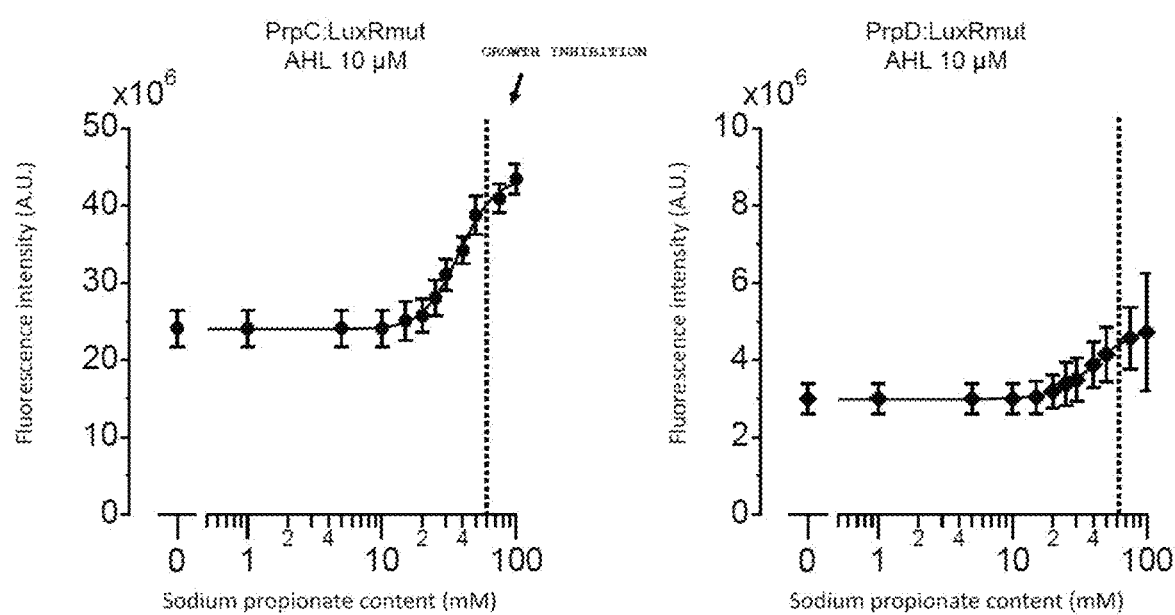
FIG. 21 shows results of propionic acid responsiveness evaluation.

The results are shown in FIG. 21. Propionic acid is converted to propionyl-CoA serving as a substrate for PrpC in *E. coli*, and is then converted to 2-methylcitric acid serving as a substrate for the enzyme PrpD. When PrpC and PrpD in PrpC::LuxR and PrpD::LuxR bind to respective substrates (propionyl-CoA and 2-methylcitric acid), PrpC::LuxR and PrpD::LuxR are stabilized to increase the transcription activity of LuxR, and the LuxR binds to P$_{lux}$ of P$_{lux}$-GFP to transcribe GFP. Accordingly, in FIG. 21, the fluorescence intensity increased in a propionic acid concentration-dependent manner.

(General Remark)

As apparent from Examples described above, the production method for a genetic switch of the present invention is a method according to which not only a variable-type sensor having an integrated and advanced function is produced, but also an output can be made as the function of a more excellent transcription factor by compensating for the disadvantage of a sensor function of low basic performance.

INDUSTRIAL APPLICABILITY

The production method for a multi-input/multi-output-type genetic switch or a transcription factor, and the multi-input/multi-output-type genetic switch or the transcription factor can be provided.

The invention claimed is:

1. A production method for a multi-input/multi-output-type genetic switch or a transcription factor for forming the switch, the method comprising one of (A) or (B), the method (A) including the following steps of (1) to (3):

(A)
(1) a step of introducing, into cells, or adding, to a cell-free protein synthesis system, a library of nucleic acids of fusion mutants of a binder $B_1$ or a transcription factor $T_1$, which responds to a ligand $L_1$, and a binder $B_2$ or a transcription factor $T_2$, which responds to a ligand $L_2$, the library being obtained by introducing mutations into a genetic construct carrying a gene sequence encoding the binder $B_1$ or the transcription factor $T_1$ and a gene sequence encoding the binder $B_2$ or the transcription factor $T_2$, and a reporter expression vector carrying a gene sequence encoding a promoter $P_1$ to be controlled by the transcription factor $T_1$ and/or a gene sequence encoding a promoter $P_2$ to be controlled by the transcription factor $T_2$, and a gene sequence encoding a reporter Rx functionally linked to the promoter sequence $P_1$ and/or the promoter sequence $P_2$, where X represents an integer of 1 or more;

(2) a step of adding the ligand $L_1$ and/or the ligand $L_2$ to the cells or the cell-free protein synthesis system of (1); and (3) a step of selecting one of the fusion mutants of the binder $B_1$ or the transcription factor $T_1$ and the binder $B_2$ or the transcription factor $T_2$ as a genetic switch or a transcription factor for forming the switch through use of an expression amount of the reporter as an indicator, or the method (B) including the following steps of (1) to (3):

(B)
(1) a step of introducing, into cells, or adding, to a cell-free protein synthesis system, a library of nucleic acids of fusion mutants of a binder $B_1$ or a transcription factor $T_1$, which responds to a ligand $L_1$, a binder $B_2$ or a transcription factor $T_2$, which responds to a ligand $L_2$, and a binder $B_N$ or a transcription factor $T_N$, which responds to a ligand $L_N$, the library being obtained by introducing mutations into a genetic construct carrying a gene sequence encoding the binder $B_1$ or the transcription factor $T_1$, a gene sequence encoding the binder $B_2$ or the transcription factor $T_2$, and a gene sequence encoding the binder $B_N$ or the transcription factor $T_N$, and a reporter expression vector carrying a gene sequence encoding a promoter $P_1$ to be controlled by the transcription factor $T_1$, a gene sequence encoding a promoter $P_2$ to be controlled by the transcription factor $T_2$, and/or a gene sequence encoding a promoter $P_N$ to be controlled by the transcription factor $T_N$, and a gene sequence encoding a reporter Rx functionally linked to the promoter sequence $P_1$, the promoter sequence $P_2$, and/or the promoter sequence $P_N$, where N represents an integer of 3 or more;

(2) a step of introducing the ligand $L_1$, the ligand $L_2$, and/or the ligand $L_N$ into the cells or the cell-free protein synthesis system of (1); and (3) a step of selecting one of the fusion mutants of the binder $B_1$ or the transcription factor $T_1$, the binder $B_2$ or the transcription factor $T_2$, and the binder $B_N$ or the transcription factor $T_N$ as a genetic switch or a transcription factor for forming the switch through use of an expression amount of the reporter as an indicator.

2. The method according to claim 1, wherein in the method (A), the step of selecting comprises selecting a fusion mutant having a high ratio of an expression amount of the reporter obtained by introduction of the ligand $L_1$ and the ligand $L_2$ to an expression amount of the reporter obtained by introduction of the ligand $L_1$ or the ligand $L_2$ as a genetic switch having a 2-input/AND-type output sensor function or a transcription factor for forming the switch.

3. The method according to claim 1, wherein in the method (A), when the promoter $P_2$ to be controlled by the transcription factor $T_2$ is used, the step of selecting comprises selecting a fusion mutant having a high ratio of an expression amount of the reporter obtained by introduction of the ligand $L_1$ and the ligand $L_2$ to an expression amount of the reporter obtained by introduction of the ligand $L_2$ as a genetic switch having a 2-input/AND-type output sensor function or a transcription factor for forming the switch, or when the promoter $P_1$ to be controlled by the transcription factor $T_1$ is used, the step of selecting comprises selecting a fusion mutant having a high ratio of an expression amount of the reporter obtained by introduction of the ligand $L_1$ and the ligand $L_2$ to an expression amount of the reporter obtained by introduction of the ligand $L_1$ as a genetic switch having a 2-input/AND-type output sensor function or a transcription factor for forming the switch.

4. The method according to claim 1, wherein in the method (A), when the promoter $P_1$ to be controlled by the transcription factor $T_1$ is used, the step of selecting comprises selecting a fusion mutant having a high ratio of an expression amount of the reporter obtained by introduction of the ligand $L_2$ to an expression amount of the reporter obtained without any ligand as a genetic switch having a 2-input/OR-type sensor function or a transcription factor for forming the switch, or when the promoter $P_2$ to be controlled by the transcription factor $T_2$ is used, the step of selecting comprises selecting a fusion mutant having a high ratio of an expression amount of the reporter obtained by introduction of the ligand $L_1$ to an expression amount of the reporter obtained without any ligand as a genetic switch having a 2-input/OR-type sensor function or a transcription factor for forming the switch.

5. The method according to claim 1, wherein in the method (A), when the promoter $P_1$ to be controlled by the transcription factor $T_1$ is used, the step of selecting comprises selecting a fusion mutant having a high ratio of an expression amount of the reporter obtained by introduction of the ligand $L_1$ to an expression amount of the reporter obtained by introduction of the ligand $L_2$ as a genetic switch for an output-type sensor that specifically responds to the ligand $L_1$ or a transcription factor for forming the switch, or when the promoter $P_2$ to be controlled by the transcription factor $T_2$ is used, the step of selecting comprises selecting a fusion mutant having a high ratio of an expression amount of the reporter obtained by introduction of the ligand $L_2$ to an expression amount of the reporter obtained by introduction of the ligand $L_1$ as a genetic switch for an output-type sensor that specifically responds to the ligand $L_2$ or a transcription factor for forming the switch.

6. The method according to claim 1, wherein in the method (A), when the promoter $P_1$ to be controlled by the transcription factor $T_1$ is used, the step of selecting comprises selecting a fusion mutant having a high ratio of an expression amount of the reporter obtained without any ligand to an expression amount of the reporter obtained by introduction of the ligand $L_1$, and having a high ratio of the expression amount of the reporter obtained without any ligand to an expression amount of the reporter obtained by introduction of the ligand $L_2$ as a genetic switch having a NOR-type sensor function or a transcription factor for forming the switch.

7. The method according to claim 1, wherein in the method (A), when the promoter $P_1$ to be controlled by the transcription factor $T_1$ is used, the step of selecting comprises selecting a fusion mutant having a high ratio of an expression amount of the reporter obtained without any ligand or obtained by introduction of one of the ligand $L_1$ or the ligand $L_2$ to an expression amount of the reporter obtained by introduction of the ligand $L_1$ and the ligand $L_2$ as a genetic switch having a NAND-type sensor function or a transcription factor for forming the switch.

8. The method according to claim 1, wherein in the method (A), the step of selecting comprises selecting a fusion mutant in which both of an expression amount of the reporter obtained by introduction of the ligand $L_1$ and an expression amount of the reporter obtained by introduction of the ligand $L_2$ are decreased as a genetic switch having a function as a 2-input/3-stage output reduction-type sensor or a transcription factor for forming the switch.

9. The method according to claim 1, wherein in the method (A), the step of selecting comprises selecting a fusion mutant in which both of an expression amount of the reporter obtained by introduction of the ligand $L_1$ and an expression amount of the reporter obtained by introduction of the ligand $L_2$ are increased as a genetic switch having a function as a 2-input/3-stage output increase-type sensor or a transcription factor for forming the switch.

10. The method according to claim 1, wherein in the method (B), N=3, and the step of selecting comprises selecting a fusion mutant in which an expression amount of the reporter obtained by introduction of the ligand $L_1$, an expression amount of the reporter obtained by introduction of the ligand $L_2$, and an expression amount of the reporter obtained by introduction of a ligand $L_3$ are decreased as a genetic switch having a function as a 3-input/4-stage output reduction-type sensor or a transcription factor for forming the switch.

* * * * *